United States Patent
Peng et al.

(10) Patent No.: US 9,850,206 B2
(45) Date of Patent: Dec. 26, 2017

(54) S1P AND/OR ATX MODULATING AGENTS

(71) Applicant: BIOGEN MA INC., Cambridge, MA (US)

(72) Inventors: Hairuo Peng, Cambridge, MA (US); Edward Yin-Shiang Lin, Cambridge, MA (US); Jianhua Chao, Cambridge, MA (US); Zhili Xin, Cambridge, MA (US); Bin Ma, Cambridge, MA (US); Kevin Guckian, Cambridge, MA (US); Timothy Chan, Cambridge, MA (US); Gnanasambandam Kumaravel, Cambridge, MA (US); Arthur G. Taveras, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

(21) Appl. No.: 14/443,912

(22) PCT Filed: Nov. 20, 2013

(86) PCT No.: PCT/US2013/070878
§ 371 (c)(1),
(2) Date: Oct. 29, 2015

(87) PCT Pub. No.: WO2014/081752
PCT Pub. Date: May 30, 2014

(65) Prior Publication Data
US 2015/0274663 A1    Oct. 1, 2015

Related U.S. Application Data

(60) Provisional application No. 61/728,723, filed on Nov. 20, 2012.

(51) Int. Cl.
C07D 211/22 (2006.01)
C07D 213/74 (2006.01)
(Continued)

(52) U.S. Cl.
CPC .......... *C07D 211/22* (2013.01); *A61K 31/451* (2013.01); *A61K 31/4545* (2013.01);
(Continued)

(58) Field of Classification Search
CPC .............. A61K 31/451; A61K 31/4545; A61K 31/495; A61K 31/501; A61K 31/506;
(Continued)

(56) References Cited

U.S. PATENT DOCUMENTS

2012/0018672 A1    1/2012    Kobayashi

FOREIGN PATENT DOCUMENTS

EP    0388967 A1    9/1990
EP    1308440 A1    5/2003
(Continued)

OTHER PUBLICATIONS

Yan, L., et al, Design and synthesis of conformationally constrained 3-(N-alkylamino)propylphosphonic acids as potent agonists of sphingosine-1-phosphate (S1P) receptors, Bioorganic & Medicinal Chemistry Letters, 14(19):4861-4866, Oct. 4, 2004.
(Continued)

*Primary Examiner* — Erich A Leeser
(74) *Attorney, Agent, or Firm* — McCarter & English, LLP; Steven G. Davis; Xin Zhang

(57) ABSTRACT

Compounds of formula (I) wherein: X is —O—, —S(O)$_r$—, —CH$_2$—, or —NR—, wherein r is 0, 1, or 2; $X^1$, $X^2$, and $X^5$ are each independently $CR^7$ or N; one of $X^3$ or $X^4$ is C and is attached by a single bond to -L-, and the other is $CR^7$ or N, provided that no more than three of $X^1$, $X^2$, $X^3$, X or $X^5$ are N; Ring A is monocyclic $C_{5-6}$scycloalkyl or a 5- to 6-membered monocyclic heterocyclyl comprising from 1 to 5 heteroatoms independently selected from N, S, or O; wherein Ring A is further optionally substituted with from 1 to 3 $R^4$; provided that Ring A is not morpholinyl, thiomorpholinyl or tetrahydro-2H-pyranyl; L is a bond, —O—, —NR—, —S(O)$_n$—, —CH$_2$—, or —C(O)—, wherein n is 0, 1, or 2; 1 2 $L^1$ is an $C_{1-8}$alkylene, $C_{3-x}$cycloalkylene, —CH$_2$-$L^2$-, or a 3- to 8-membered heterocyclylene comprising 1 to 5; $R^1$ is $C_{6-20}$alkyl or a monocyclic $C_{3-8}$cycloalkyl; wherein said $C_{3-8}$cycloalkyl is substituted with at least one $R^6$ and may be optionally substituted with from 1 to 5 additional $R^6$ substituents, wherein $R^6$ for each occurrence is independently selected; and $R^2$ is —C(O)OR$^3$, —C(O)N(R$^3$)—S(O)$_2$R$^3$, —S(O)$_2$OR$^3$, —C(O)NHC(O)R$^3$, —Si(O)OH, —B(OH)$_2$, —N(R$^3$)S(O)$_2$R$^3$, —S(O)$_2$N(R$^3$)$_2$, —O—P(O)(OR$^3$)$_2$, or —P(O)(OR$^3$)$_2$, —CN, —S(O)$_2$NHC(O)R$^3$, —C(O)NHS(O)$_2$R3, —C(O)NHOH, —C(O)NHCN, —CH(CF$_3$)OH, —C(CF$_3$)$_2$OH, or a selected heteroaryl or heterocyclyl; and pharmaceutically acceptable salts thereof, can modulate the activity of one or more SIP receptors and/or the activity of autotaxin (ATX).

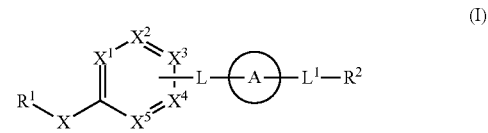

(I)

22 Claims, No Drawings

(51) Int. Cl.
*C07D 401/12* (2006.01)
*C07D 237/22* (2006.01)
*C07D 239/47* (2006.01)
*C07D 207/08* (2006.01)
*C07D 211/56* (2006.01)
*C07D 211/62* (2006.01)
*C07D 295/15* (2006.01)
*C07D 295/155* (2006.01)
*C07D 211/70* (2006.01)
*A61K 31/451* (2006.01)
*A61K 31/4545* (2006.01)
*A61K 31/495* (2006.01)
*A61K 31/501* (2006.01)
*A61K 31/506* (2006.01)
*A61K 45/06* (2006.01)
*C07D 401/04* (2006.01)
*C07D 403/04* (2006.01)

(52) U.S. Cl.
CPC .......... *A61K 31/495* (2013.01); *A61K 31/501* (2013.01); *A61K 31/506* (2013.01); *A61K 45/06* (2013.01); *C07D 207/08* (2013.01); *C07D 211/56* (2013.01); *C07D 211/62* (2013.01); *C07D 211/70* (2013.01); *C07D 213/74* (2013.01); *C07D 237/22* (2013.01); *C07D 239/47* (2013.01); *C07D 295/15* (2013.01); *C07D 295/155* (2013.01); *C07D 401/04* (2013.01); *C07D 401/12* (2013.01); *C07D 403/04* (2013.01)

(58) Field of Classification Search
CPC .... A61K 45/06; C07D 207/08; C07D 211/22; C07D 211/56; C07D 211/62; C07D 211/70; C07D 213/74; C07D 237/22; C07D 239/47; C07D 295/15; C07D 295/155; C07D 401/04; C07D 401/12; C07D 403/04
See application file for complete search history.

(56) References Cited

FOREIGN PATENT DOCUMENTS

| | | | |
|---|---|---|---|
| EP | 1661881 A2 | 5/2006 | |
| JP | 63101848 | 5/1988 | |
| WO | 9307111 A1 | 4/1993 | |
| WO | 9514681 A1 | 6/1995 | |
| WO | WO-2003066591 | 7/2003 | |
| WO | WO-2005/000833 A1 | 1/2005 | |
| WO | 2007024922 A1 | 3/2007 | |
| WO | 2010093704 A1 | 8/2010 | |
| WO | WO 2010/093704 * | 8/2010 | ........... C07C 215/10 |
| WO | 2011023795 A1 | 3/2011 | |

OTHER PUBLICATIONS

Haruto Kurata, et al. "Structure-activity relationship studies of sphingosine-1-phosphate receptor agonists with $N$-cinnamyl-$\beta$-alanine moiety", Bioorganic & Medicinal Chemistry Letters, vol. 2, 2011; pp. 1390-1393.

* cited by examiner

S1P AND/OR ATX MODULATING AGENTS

RELATED APPLICATIONS

This application is a 35 U.S.C. §371 national stage filing of International Application No. PCT/US2013/070878, filed Nov. 20, 2013, which claims the benefit of U.S. Provisional Patent Application No. 61/728,723, filed Nov. 20, 2012. The entire contents of each of the foregoing applications are hereby incorporated by reference.

Provided are agents that modulate S1P and/or ATX, and methods of making and using such agents.

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulating agent, FTY720 (2-amino-2-[2-(4-octylphenyl)ethyl]propane 1,3-diol), that following phosphorylation, is an agonist at 4 of 5 S1P receptors, revealed that affecting S1P receptor activity influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds. S1P type 4 receptors ($S1P_4$) are expressed mainly in leukocytes, and specifically $S1P_4$ mediates immunosuppressive effects of S1P by inhibiting proliferation and secretion of effector cytokines, while enhancing secretion of the suppressive cytokine IL-10. See, for example, Wang, W. et. al., (2005) *FASEB J.* 19(12): 1731-3, which is incorporated by reference in its entirety. S1P type 5 receptors ($S1P_5$) are exclusively expressed in oligodendrocytes and oligodendrocyte precursor cells (OPCs) and are vital for cell migration. Stimulation of $S1P_5$ inhibits OPC migration, which normally migrate considerable distances during brain development. See, for example, Novgorodov, A. et al., (2007) *FASEB J,* 21: 1503-1514, which is incorporated by reference in its entirety.

S1P has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing, tumor growth inhibition, and autoimmune diseases.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine-1-phosphate phosphohydrolases. Irreversible degradation of S1P is catalyzed by S1P lyase yielding ethanolamine phosphate and hexadecenal.

Autotaxin (ATX, ENPP2) is a secreted glycoprotein widely present in biological fluids, including blood, cancer ascites, synovial, pleural and cerebrospinal fluids, originally isolated from the supernatant of melanoma cells as an autocrine motility stimulation factor (Stracke, M. L., et al. Identification, purification, and partial sequence analysis of autotaxin, a novel motility-stimulating protein. J Biol Chem 267, 2524-2529 (1992), which is incorporated by reference in its entirety). ATX is encoded by a single gene on human chromosome 8 (mouse chromosome 15) whose transcription, regulated by diverse transcription factors (Hoxal3, NFAT-1 and v-jun), results in four alternatively spliced isoforms (α, β, γ, and δ). See, for example, Giganti, A., et al Murine and Human Autotaxin alpha, beta, and gamma Isoforms: Gene organization, tissue distribution and biochemical characterization. J Biol Chem 283, 7776-7789 (2008); and van Meeteren, L. A. & Moolenaar, W. H. Regulation and biological activities of the autotaxin-LPA axis. Prog Lipid Res 46, 145-160 (2007); Hashimoto, et al, "Identification and Biochemical Characterization of a Novel Autotaxin Isoform, ATXδ," J. of Biochemistry Advance Access (Oct. 11, 2011); each of which is incorporated by reference in its entirety.

ATX is synthesized as a prepro-enzyme, secreted into the extracellular space after the proteolytic removal of its N-terminal signal peptide (Jansen, S., el al Proteolytic maturation and activatio of autotaxin (NPP2), a secreted metastasis-enhancing lysophospho lipase D. J Cell Sci 118, 3081-3089 (2005), which is incorporated by reference in its entirety). ATX is a member of the ectonucleotide pyrophosphatase/ phosphodiesterase family of ectoenzymes (E-NPP) that hydrolyze phosphodiesterase (PDE) bonds of various nucleotides and derivatives (Stefan, C, Jansen, S. & Bollen, M. NPP-type ectophosphodiesterases: unity in diversity. Trends Biochem Sci 30, 542-550 (2005), which is incorporated by reference in its entirety). The enzymatic activity of ATX was enigmatic, until it was shown to be identical to lysophospholipase D (lysoPLD) (Umezu-Goto, M., et al. Autotaxin has lysophospholipase D activity leading to tumor cell growth and motility by lysophosphatidic acid production. J Cell Biol 158, 227-233 (2002), which is incorporated by reference in its entirety), which is widely present in biological fluids. Since ATX is a constitutively active enzyme, the biological outcome of ATX action will largely depend on its expression levels and the local availability of its substrates. The major lysophospholipid substrate for ATX, lysophosphatidylcholine (LPC), is secreted by the liver and is abundantly present in plasma (at about 100 μM) as a predominantly albumin bound form (Croset, M., Brossard, N., Polette, A. & Lagarde, M. Characterization of plasma unsaturated lysophosphatidylcholines in human and rat Biochem J 345 Pt 1, 61-67 (2000), which is incorporated by reference in its entirety). LPC is also detected in tumor-cell conditioned media (Umezu-Goto, M., et al.), presumably as a constituent of shed microvesicles. ATX, through its lysoPLD activity converts LPC to lysophosphatidic acid (LPA).

LPC is an important inflammatory mediator with recognized effects in multiple cell types and pathophysiological processes. It is a major component of oxidized low density lipoprotein (oxLDL) and it can exist in several other forms including free, micellar, bound to hydrophobic proteins such as albumin and incorporated in plasma membranes. It is produced by the hydrolysis of phosphatidylcholine (PC) by PLA2 with concurrent release of arachidonic acid and in turn of other pro-inflammatory mediators (prostaglandins and leukotrienes). Moreover, LPC externalization constitutes a chemotactic signal to phagocytic cells, while interaction with its receptors can also stimulate lymphocytic responses. LPC has been shown to have therapeutic effects in experimental sepsis, possibly by suppressing endotoxin-induced HMGB1 release from macrophages/monocytes.

LPA is a bioactive phospholipid with diverse functions in almost every mammalian cell line (Moolenaar, W. H., van Meeteren, L. A. & Giepmans, B. N. The ins and outs of lysophosphatidic acid signaling. Bioessays 28, 870-881 (2004), which is incorporated by reference in its entirety). LPA is a major constituent of serum bound tightly to albumin, gelsolin and possibly other as yet unidentified proteins. See, e.g., Goetzl, E. J., et al Gelsolin binding and. cellular presentation of lysophosphatidic acid. J Biol Chem 275, 14573-14578 (2000); and Tigyi, G. & Miledi, R, Lysophosphatidates bound to serum albumin activate membrane currents in *Xenopus* oocytes and neurite retraction in PC 12 pheochromocytoma cells. J Biol Chem 267, 21360-21367 (1992); each of which is incorporated by reference in its entirety.

LPA is also found in other biofluids, such as saliva and follicular fluid, and has been implicated in a wide array of functions, such as wound heeling, tumor invasion and metastasis, neurogenesis, myelination, astrocytes outgrowth and neurite retraction. The long list of LPA functions was also explained with the discovery that it signals through G-protein coupled receptors (GPCRs), via classical second messenger pathways. Five mammalian cell-surface LPA receptors have been identified so far. The best known are LPA1-3 (namely Edg-2, Edg-4 and Edg7) which are all members of the so-called 'endothelial differentiation gene' (EDG) family of GPCRs (Contos, J. J., Ishii, I. & Chun, J. Lysophosphatidic acid receptors. Mol Pharmacol 58, 1188-1196 (2000), which is incorporated by reference in its entirety). LPA receptors can couple to at least three distinct G proteins ($G_q$, $G_i$ and $G_{12/13}$), which, in turn, feed into multiple effector systems. LPA activates $G_q$ and thereby stimulates phospholipase C (PLC), with subsequent phosphatidylinositol-bisphosphate hydrolysis and generation of multiple second messengers leading to protein kinase C activation and changes in cytosolic calcium. LPA also activates $G_i$, which leads to at least three distinct signaling routes: inhibition of adenylyl cyclase with inhibition of cyclic AMP accumulation; stimulation of the mitogenic RAS-MAPK (mitogen-activated protein kinase) cascade; and activation of phosphatidylinositol 3-kinase (PI3K), leading to activation of the guanosine diphosphate/guanosine triphosphate (GDP/GTP) exchange factor TIAM1 and the downstream RAC GTPase, as well as to activation of the AKT/PKB antiapoptotic pathway. Finally, LPA activates $G_{12/13}$, leading to activation of the small GTPase RhoA, which drives cytoskeletal contraction and cell rounding. So, LPA not only signals via classic second messengers such as calcium, diacylglycerol and cAMP, but it also activates RAS- and RHO-family GTPases, the master switches that control cell proliferation, migration and morphogenesis.

LPA signaling through the RhoA-Rho kinase pathway mediates neurite retraction and inhibition of axon growth. Interfering with LPA signaling has been shown to promote axonal regeneration and functional recovery after CNS injury or cerebral ischemia. (See Broggini, et al., *Molecular Biology of the Cell* (2010), 21:521-537.) It has been reported that addition of LPA to dorsal root fibers in ex vivo culture causes demyelination, whereas LPC fails to cause significant demyelination of nerve fibers in ex vivo cultures without further addition of recombinant ATX to the culture which when added caused significant demyelination at equivalent levels to LPA presumable due to conversion of LPC to LPA through the enzymatic activity of ATX. Moreover, injury induced demyelination was attenuated by about 50% in $atx^{+/-}$ mice (Nagai, et al., *Molecular Pain* (2010), 6:78).

A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve (e.g. in Bell's palsy)), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency and copper deficiency. Other demyelination disorders may have unknown causes or multiple causes such as trigeminal neuralgia, Marchiafava-Bignami disease and Bell's palsy.

One practically successful approach to treating demyelination disorders which are caused by autoimmune dysfunction has been to attempt to limit the extent of demyelination by treating the patient with immunoregulatory drugs. However, typically this approach has merely postponed but not avoided the onset of disability in these patients. Patients with demyelination due to other causes have even fewer treatment options. Therefore, the need exists to develop new treatments for patients with demyelination diseases or disorders.

Provided are agents that can modulate S1P and/or ATX, e.g., an S1P4 antagonist and/or ATX inhibitor.

Provided is a compound represented by formula (I):

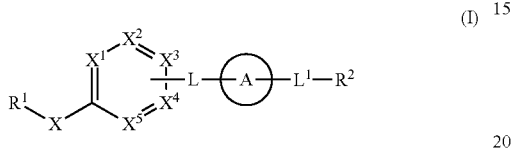

(I)

or a pharmaceutically acceptable salt thereof, wherein:
X is —O—, —S(O)$_r$—, —CH$_2$—, or —NR—, wherein r is 0, 1, or 2;
$X^1$, $X^2$, and $X^5$ are each independently $CR^7$ or N;
one of $X^3$ or $X^4$ is C and is attached by a single bond to -L-, and the other is $CR^7$ or N, provided that no more than three of $X^1$, $X^2$, $X^3$, $X^4$ or $X^5$ are N;
Ring A is monocyclic C$_{5-6}$cycloalkyl or a 5- to 6-membered monocyclic heterocyclyl comprising from 1 to 5 heteroatoms independently selected from N, S, or O; wherein Ring A is further optionally substituted with from 1 to 3 $R^4$; provided that Ring A is not morpholinyl, thiomorpholinyl or tetrahydro-2H-pyranyl;
L is a bond, —O—, —NR—, —S(O)$_n$—, —CH$_2$—, or —C(O)—, wherein n is 0, 1, or 2;
$L^1$ is an C$_{1-8}$alkylene, C$_{3-8}$cycloalkylene, —CH$_2$-L$^2$-, or a 3- to 8-membered heterocyclylene comprising 1 to 5 heteroatoms selected from N, S, or O; wherein $L^1$ may be optionally substituted with from 1 to 3 independently selected $R^5$;
$L^2$ is a divalent bridged ring system comprising 6-10 ring members, wherein the ring members may be all carbon atoms or may comprise 1 to 5 heteroatoms selected from N, S, or O;
R, for each occurrence, is independently hydrogen or C$_{1-8}$alkyl;
$R^1$ is C$_{6-20}$alkyl or a monocyclic C$_{3-8}$cycloalkyl; wherein said C$_{3-8}$cycloalkyl is substituted with at least one $R^6$ and may be optionally substituted with from 1 to 5 additional $R^6$ substituents, wherein $R^6$ for each occurrence is independently selected;
$R^2$ is —C(O)OR$^3$, —C(O)N(R$^3$)—S(O)$_2$R$^3$, —S(O)$_2$OR$^3$, —C(O)NHC(O)R$^3$, —Si(O)OH, —B(OH)$_2$, —N(R$^3$)S(O)$_2$R$^3$, —S(O)$_2$N(R$^3$)$_2$, —O—P(O)(OR$^3$)$_2$, or —P(O)(OR$^3$)$_2$, —CN, —S(O)$_2$NHC(O)R$^3$, —C(O)NHS(O)$_2$R$^3$, —C(O)NHOH, —C(O)NHCN, —CH(CF$_3$)OH, —C(CF$_3$)$_2$OH, or a heteroaryl or a heterocyclyl selected from the group consisting of formulae (a)-(i'):

(a)
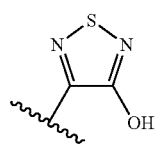

(b)
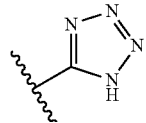

(c)
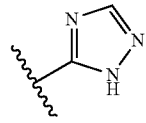

(d)
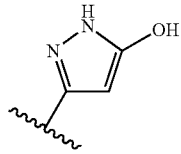

(e)
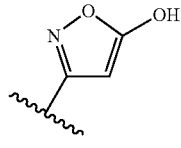

(f)
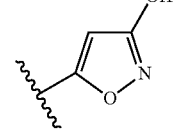

(g)
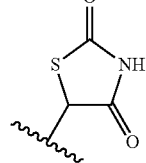

(h)
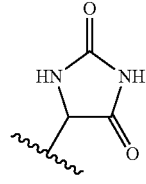

(i)
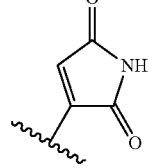

(j)
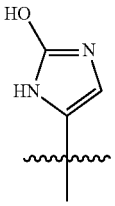

-continued
(k) 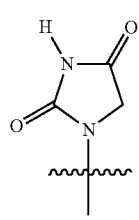
(l) 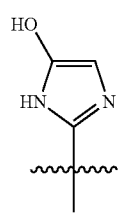
(m) 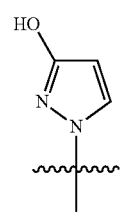
(n) 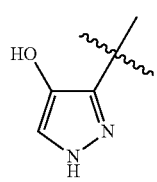
(o) 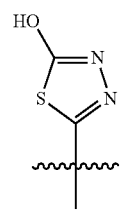
(p) 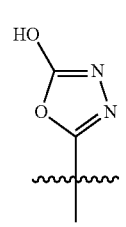
(q) 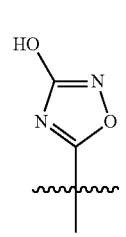
-continued
(r) 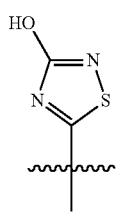
(s) 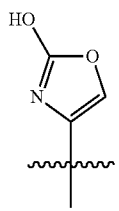
(t) 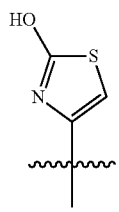
(u) 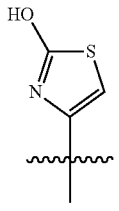
(v) 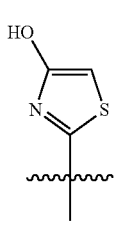
(w) 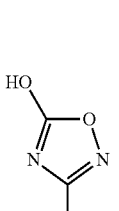
(x) 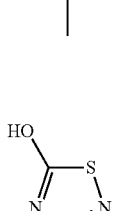

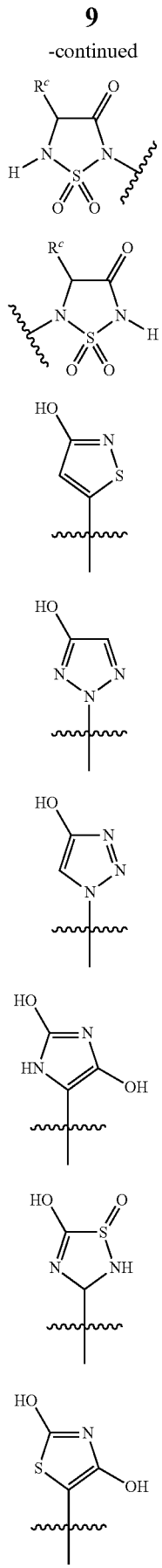

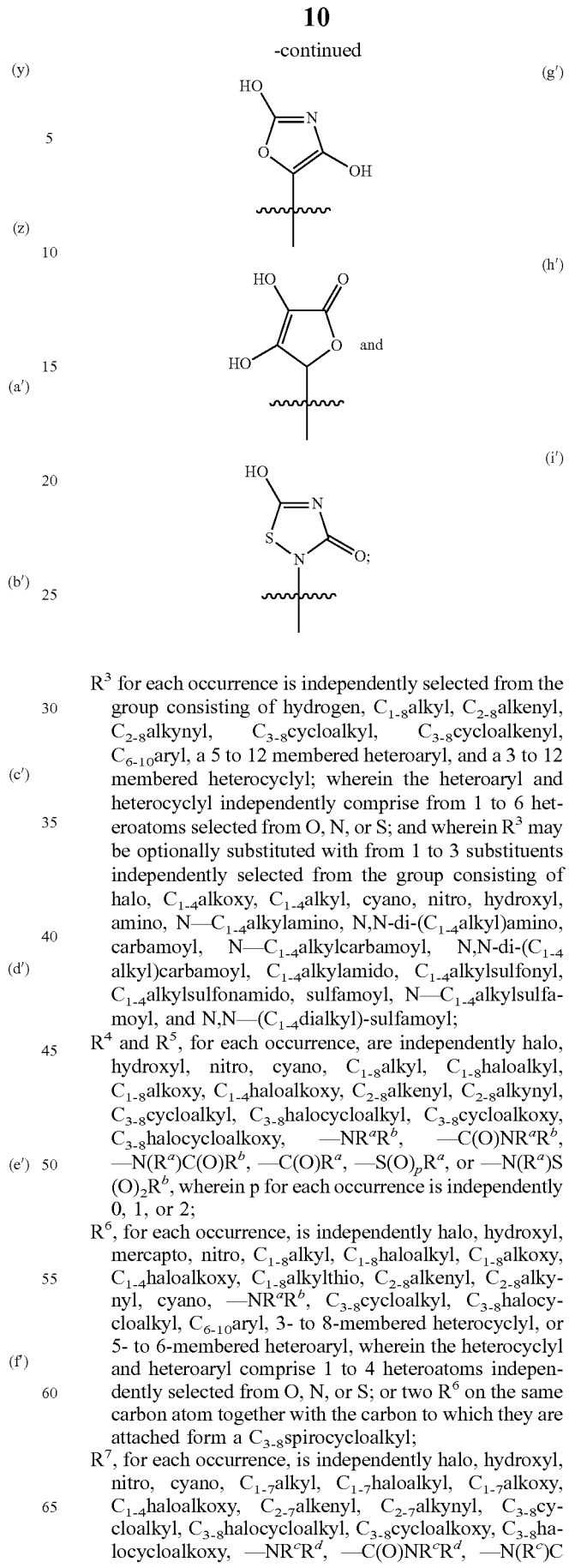

R³ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 12 membered heteroaryl, and a 3 to 12 membered heterocyclyl; wherein the heteroaryl and heterocyclyl independently comprise from 1 to 6 heteroatoms selected from O, N, or S; and wherein R³ may be optionally substituted with from 1 to 3 substituents independently selected from the group consisting of halo, $C_{1-4}$alkoxy, $C_{1-4}$alkyl, cyano, nitro, hydroxyl, amino, N—$C_{1-4}$alkylamino, N,N-di-($C_{1-4}$alkyl)amino, carbamoyl, N—$C_{1-4}$alkylcarbamoyl, N,N-di-($C_{1-4}$ alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl;

R⁴ and R⁵, for each occurrence, are independently halo, hydroxyl, nitro, cyano, $C_{1-8}$alkyl, $C_{1-8}$haloalkyl, $C_{1-8}$alkoxy, $C_{1-4}$haloalkoxy, $C_{2-8}$alkenyl, $C_{2-8}$alkynyl, $C_{3-8}$cycloalkyl, $C_{3-8}$halocycloalkyl, $C_{3-8}$cycloalkoxy, $C_{3-8}$halocycloalkoxy, —NR$^a$R$^b$, —C(O)NR$^a$R$^b$, —N(R$^a$)C(O)R$^b$, —C(O)R$^a$, —S(O)$_p$R$^a$, or —N(R$^a$)S(O)$_2$R$^b$, wherein p for each occurrence is independently 0, 1, or 2;

R⁶, for each occurrence, is independently halo, hydroxyl, mercapto, nitro, $C_{1-8}$alkyl, $C_{1-8}$haloalkyl, $C_{1-8}$alkoxy, $C_{1-4}$haloalkoxy, $C_{1-8}$alkylthio, $C_{2-8}$alkenyl, $C_{2-8}$alkynyl, cyano, —NR$^a$R$^b$, $C_{3-8}$cycloalkyl, $C_{3-8}$halocycloalkyl, $C_{6-10}$aryl, 3- to 8-membered heterocyclyl, or 5- to 6-membered heteroaryl, wherein the heterocyclyl and heteroaryl comprise 1 to 4 heteroatoms independently selected from O, N, or S; or two R⁶ on the same carbon atom together with the carbon to which they are attached form a $C_{3-8}$spirocycloalkyl;

R⁷, for each occurrence, is independently halo, hydroxyl, nitro, cyano, $C_{1-7}$alkyl, $C_{1-7}$haloalkyl, $C_{1-7}$alkoxy, $C_{1-4}$haloalkoxy, $C_{2-7}$alkenyl, $C_{2-7}$alkynyl, $C_{3-8}$cycloalkyl, $C_{3-8}$halocycloalkyl, $C_{3-8}$cycloalkoxy, $C_{3-8}$halocycloalkoxy, —NR$^c$R$^d$, —C(O)NR$^c$R$^d$, —N(R$^c$)C (O)R$^b$, —C(O)R$^a$, —S(O)$_p$R$^a$, and —N(R$^c$)S(O)$_2$R$^b$, wherein p is 0, 1, or 2; and R$^a$ and R$^b$, for each occurrence, are independently hydrogen, C$_{1-8}$alkyl, C$_{2-8}$alkenyl, C$_{2-8}$alkynyl, C$_{3-8}$cycloalkyl, C$_{6-10}$aryl, or C$_{3-8}$halocycloalkyl, provided that the compound is not

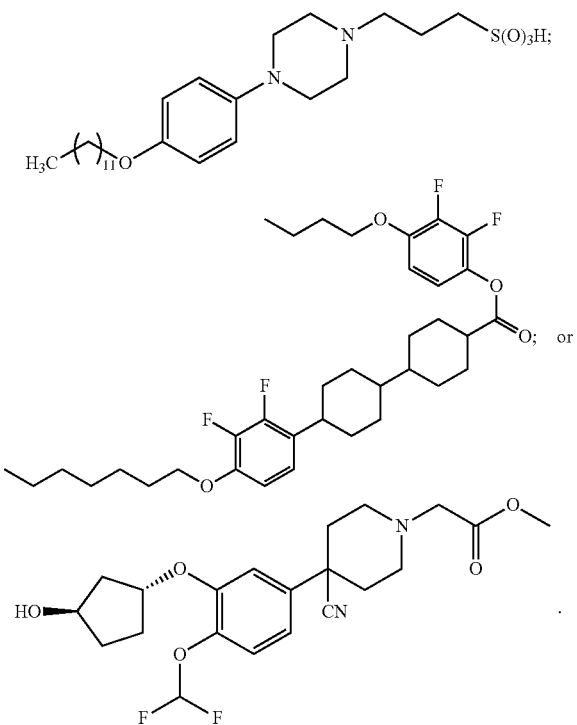

Also provided is a pharmaceutical composition comprising at least one compound disclosed herein, or a pharmaceutically acceptable salt thereof, and at least one pharmaceutically acceptable carrier.

Also provided is a method of preventing, treating, or reducing symptoms of a condition mediated by S1P activity and/or ATX activity in a mammal comprising administering to said mammal an effective amount of at least one compound, or a pharmaceutically acceptable salt thereof, described herein.

Also provided is a method of promoting myelination or remyelination in a mammal in need thereof, comprising administering to cells an effective amount of at least one compound, or a pharmaceutically acceptable salt thereof, described herein.

Also provided is a method of preventing, treating, or reducing chronic pain in a mammal comprising administering to said mammal an effective amount of at least one compound, or a pharmaceutically acceptable salt thereof, described herein.

Other features or advantages will be apparent from the following detailed description of several embodiments, and also from the appended claims.

As used in the present specification, the following words, phrases and symbols are generally intended to have the meanings as set forth below, except to the extent that the context in which they are used indicates otherwise.

As used herein, the term "alkyl" refers to a fully saturated branched or unbranched hydrocarbon moiety. In some embodiments, the alkyl comprises 1 to 20 carbon atoms, such as 1 to 16 carbon atoms, 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

As used herein, the term "alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. In some embodiments, the haloalkyl can be monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. In some embodiments, a haloalkyl group is trifluoromethyl or difluoromethyl.

As used herein, the term "halogen" or "halo" may be fluoro, chloro, bromo or iodo.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. In some embodiments, alkoxy groups have about 1-6 carbon atoms, such as about 1-4 carbon atoms.

As used herein, the term "haloalkoxy" refers to haloalkyl-O—, wherein haloalkyl is defined herein above. Representative example of haloalkoxy groups are trifluoromethoxy, difluoromethoxy, and 1,2-dichloroethoxy. In some embodiments, haloalkoxy groups have about 1-6 carbon atoms, such as about 1-4 carbon atoms.

As used herein, the term "alkylthio" refers to alkyl-S—, wherein alkyl is defined herein above.

As used herein, the term "carbocyclyl" refers to saturated or partially unsaturated (but not aromatic) monocyclic, bicyclic or tricyclic hydrocarbon groups of 3-14 carbon atoms, such as 3-9, for example, 3-8 carbon atoms. Carbocyclyls include fused or bridged ring systems. The term "carbocyclyl" encompasses cycloalkyl groups. The term "cycloalkyl" refers to completely saturated monocyclic, bicyclic or tricyclic hydrocarbon groups of 3-12 carbon atoms, such as 3-9, for example, 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, or bicyclo[2.2.2]octyl. Exemplary tricyclic carbocyclyl groups include adamantyl.

As used herein, the term "cycloalkylene" refers to a divalent cycloalkyl group. Examples of cycloalkylene groups include cyclopropylene, cyclobutylene, cyclopentylene, cyclohexylene and the like. In some embodiments, a cycloalkylene is a cyclohexylene. The cycloalkylene is attached to the rest of the molecule through a single bond and to the radical group through a single bond. The points of attachment of the cycloalkylene to the rest of the molecule and to the radical group can be through one carbon or any two carbons within the cycloalkylene group.

As used herein, the term "halocycloalkyl" refers to a cycloalkyl, as defined herein, that is substituted by one or more halo groups as defined herein. In some embodiments the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

As used herein, the term "cycloalkoxy" refers to cycloalkyl-O—, wherein cycloalkyl is defined herein above.

As used herein, the term "halocycloalkoxy" refers to halocycloalkyl-O—, wherein halocycloalkyl is defined herein above.

As used herein, the term "the term "aryl" refers to monocyclic, bicyclic or tricyclic aromatic hydrocarbon groups having from 6 to 14 carbon atoms in the ring portion. In some embodiments, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In some embodiments, a heterocyclyl is a 3-8-membered monocyclic. In some embodiments, a heterocyclyl is a 6-12-membered bicyclic. In some embodiments, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

As used herein, the term "heterocyclylene" refers to a divalent heterocyclyl group. An example of a heterocyclylene group is divalent piperidine. The heterocyclylene is attached to the rest of the molecule through a single bond and to the radical group through a single bond. The points of attachment of the heterocyclylene to the rest of the molecule and to the radical group can be through one atom in the heterocyclylene or through two separate atoms of the heterocyclylene. In addition, the point of attachment to the rest of the molecule and/or to the radical group may be through a carbon atom or a heteroatom.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

As used herein, the term "bridged ring system," is a ring system that has a carbocyclyl or heterocyclyl ring wherein two non-adjacent atoms of the ring are connected (bridged) by one or more (such as from one to three) atoms. A bridged ring system can have more than one bridge within the ring system (e.g., adamantyl). A bridged ring system may have from 6-10 ring members, such as from 7-10 ring members. Examples of bridged ring systems include adamanty, 9-azabicyclo[3.3.1]nonan-9-yl, 8-azabicyclo[3.2.1]octanyl, bicyclo[2.2.2]octanyl, 3-azabicyclo[3.1.1]heptanyl, bicyclo [2.2.1]heptanyl, (1R,5S)-bicyclo[3.2.1]octanyl, 3-azabicyclo[3.3.1]nonanyl, and bicyclo[2.2.1]heptanyl. In some embodiments, the bridged ring system is selected from 9-azabicyclo[3.3.1]nonan-9-yl, 8-azabicyclo[3.2.1]octanyl, and bicyclo[2.2.2]octanyl.

The number of carbon atoms in a group is specified herein by the prefix "$C_{x\text{-}xx}$", wherein x and xx are integers. For example, "$C_{1\text{-}4}$alkyl" is an alkyl group which has from 1 to 4 carbon atoms; $C_{1\text{-}6}$alkoxy is an alkoxy group having from 1 to 6 carbon atoms; $C_{6\text{-}10}$aryl is an aryl group which has from 6 to 10 carbon atoms; $C_{1\text{-}4}$haloalkyl is a haloalkyl group which has from 1 to 4 carbon atoms; and N,N-di-$C_{1\text{-}6}$alkylamino is a N,N-dialkylamino group in which the nitrogen is substituted with two alkyl groups each of which is independently from 1 to 6 carbon atoms.

The disclosed compounds, or pharmaceutically acceptable salts thereof, can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The compounds, or pharmaceutically acceptable salts thereof, can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

Provided is a compound represented by formula (I):

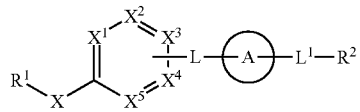

(I)

or a pharmaceutically acceptable salt thereof, wherein:
X is —O—, —S(O)$_r$—, —CH$_2$—, or —NR—, wherein r is 0, 1, or 2;
X$^1$, X$^2$, and X$^5$ are each independently CR$^7$ or N;
one of X$^3$ or X$^4$ is C and is attached by a single bond to -L-, and the other is CR$^7$ or N, provided that no more than three of X$^1$, X$^2$, X$^3$, X$^4$ or X$^5$ are N;
Ring A is monocyclic C$_{5-6}$cycloalkyl or a 5- to 6-membered monocyclic heterocyclyl comprising from 1 to 5 heteroatoms independently selected from N, S, or O; wherein Ring A is further optionally substituted with from 1 to 3 R$^4$; provided that Ring A is not morpholinyl, thiomorpholinyl or tetrahydro-2H-pyranyl;
L is a bond, —O—, —NR—, —S(O)$_n$—, —CH$_2$—, or —C(O)—, wherein n is 0, 1, or 2;
L$^1$ is an C$_{1-8}$alkylene, C$_{3-8}$cycloalkylene, —CH$_2$-L$^2$-, or a 3- to 8-membered heterocyclylene comprising 1 to 5 heteroatoms selected from N, S, or O; wherein L$^1$ may be optionally substituted with from 1 to 3 independently selected R$^5$;
L$^2$ is a divalent bridged ring system comprising 6-10 ring members, wherein the ring members may be all carbon atoms or may comprise 1 to 5 heteroatoms selected from N, S, or O;
R, for each occurrence, is independently hydrogen or C$_{1-8}$alkyl;
R$^1$ is C$_{6-20}$alkyl or a monocyclic C$_{3-8}$cycloalkyl; wherein said C$_{3-8}$cycloalkyl is substituted with at least one R$^6$ and may be optionally substituted with from 1 to 5 additional R$^6$ substituents, wherein R$^6$ for each occurrence is independently selected;
R$^2$ is —C(O)OR$^3$, —C(O)N(R$^3$)—S(O)$_2$R$^3$, —S(O)$_2$OR$^3$, —C(O)NHC(O)R$^3$, —Si(O)OH, —B(OH)$_2$, —N(R$^3$)S(O)$_2$R$^3$, —S(O)$_2$N(R$^3$)$_2$, —O—P(O)(OR$^3$)$_2$, or —P(O)(OR$^3$)$_2$, —CN, —S(O)$_2$NHC(O)R$^3$, —C(O)NHS(O)$_2$R$^3$, —C(O)NHOH, —C(O)NHCN, —CH(CF$_3$)OH, —C(CF$_3$)$_2$OH, or a heteroaryl or a heterocyclyl selected from the group consisting of formulae (a)-(i'):

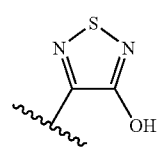

(a)

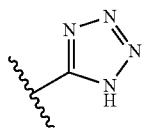

(b)

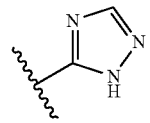

(c)

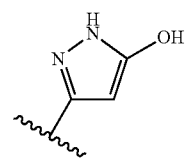

(d)

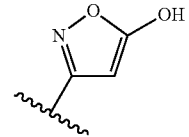

(e)

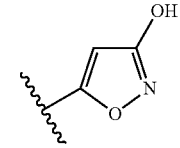

(f)

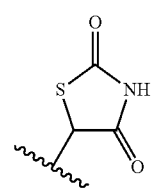

(g)

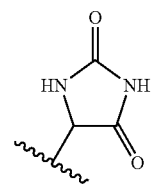

(h)

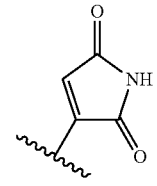

(i)

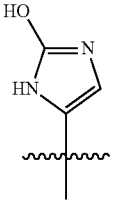

(j)

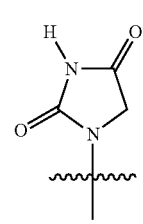

(k)

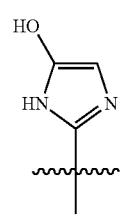 (l)
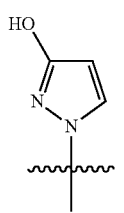 (m)
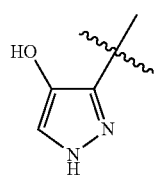 (n)
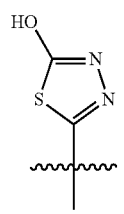 (o)
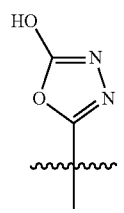 (p)
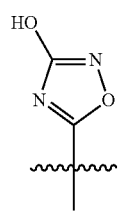 (q)
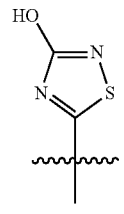 (r)
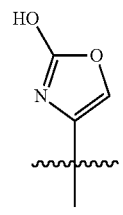 (s)
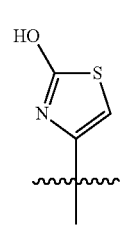 (t)
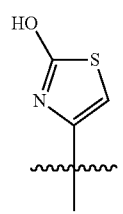 (u)
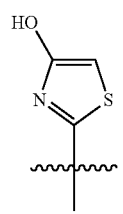 (v)
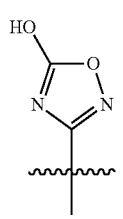 (w)
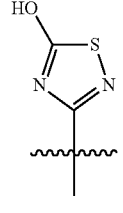 (x)
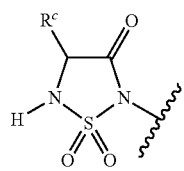 (y)
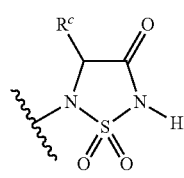 (z)

(a') 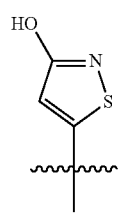

(b') 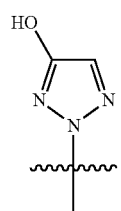

(c') 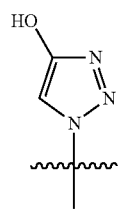

(d') 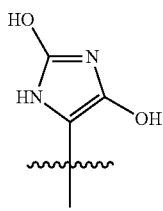

(e') 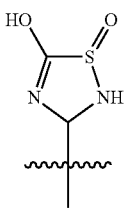

(f') 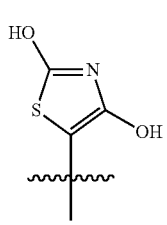

(g') 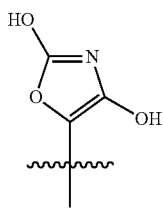

(h') 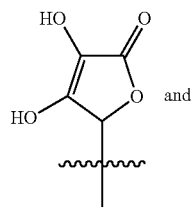

and (i') 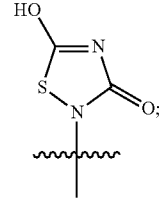

$R^3$ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 12 membered heteroaryl, and a 3 to 12 membered heterocyclyl; wherein the heteroaryl and heterocyclyl independently comprise from 1 to 6 heteroatoms selected from O, N, or S; and wherein $R^3$ may be optionally substituted with from 1 to 3 substituents independently selected from the group consisting of halo, $C_{1-4}$alkoxy, $C_{1-4}$ alkyl, cyano, nitro, hydroxyl, amino, N—$C_{1-4}$alkylamino, N,N-di-($C_{1-4}$alkyl)amino, carbamoyl, N—$C_{1-4}$alkylcarbamoyl, N,N-di-($C_{1-4}$alkyl)carbamoyl, $C_{1-4}$ alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl;

$R^4$ and $R^5$, for each occurrence, are independently halo, hydroxyl, nitro, cyano, $C_{1-8}$alkyl, $C_{1-8}$haloalkyl, $C_{1-8}$alkoxy, $C_{1-4}$haloalkoxy, $C_{2-8}$alkenyl, $C_{2-8}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_pR^a$, or —$N(R^a)S(O)_2R^b$, wherein p for each occurrence is independently 0, 1, or 2;

$R^6$, for each occurrence, is independently halo, hydroxyl, mercapto, nitro, $C_{1-8}$alkyl, $C_{1-8}$haloalkyl, $C_{1-8}$alkoxy, $C_{1-4}$haloalkoxy, $C_{1-8}$alkylthio, $C_{2-8}$alkenyl, $C_{2-8}$alkynyl, cyano, —$NR^aR^b$, $C_{3-8}$cycloalkyl, $C_{3-8}$halocycloalkyl, $C_{6-10}$aryl, 3- to 8-membered heterocyclyl, or 5- to 6-membered heteroaryl, wherein the heterocyclyl and heteroaryl comprise 1 to 4 heteroatoms independently selected from O, N, or S; or two $R^6$ on the same carbon atom together with the carbon to which they are attached form a $C_{3-8}$ spirocycloalkyl;

$R^7$, for each occurrence, is independently halo, hydroxyl, nitro, cyano, $C_{1-7}$alkyl, $C_{1-7}$haloalkyl, $C_{1-7}$alkoxy, $C_{1-4}$haloalkoxy, $C_{2-7}$alkenyl, $C_{2-7}$alkynyl, $C_{3-8}$cycloalkyl, $C_{3-8}$halocycloalkyl, $C_{3-8}$cycloalkoxy, $C_{3-8}$halocycloalkoxy, —$NR^cR^d$, —$C(O)NR^cR^d$, —$N(R^c)C(O)R^b$, —$C(O)R^a$, —$S(O)_pR^a$, and —$N(R^c)S(O)_2R^b$, wherein p is 0, 1, or 2; and $R^a$ and $R^b$, for each occurrence, are independently hydrogen, $C_{1-8}$alkyl, $C_{2-8}$alkenyl, $C_{2-8}$alkynyl, $C_{3-8}$cycloalkyl, $C_{6-10}$aryl, or $C_{3-8}$halocycloalkyl, provided that the compound is not

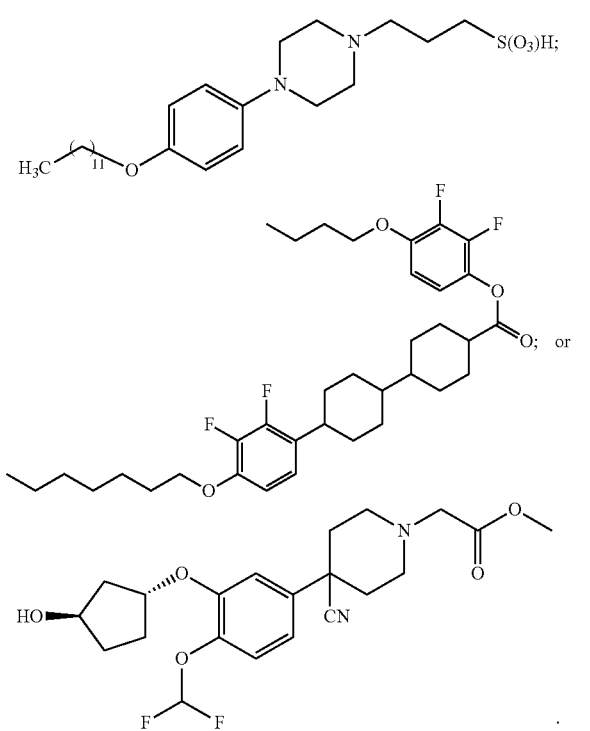

In some embodiments, provided is a compound represented by formula (I):

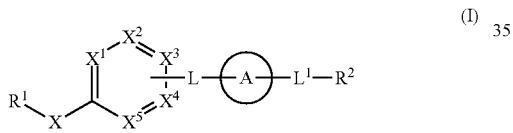

or a pharmaceutically acceptable salt thereof, wherein:
X is —O—, —S(O)$_r$—, or —NR—, wherein r is 0, 1, or 2;
$X^1$, $X^2$, and $X^5$ are each independently CH or N;
one of $X^3$ or $X^4$ is C and is attached by a single bond to -L-, and the other is CH or N, provided that no more than three of $X^1$, $X^2$, $X^3$, $X^4$ or $X^5$ are N;
Ring A is monocyclic C$_{5-6}$cycloalkyl or a 5- to 6-membered monocyclic heterocyclyl comprising from 1 to 5 heteroatoms independently selected from N, S, or O; wherein Ring A is further optionally substituted with from 1 to 3 R$^4$; provided that Ring A is not morpholinyl, thiomorpholinyl or tetrahydro-2H-pyranyl;
L is a bond, —O—, —NR—, —S(O)$_n$—, —CH$_2$—, or —C(O)—, wherein n is 0, 1, or 2;
L$^1$ is an C$_{1-8}$alkylene, C$_{3-8}$cycloalkylene, —CH$_2$-L$^2$-, or a 3- to 8-membered heterocyclylene comprising 1 to 5 heteroatoms selected from N, S, or O; wherein L$^1$ may be optionally substituted with from 1 to 3 independently selected R$^5$;
L$^2$ is a divalent bridged ring system comprising 6-10 ring members, wherein the ring members may be all carbon atoms or may comprise 1 to 5 heteroatoms selected from N, S, or O;
R, for each occurrence, is independently hydrogen or C$_{1-8}$alkyl;

R$^1$ is C$_{6-20}$alkyl or a monocyclic C$_{3-8}$cycloalkyl; wherein said C$_{3-8}$cycloalkyl is substituted with at least one R$^6$ and may be optionally substituted with from 1 to 5 additional R$^6$ substituents, wherein R$^6$ for each occurrence is independently selected;
R$^2$ is —C(O)OR$^3$, —C(O)N(R$^3$)—S(O)$_2$R$^3$, —S(O)$_2$OR$^3$, —C(O)NHC(O)R$^3$, —Si(O)OH, —B(OH)$_2$, —N(R$^3$)S(O)$_2$R$^3$, —S(O)$_2$N(R$^3$)$_2$, —O—P(O)(OR$^3$)$_2$, or —P(O)(OR$^3$)$_2$, —CN, —S(O)$_2$NHC(O)R$^3$, —C(O)NHS(O)$_2$R$^3$, —C(O)NHOH, —C(O)NHCN, —CH(CF$_3$)OH, —C(CF$_3$)$_2$OH, or a heteroaryl or a heterocyclyl selected from the group consisting of formulae (a)-(i'):

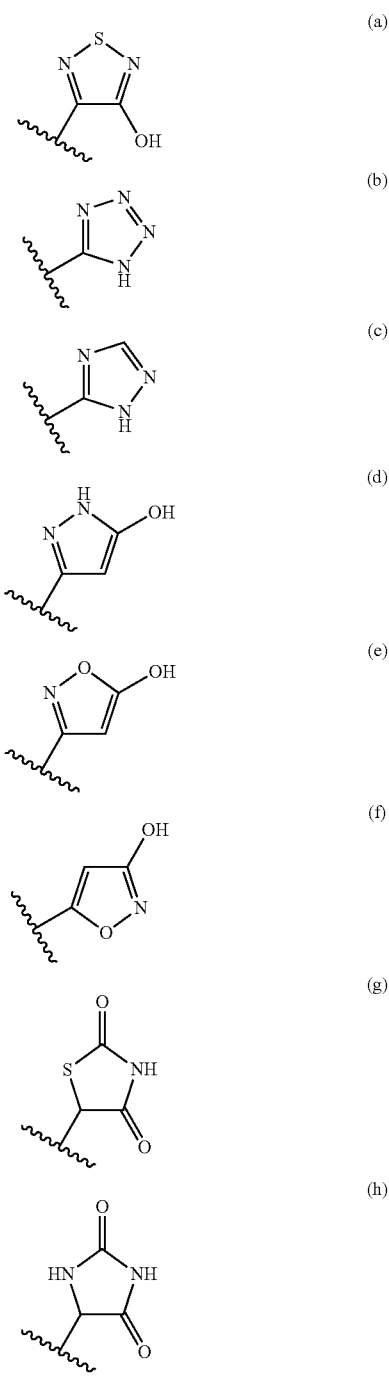

-continued
(i) 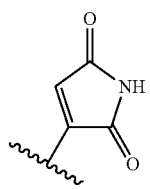
(j) 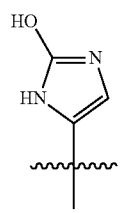
(k) 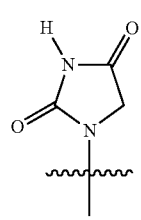
(l) 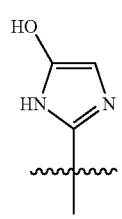
(m) 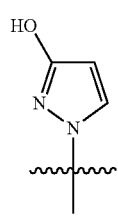
(n) 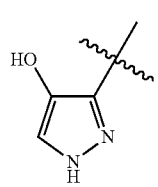
(o) 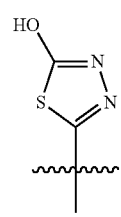
-continued
(p) 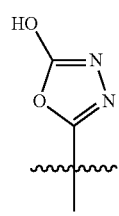
(q) 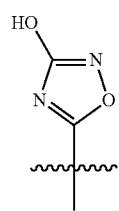
(r) 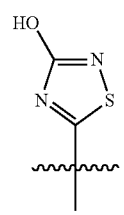
(s) 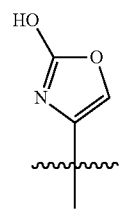
(t) 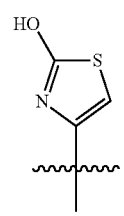
(u) 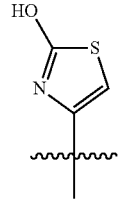
(v) 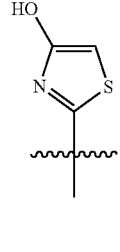

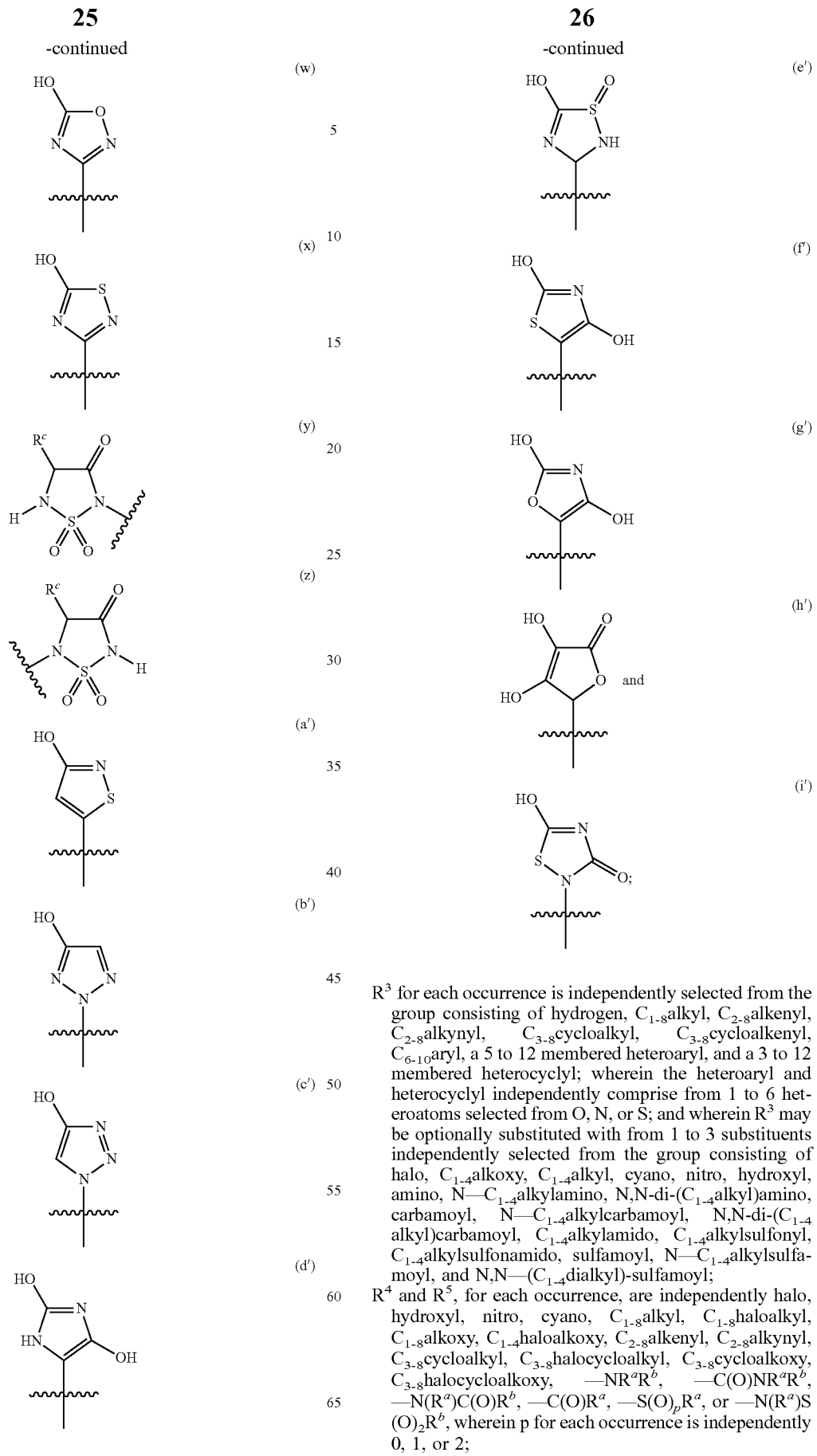

$R^3$ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 12 membered heteroaryl, and a 3 to 12 membered heterocyclyl; wherein the heteroaryl and heterocyclyl independently comprise from 1 to 6 heteroatoms selected from O, N, or S; and wherein $R^3$ may be optionally substituted with from 1 to 3 substituents independently selected from the group consisting of halo, $C_{1-4}$alkoxy, $C_{1-4}$alkyl, cyano, nitro, hydroxyl, amino, N—$C_{1-4}$alkylamino, N,N-di-($C_{1-4}$alkyl)amino, carbamoyl, N—$C_{1-4}$alkylcarbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl;

$R^4$ and $R^5$, for each occurrence, are independently halo, hydroxyl, nitro, cyano, $C_{1-8}$alkyl, $C_{1-8}$haloalkyl, $C_{1-8}$alkoxy, $C_{1-4}$haloalkoxy, $C_{2-8}$alkenyl, $C_{2-8}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_pR^a$, or —$N(R^a)S(O)_2R^b$, wherein p for each occurrence is independently 0, 1, or 2;

$R^6$, for each occurrence, is independently halo, hydroxyl, mercapto, nitro, $C_{1-8}$alkyl, $C_{1-8}$haloalkyl, $C_{1-8}$alkoxy, $C_{1-4}$haloalkoxy, $C_{1-8}$alkylthio, $C_{2-8}$alkenyl, $C_{2-8}$alkynyl, cyano, —$NR^aR^b$, $C_{3-8}$cycloalkyl, $C_{3-8}$halocycloalkyl, $C_{6-m}$aryl, 3- to 8-membered heterocyclyl, or 5- to 6-membered heteroaryl, wherein the heterocyclyl and heteroaryl comprise 1 to 4 heteroatoms independently selected from O, N, or S; or two $R^6$ on the same carbon atom together with the carbon to which they are attached form a $C_{3-8}$spirocycloalkyl; and $R^a$ and $R^b$, for each occurrence, are independently hydrogen, $C_{1-8}$alkyl, $C_{2-8}$alkenyl, $C_{2-8}$alkynyl, $C_{3-8}$cycloalkyl, $C_{6-10}$aryl, or $C_{3-8}$halocycloalkyl, provided that the compound is not

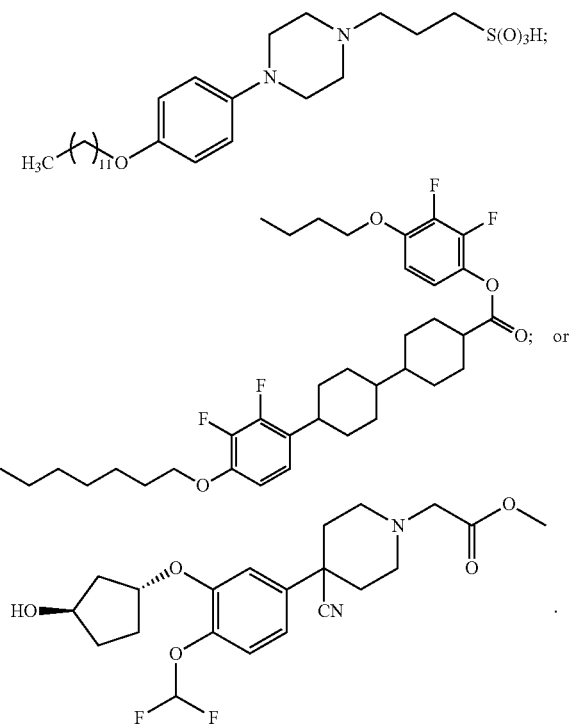

In some embodiments, X is —O—.

In some embodiments, Ring A is monocyclic $C_{5-6}$cycloalkyl.

In some embodiments, Ring A is 5- to 6-membered monocyclic heterocyclyl comprising from 1 to 5 heteroatoms independently selected from N, S, or O.

In some embodiments, Ring A is 5- to 6-membered monocyclic heterocyclyl comprising from 1 to 2 heteroatoms independently selected from N.

In some embodiments, L is a bond, or —NR—.

In some embodiments, L is a bond.

In some embodiments, $L^1$ is an $C_{1-8}$alkylene, $C_{3-8}$cycloalkylene, —$CH_2$-$L^2$-, or a 3- to 8-membered heterocyclylene comprising 1 to 5 N.

In some embodiments, $L^1$ is $C_{1-8}$alkylene.

In some embodiments, $L^2$ is a divalent bridged ring system comprising 6-10 ring members, wherein the ring members are all carbon atoms.

In some embodiments, R, for each occurrence, is hydrogen.

In some embodiments, $R^1$ is $C_{6-20}$alkyl.

In some embodiments, $R^1$ is monocyclic $C_{3-8}$cycloalkyl; wherein said $C_{3-8}$cycloalkyl is substituted with at least one $R^6$ and may be optionally substituted with from 1 to 5 additional $R^6$ substituents, wherein $R^6$ for each occurrence is independently selected; and $R^6$, for each occurrence, is independently $C_{1-8}$alkyl; or two $R^6$ on the same carbon atom together with the carbon to which they are attached form a $C_{3-8}$spirocycloalkyl.

In some embodiments, $R^2$ is —C(O)$OR^3$.

In some embodiments, $R^2$ is —C(O)$OR^3$, and $R^3$ is hydrogen.

In some embodiments, each $R^7$ is hydrogen.

In some embodiments, X is —O—, —S(O)$_r$—, or —NR—, wherein r is 0, 1, or 2.

In some embodiments, X is —O—.

In some embodiments, X is —O—;

$X^1$, $X^2$, and $X^5$ are each independently CH or N;

one of $X^3$ or $X^4$ is C and is attached by a single bond to -L-, and the other is CH or N, provided that no more than three of $X^1$, $X^2$, $X^3$, $X^4$ or $X^5$ are N;

Ring A is an unsubstituted monocyclic $C_{5-6}$cycloalkyl or a 5- to 6-membered monocyclic heterocyclyl comprising from 1 to 5 heteroatoms independently selected from N, S, or O; provided that Ring A is not morpholinyl, thiomorpholinyl or tetrahydro-2H-pyranyl;

L is a bond, or —NR—;

$L^1$ is an $C_{1-8}$alkylene, $C_{3-8}$cycloalkylene, —$CH_2$-$L^2$-, or a 3- to 8-membered heterocyclylene comprising 1 to 5 N;

$L^2$ is a divalent bridged ring system comprising 6-10 ring members, wherein the ring members are all carbon atoms;

R, for each occurrence, is hydrogen;

$R^1$ is $C_{6-20}$alkyl or a monocyclic $C_{3-8}$cycloalkyl; wherein said $C_{3-8}$cycloalkyl is substituted with at least one $R^6$ and may be optionally substituted with from 1 to 5 additional $R^6$ substituents, wherein $R^6$ for each occurrence is independently selected;

$R^2$ is —C(O)$OR^3$, —C(O)N($R^3$)—S(O)$_2R^3$, —S(O)$_2OR^3$, —C(O)NHC(O)$R^3$, —Si(O)OH, —B(OH)$_2$, —N($R^3$)S(O)$_2R^3$, —S(O)$_2$N($R^3$)$_2$, —O—P(O)(O$R^3$)$_2$, or —P(O)(O$R^3$)$_2$, —CN, —S(O)$_2$NHC(O)$R^3$, —C(O)NHS(O)$_2R^3$, —C(O)NHOH, —C(O)NHCN, —CH(CF$_3$)OH, —C(CF$_3$)$_2$OH, or a heteroaryl or a heterocyclyl selected from the group consisting of formulae (a)-(i'):

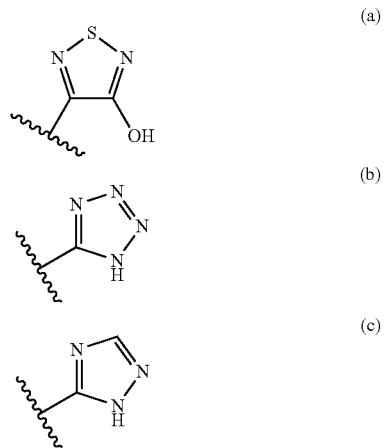

-continued
(d) 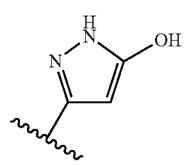
(e) 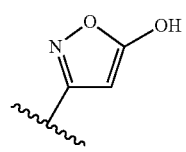
(f) 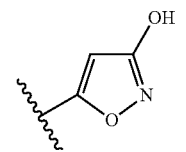
(g) 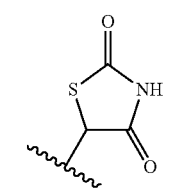
(h) 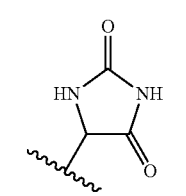
(i) 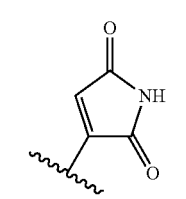
(j) 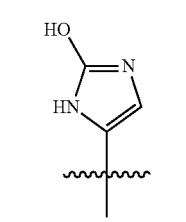
(k) 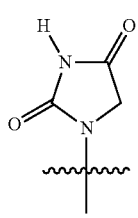
-continued
(l) 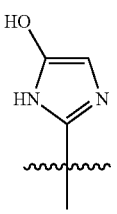
(m) 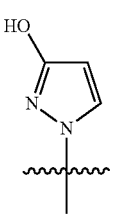
(n) 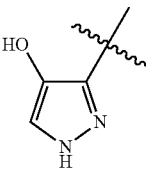
(o) 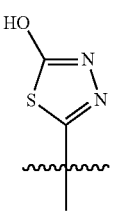
(p) 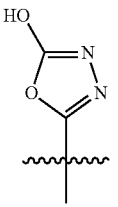
(q) 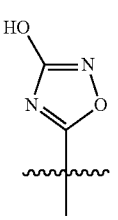
(r) 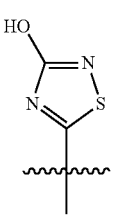

-continued
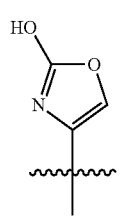 (s)
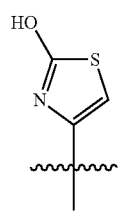 (t)
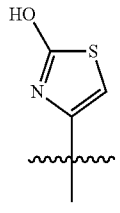 (u)
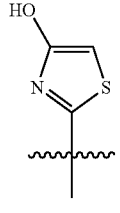 (v)
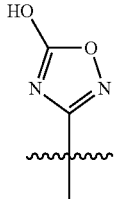 (w)
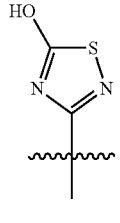 (x)
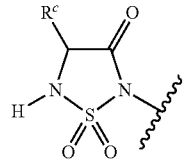 (y)
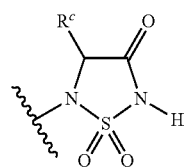 (z)
-continued
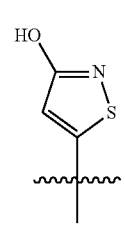 (a')
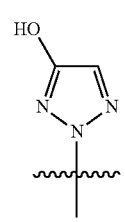 (b')
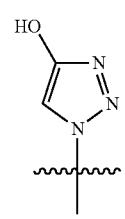 (c')
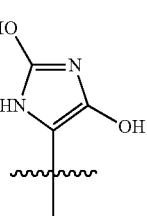 (d')
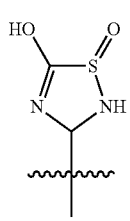 (e')
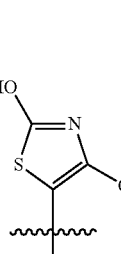 (f')
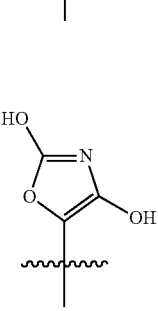 (g')

-continued (h')

[Structure showing a furanone with HO groups]

(i')

[Structure showing an isothiazolone with HO group]

R³ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 12 membered heteroaryl, and a 3 to 12 membered heterocyclyl; wherein the heteroaryl and heterocyclyl independently comprise from 1 to 6 heteroatoms selected from O, N, or S; and wherein R³ may be optionally substituted with from 1 to 3 substituents independently selected from the group consisting of halo, $C_{1-4}$alkoxy, $C_{1-4}$alkyl, cyano, nitro, hydroxyl, amino, N—$C_{1-4}$alkylamino, N,N-di-($C_{1-4}$alkyl)amino, carbamoyl, N—$C_{1-4}$alkylcarbamoyl, N,N-di-($C_{1-4}$ alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl; and R⁶, for each occurrence, is independently $C_{1-8}$alkyl; or two R⁶ on the same carbon atom together with the carbon to which they are attached form a $C_{3-8}$spirocycloalkyl.

Also provided is a compound selected from: 3-(4-(4-((trans-4-(tert-Butyl)cyclohexyl)oxy)phenyl)piperazin-1-yl) propanoic acid; 4-(4-(4-((trans-4-(tert-Butyl)cyclohexyl) oxy)phenyl)piperazin-1-yl)butanoic acid; 3-(3-(4-(trans-4-tert-Butylcyclohexyloxy)phenyl)piperidin-1-yl)propanoic acid; 4-(3-(4-(cis-4-tert-Butylcyclohexyloxy)phenyl)piperidin-1-yl)butanoic acid; 3-(3-(4-(Octyloxy)phenyl)piperidin-1-yl)propanoic acid; 4-(3-(4-(Octyloxy)phenyl)piperidin-1-yl)butanoic acid; 3-(4-(4-(Octyloxy)phenyl)piperazin-1-yl) propanoic acid; 4-(4-(4-(Octyloxy)phenyl)piperazin-1-yl) butanoic acid; 4-((4-(4-(Octyloxy)phenyl)piperazin-1-yl) methyl)bicyclo[2.2.2]octane-1-carboxylic acid; 4-((4-(4-((trans-4-(tert-Butyl)cyclohexyl)oxy)phenyl)piperazin-1-yl) methyl)bicyclo[2.2.2]octane-1-carboxylic acid; 1-(3-(4-(trans-4-tert-butylcyclohexyloxy)phenyl)cyclohexyl) piperidine-4-carboxylic acid; 3-(3-(5-(Octyloxy)pyridin-2-ylamino)piperidin-1-yl)propanoic acid; 3-(3-(5-(trans-4-tert-butylcyclohexyloxy)pyridin-2-ylamino)piperidin-1-yl) propanoic acid; 3-(3-((4-((trans-4-(tert-Butyl)cyclohexyl) oxy)phenyl)amino)piperidin-1-yl)propanoic acid; 3-(3-(4-((trans-4-(tert-Butyl)cyclohexyl)oxy)phenyl)pyrrolidin-1-yl)propanoic acid; 1-(3-(4-(octyloxy)phenyl)cyclohexyl) piperidine-4-carboxylic acid; 4-(3-(4-((trans-4-(tert-Butyl) cyclohexyl)oxy)phenyl)pyrrolidin-1-yl)butanoic acid; 3-(3-(3-((trans-4-(tert-Butyl)cyclohexyl)oxy)phenyl)piperidin-1-yl)propanoic acid; 4-(3-(3-((trans-4-(tert-Butyl)cyclohexyl) oxy)phenyl)piperidin-1-yl)butanoic acid; 4-(3-((trans-4-(tert-Butyl)cyclohexyl)oxy)phenyl)piperidin-1-yl) cyclohexanecarboxylic acid; 4-(3-(4-(Octyloxy)phenyl) piperidin-1-yl)cyclohexanecarboxylic acid; 3-(4-(6-(Octyloxy)pyridazin-3-yl)piperazin-1-yl)propanoic acid; 3-(4-(5-(Octyloxy)pyrimidin-2-yl)piperazin-1-yl)propanoic acid; 3-(4-(5-(Octyloxy)pyridin-2-yl)piperazin-1-yl)propanoic acid; 4-(4-(4-((trans-4-(tert-Butyl)cyclohexyl)oxy) phenyl)piperidin-1-yl)butanoic acid; 3-(4-(4-((cis-4-Ethylcyclohexyl)oxy)phenyl)piperidin-1-yl)propanoic acid; 3-(4-(4-((trans-4-(tert-Butyl)cyclohexyl)oxy)phenyl)piperidin-1-yl)propanoic acid; 5-(4-(4-((trans-4-Ethylcyclohexyl)oxy) phenyl)piperidin-1-yl)pentanoic acid; 4-(4-(4-((trans-4-Ethylcyclohexyl)oxy)phenyl)piperidin-1-yl)butanoic acid; 3-(4-(4-((trans-4-ethylcyclohexyl)oxy)phenyl)piperidin-1-yl)propanoic acid; 5-(4-(4-((cis-4-Ethylcyclohexyl)oxy) phenyl)piperidin-1-yl)pentanoic acid; 3-(4-(4-(Spiro[4.5] decan-8-yloxy)phenyl)piperidin-1-yl)propanoic acid; 5-(4-(4-(Spiro[4.5]decan-8-yloxy)phenyl)piperidin-1-yl) pentanoic acid; 5-(4-(4-((trans-4-(tert-Butyl)cyclohexyl) oxy)phenyl)piperidin-1-yl)pentanoic acid; 4-(4-(4-(Spiro [4.5]decan-8-yloxy)phenyl)piperidin-1-yl)butanoic acid; 4-(4-(4-((cis-4-Ethylcyclohexyl)oxy)phenyl)piperidin-1-yl) butanoic acid; 4-(4-(4-((trans-4-(tert-Butyl)cyclohexyl)oxy) phenyl)-5,6-dihydropyridin-1(2H)-yl)butanoic acid; 3-(4-(4-((trans-4-(tert-Butyl)cyclohexyl)oxy)phenyl)-5,6-dihydropyridin-1(2H)-yl)propanoic acid; 3-(4-(4-((cis-4-Ethylcyclohexyl)oxy)phenyl)-5,6-dihydropyridin-1(2H)-yl) propanoic acid; 3-(4-(4-(Spiro[4.5]decan-8-yloxy)phenyl)-5,6-dihydropyridin-1(2H)-yl)propanoic acid; 4-(4-(4-((cis-4-Ethylcyclohexyl)oxy)phenyl)-5,6-dihydropyridin-1(2H)-yl)butanoic acid; 5-(4-(4-((cis-4-Ethylcyclohexyl)oxy) phenyl)-5,6-dihydropyridin-1(2H)-yl)pentanoic acid; 5-(4-(4-((trans-4-Ethylcyclohexyl)oxy)phenyl)-5,6-dihydropyridin-1(2H)-yl)pentanoic acid; 4-(4-(4-((trans-4-Ethylcyclohexyl)oxy)phenyl)-5,6-dihydropyridin-1(2H)-yl) butanoic acid; 3-(4-(4-((trans-4-Ethylcyclohexyl)oxy) phenyl)-5,6-dihydropyridin-1(2H)-yl)propanoic acid; 5-(4-(4-((trans-4-(tert-Butyl)cyclohexyl)oxy)phenyl)-5,6-dihydropyridin-1(2H)-yl)pentanoic acid; 4-(4-(4-(Spiro[4.5] decan-8-yloxy)phenyl)-5,6-dihydropyridin-1(2H)-yl) butanoic acid; 5-(4-(4-(Spiro[4.5]decan-8-yloxy)phenyl)-5, 6-dihydropyridin-1(2H)-yl)pentanoic acid; 3-(3-(3-(Octyloxy)phenyl)piperidin-1-yl)propanoic acid; and 4-(3-(3-(Octyloxy)phenyl)piperidin-1-yl)butanoic acid, or a pharmaceutically acceptable salt thereof.

In cases where a compound of formula (I) is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl)amines, tri(substituted alkyl)amines, alkenyl amines, dialkenyl amines, trialkenyl amines, substituted alkenyl amines, di(substituted alkenyl)amines, tri(substituted alkenyl)amines, cycloalkyl amines, di(cycloalkyl)amines, tri(cycloalkyl)amines, substituted cycloalkyl amines, disubstituted cycloalkyl amine, trisubstituted cycloalkyl amines, cycloalkenyl amines, di(cycloalkenyl)amines, tri(cycloalkenyl)amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included are amines where the two or three substituents, together with the amino nitrogen, form a heterocyclic or heteroaryl group. Non-limiting examples of amines can include, isopropylamine, trimethyl amine, diethyl amine, tri(iso-propyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

A compound of formula (I), or a pharmaceutically acceptable salt thereof, can modulate the activity of S1P receptors. A compound of formula (I), or a pharmaceutically acceptable salt thereof, can have S1P receptor agonist or antagonist activity. The compound, or a pharmaceutically acceptable salt thereof, can be selective for the S1P4 receptor. The compound, or a pharmaceutically acceptable salt thereof, can be a selective S1P4 antagonist. Being selective can mean that the compound, or a pharmaceutically acceptable salt thereof, binds to the receptor (or relatively small group of related molecules or proteins) in a complex mixture, or in other words, when exposed to a variety of closely related receptor types, the compound, or a pharmaceutically acceptable salt thereof, can bind preferentially to just one of the receptor types.

The compound, or a pharmaceutically acceptable salt thereof, can have a greater affinity for the S1P4 receptor, by at by at least 100-fold, by at least 50-fold, by at least 10-fold, by at least 5-fold or by at least 2-fold, than for S1P1 receptor, S1P2 receptor, S1P3 receptor, or S1P5 receptor.

An inhibitor of S1P4 mediated activity can block S1P interaction with an S1P4 receptor. For example, the inhibitor can be an antagonist of an S1P4 receptor. An antagonist can be a molecule that has affinity for the receptor but does not induce activity or a specific activity from the receptor. The antagonist can bind with an S1P4 receptor with an $IC_{50}$ value of less than 1 µM, less than 750 nM, less than 500 nM, less than 250 nM or less than 100 nM. The antagonist can bind with an S1P4 receptor with an $IC_{50}$ value in a range between 1 nM and 1 µM, between 1 nM and 500 nM, between 10 nM and 250 nM, between 25 nm and 100 nM, or between 50 nM and 100 nM.

The compound, or a pharmaceutically acceptable salt thereof, can also promote oligodendrocyte progenitor cell differentiation. The compound, or a pharmaceutically acceptable salt thereof, can promote myelination or remyelination.

An "S1P modulating agent" refers a compound, or a pharmaceutically acceptable salt thereof, or composition that is capable of inducing a detectable change in S1P receptor activity in vivo or in vitro (e.g., at least 10% increase or decrease in S1P activity as measured by a given assay such as the assays described in the examples and known in the art. "S1P receptor," refers to all of the S1P receptor subtypes (for example, the S1P receptors S1P1, S1P2, S1P3, S1P4, or S1P5), unless the specific subtype is indicated. It is well known in the art how to determine S1P agonist or antagonist activity using the standard tests described herein, or using other similar tests which are well known in the art. In some cases, depending on the cell type and conditions used, an S1P modulating agent can have agonist or antagonist activity, even at the same receptor subtype.

The biological effects of an S1P modulating agent vary depending on whether the compound, or a pharmaceutically acceptable salt thereof, has S1P receptor agonist or antagonist activity. Potential uses of an S1P modulating agent include, but are not limited to, prevention or treatment of a pathological condition or symptom in a mammal. For example, the condition can include asthma, an inflammatory neuropathies, arthritis, lupus erythematosis, psoriasis, an ischemia reperfusion injury, a solid tumor, a tumor metastasis, a disease associated with angiogenesis, a vascular disease, a pain condition, an acute viral disease, or insulin-dependent diabetes, and non-insulin dependent diabetes. The condition can alter lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, chronic inflammatory disorders, inflammatory bowel diseases (e.g., Crohn's disease and ulcerative colitis), multiple sclerosis, and in drug-eluting stents. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety. A class of S1P receptor agonists are described in provisional U.S. Application No. 60/956,111, filed Aug. 15, 2007, and PCT/US2008/073378, filed Aug. 15, 2008, each of which is incorporated by reference in its entirety. See also provisional U.S. Application No. 61/231,539, filed Aug. 5, 2009, and PCT/US2010/44607, filed Aug. 5, 2010, each of which is incorporated by reference in its entirety. See also provisional U.S. Application No. 61/440,254, filed Feb. 7, 2011, and PCT/US2012/23799 filed Feb. 6, 2012, each of which is incorporated by reference in its entirety.

Additional potential uses of an S1P modulating agent include, but are not limited to, prevention or treatment of a pathological condition or symptom in a mammal. For example, the condition can include inhibited cell migration of oligodendrocyte precursor cells (OPCs).

Potential uses of an S1P receptor antagonist, and S1P4 receptor type selective antagonists particularly, include, but are not limited to, prevention or treatment of a pathological condition or symptom in a mammal.

LPA has been shown to be involved in lymphocyte trafficking and helps promote entry of lymphocytes into secondary lymphoid organs (see Kanda, et al., Nat. Immunology (2008), 9:415-423). Therefore, the disclosed compounds and salts thereof are expected to be useful for altering lymphocyte trafficking as a method for prolonging allograft survival, for example transplantation including solid organ transplants, treatment of graft vs. host disease, bone marrow transplantation, and the like.

An "ATX modulating agent" refers a compound, or a pharmaceutically acceptable salt thereof, or composition that is capable of inducing a detectable change in ATX activity in vivo or in vitro (e.g., at least 10% increase or decrease in ATX activity as measured by a given assay such as the assays described in the examples and known in the art. The compound, or a pharmaceutically acceptable salt thereof, be an ATX modulating agent, i.e., it can modulate the activity of ATX. For example, the compound, or a pharmaceutically acceptable salt thereof, can be an ATX inhibitor. The compound, or a pharmaceutically acceptable salt thereof, can be a selective ATX modulating agent. Being selective can mean that the compound, or a pharmaceutically acceptable salt thereof, binds to ATX preferentially when exposed to a variety of potential binding partners. The compound, or a pharmaceutically acceptable salt thereof, can have a greater affinity for the ATX, by at by at least 100-fold, by at least 50-fold, by at least 10-fold, by at least 5-fold or by at least 2-fold, than for other binding partners. Affinity can be measured, for example, as a dissociation constant ($K_d$), as an inhibition constant (such as $IC_{50}$), or another measure; provided that affinity is measured in a consistent fashion between ATX and the other binding partners it is compared to.

An inhibitor of ATX mediated activity can block interaction of ATX with its native substrate(s), such as LPC. For example, the inhibitor can show an $IC_{50}$ value of less than 1 µM, less than 750 nM, less than 500 nM, less than 250 nM, less than 100 nM, less than 50 nM, less than 25 nM, or less than 10 nM, when measured in a FRET-based assay using FS-3 substrate (see, e.g., Ferguson, C. G., et al., Org Lett. 2006 May 11; 8(10): 2023-2026, which is incorporated by reference in its entirety).

Some substrates and inhibitors of ATX are described in WO 2011/151461, which is incorporated by reference in its entirety.

Potential uses of an ATX modulating agent include, but are not limited to, prevention or treatment of a pathological condition or symptom in a mammal. The pathological disorder can be an inflammatory disorder, an autoimmune disorder, a fibrosis of the lung, or a malignancy of the lung. Prevention or treatment of the pathological condition or symptom can include administering to the mammal an effective amount of an ATX modulating agent, e.g., an ATX inhibitor, to prevent, treat or reduce symptoms of the inflammatory disorder, autoimmune disorder, the fibrosis of the lung, or the malignancy of the lung. In one embodiment, the inflammatory disorder is rheumatoid arthritis (RA). In another embodiment, the autoimmune disorder is multiple sclerosis (MS). A particular example of lung fibrosis is an interstitial lung disease, for instance, pulmonary fibrosis. See, for example, WO 2011/151461, which is incorporated by reference in its entirety.

In some embodiments, an ATX inhibitor of the present invention can be used to treat or prevent a demyelinating disease or disorder. Demyelinating diseases or disorders include multiple sclerosis, Guillain-Barre Syndrome, chronic inflammatory demyelinating polyneuropathy (CIDP), transverse myelitis, and optic neuritis, spinal cord injury, stroke or other ischemia, cerebral palsy, Charcot-Marie-Tooth disease (CMT), Sjogren-Larsson syndrome, Refsum disease, Krabbe disease, Canavan disease, Alexander disease, nerve damage due to pernicious anemia, progressive multifocal leukoencephalopathy (PML), Lyme disease, tabes dorsalis due to untreated syphilis, demyelination due to exposure to an organophosphates, demyelination due to vitamin B12 deficiency or copper deficiency.

In addition, disclosed compounds and salts can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds and salts can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds and salts may be useful as anti-inflammatory agents. This inhibition could be in concert with S1P receptor activity, or be independent of activity at any S1P receptor.

In addition, disclosed compounds and salts may be useful for inhibition of the multiple substrate lipid kinase (MuLK). MuLK is highly expressed in many human tumor cells and thus its inhibition might slow the growth or spread of tumors.

Neurological Disorders

MS can begin with a relapsing-remitting pattern of neurologic involvement, which then can progress to a chronic phase with increasing neurological damage. MS can be associated with the destruction of myelin, oligodendrocytes or axons localized to chronic lesions. The demyelination observed in MS may not always permanent and remyelination has been documented in early stages of the disease. Remyelination of neurons can require oligodendrocytes.

The distal tip of an extending axon or neurite can include a specialized region, known as the growth cone. Growth cones can sense the local environment and can guide axonal growth toward a neuron's target cell. Growth cones can respond to environmental cues, for example, surface adhesiveness, growth factors, neurotransmitters and electric fields. The growth cones can advance at a rate of one to two millimeters per day. The growth cone can explore the area ahead of it and on either side, by means of elongations classified as lamellipodia and filopodia. When an elongation contacts an unfavorable surface, it can withdraw. When an elongation contacts a favorable growth surface, it can continue to extend and guides the growth cone in that direction. When the growth cone reaches an appropriate target cell a synaptic connection can be created.

Nerve cell function can be influenced by contact between neurons and other cells in their immediate environment (Rutishauser, et al., 1988, *Physiol. Rev.* 68:819, which is incorporated by reference in its entirety). These cells can include specialized glial cells, oligodendrocytes in the central nervous system (CNS), and Schwann cells in the peripheral nervous system (PNS), which can sheathe the neuronal axon with myelin (Lemke, 1992, in *An Introduction to Molecular Neurobiology*, Z. Hall, Ed., p. 281, Sinauer, each of which is incorporated by reference in its entirety). LPA causes the collapse of the neuron growth cone and tends to inhibit or reverse the morphological differentiation of many neuronal cell lines (see Gendaszewska-Darmach, Acta Biochimica Polonica (2008), 55(2):227-240). Since ATX activity is involved in the generation of LPA, inhibitors of ATX should increase the ability of the nervous system to make synaptic connections. Thus, ATX inhibitors may be useful in treating neurodegenerative disorders such as Alzheimer's disease, Huntington's disease, Parkinson's disease (including Parkinson's dementia), Lewy Body Dementia, amylotrophic lateral sclerosis (ALS), Friedreich's ataxia, spinal muscular atrophy.

CNS neurons can have the inherent potential to regenerate after injury, but they can be inhibited from doing so by inhibitory proteins present in myelin (Brittis et al., 2001, Neuron 30:11-14; Jones et al., 2002, J. Neurosci. 22:2792-2803; Grimpe et al., 2002, J. Neurosci.: 22:3144-3160, each of which is incorporated by reference in its entirety).

Several myelin inhibitory proteins found on oligodendrocytes have been characterized. Known examples of myelin inhibitory proteins can include NogoA (Chen et al., Nature, 2000, 403, 434-439; Grandpre et al., Nature 2000, 403, 439-444, each of which is incorporated by reference in its entirety), myelin associated glycoprotein (MAG) (McKerracher et al., 1994, Neuron 13:805-811; Mukhopadhyay et al., 1994, Neuron 13:757-767, each of which is incorporated by reference in its entirety) or oligodendrocyte glycoprotein (OM-gp), Mikol et al., 1988, J. Cell. Biol. 106:1273-1279, each of which is incorporated by reference in its entirety). Each of these proteins can be a ligand for the neuronal Nogo receptor-1 (NgR1 (Wang et al., Nature 2002, 417, 941-944; Grandpre et al., Nature 2000, 403, 439-444; Chen et al., Nature, 2000, 403, 434-439; Domeniconi et al., Neuron 2002, published online Jun. 28, 2002, each of which is incorporated by reference in its entirety).

Nogo receptor-1 (NgR1) is a GPI-anchored membrane protein that contains 8 leucine rich repeats (Fournier et al., 2001, Nature 409:341-346, which is incorporated by reference in its entirety). Upon interaction with inhibitory proteins (e.g., NogoA, MAG and OM-gp), the NgR1 complex can transduce signals that lead to growth cone collapse and inhibition of neurite outgrowth.

There is a need for molecules and methods for inhibiting NgR1-mediated growth cone collapse and the resulting inhibition of neurite outgrowth. Additionally, there is a need for molecules which increase neuronal survival and axon regeneration, particularly for the treatment of disease, disorders or injuries that involve axonal injury, neuronal or oligodendrocyte cell death, demyelination or dymyelination or generally relate to the nervous system.

Such diseases, disorders or injuries can include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, or Bell's palsy. Among these diseases, MS may the most widespread, affecting approximately 2.5 million people worldwide.

Various disease-modifying treatments may be available for MS, including the use of corticosteroids and immunomodulating agents such as interferon beta or Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., N. Engl. J. Med. 346: 165-73 (2002), each of which is incorporated by reference in its entirety. However, there remains an urgent need to devise additional therapies for MS and other demyelination and dismyelination disorders.

A compound of formula (I), or a pharmaceutically acceptable salt thereof, can promote myelination or remyelination. A method can include administering a compound of formula (I), or a pharmaceutically acceptable salt thereof, to cells. A method of promoting oligodendrocyte progenitor cell differentiation can include administering a compound of formula (I), or a pharmaceutically acceptable salt thereof, to cells. A method of treating multiple sclerosis can include administering a compound of formula (I), or a pharmaceutically acceptable salt thereof, to a subject.

A number of studies have shown that ATX is expressed in non-pathological conditions, throughout development, with high expression levels in the CNS among other tissues. ATX mRNA was identified as highly upregulated during oligodendrocyte differentiation and ATX protein expression is also apparent in maturing ODCs, temporally correlated with the process of myelination. Finally, in the adult brain ATX is expressed in secretory epithelial cells, such as the choroid plexus, ciliary, iris pigment, and retinal pigment epithelial cells, whereas there is evidence for ATX expression in leptomenigneal cells and cells of the CNS vasculature. See, for example, Fuss, B., et al., J Neurosci 17, 9095-9103 (1997); Kawagoe, H., et al. Genomics 30, 380-384 (1995); Lee, H. Y., et al. J Biol Chem 271, 24408-24412 (1996); Narita, M., et al., J Biol Chem 269, 28235-28242 (1994); Bachner, D., et al., Mechanisms of Development 84, 121-125 (1999); Awatramani, R., et al., Nat Genet 35, 70-75 (2003); Li, Y., et al., J Neurol Sci 193, 137-146 (2002); Dugas, J. C., et al., J Neurosci 26, 10967-10983 (2006); Fox, M. A., et al., Molecular and Cellular Neuroscience 27, 140-150 (2004); Hoelzinger, D. B., et al., Neoplasia 7, 7-16 (2005); and Sato, K., et al., J Neurochem 92, 904-914 (2005); each of which is incorporated by reference in its entirety.

Although neurons and astrocytes do not seem to express ATX under physiological conditions, ATX is highly upregulated in astrocytes following brain lesion. Two hallmarks of reactive astrogliosis can be induced by LPA itself: hypertrophy of astrocytes and stress fiber formation. This may indicate an autoregulation loop of astrocytic activation, in which astrocytes upregulate the LPA-generating enzyme ATX and become activated by its metabolite LPA, while increased amounts of the metabolite inhibit the catalytic activity of ATX. See, e.g., Savaskan, N. E., et al., Cell Mol Life Sci 64, 230-243 (2007); Ramakers, G. J, & Moolenaar, W. H., Exp Cell Res 245, 252-262 (1998); and van Meeteren, L. A., et al., J Biol Chem 280, 21155-21161 (2005); each of which is incorporated by reference in its entirety.

ATX expression levels were shown to be elevated in glioblastoma multiform samples, and ATX was shown to augment invasiveness of cells transformed with ras, a key signaling molecule that promotes gliomagenesis. ATX expression was also detected in primary tumor tissues from neuroblastoma patients and retinoic acid induced expression of ATX in N-myc-amplified neuroblastoma cells.

There is significant evidence for ATX signaling in demyelination processes and in other neurodegenerative conditions. As noted above, it has been reported that addition of LPA to dorsal root fibers in ex vivo culture causes demyelination, whereas LPC fails to cause significant demyelination of nerve fibers in ex vivo cultures without further addition of recombinant ATX to the culture. Addition of recombinant ATX caused significant demyelination at equivalent levels to LPA presumable due to conversion of LPC to LPA through the enzymatic activity of ATX. In addition, injury induced demyelination was attenuated by about 50% in atx$^{+/-}$ mice over their wild type counterparts (Nagai, et al., *Molecular Pain* (2010), 6:78).

ATX protein levels were found deregulated in an animal model of MS (experimental autoimmune encephalitis; EAE) at the onset of clinical symptoms. See, e.g., Hoelzinger, D. B., et al. Neoplasia 7, 7-16 (2005); Nam, S. W., et al., Oncogene 19, 241-247 (2000); Kawagoe, H., et al., Cancer Res 57, 2516-2521 (1997); Dufner-Beattie, J., et al., Mol Carcinog 30, 181-189 (2001); Umemura, K., et al., Neuroscience Letters 400, 97-100 (2006); and Fuss, B., et al., J Neurosci 17, 9095-9103 (1997); each of which is incorporated by reference in its entirety. Moreover, significant ATX expression was been detected in the cerebrospinal fluid of patients suffering with multiple sclerosis (MS), while completely lacking from the control samples, suggesting a role for ATX in maintenance of cerebrospinal fluid homeostasis during pathological/demyelinating conditions. Hammack, B. N., et al. Proteomic analysis of multiple sclerosis cerebrospinal fluid. Mult Scler 10, 245-260 (2004); and Dennis, J., et al., J Neurosci Res 82, 737-742 (2005); each of which is incorporated by reference in its entirety.

Interestingly, ATX mRNA expression was found to be elevated in the frontal cortex of Alzheimer-type dementia patients indicating a potential involvement for ATX signaling in neurodegenerative diseases. LPA receptors are enriched in the CNS and their expression patterns suggest their potential involvement in developmental process including neurogenesis, neuronal migration, axon extension and myelination. Noteworthy, only two receptors have the same spatiotemporal expression as ATX in the CNS (Contos, J. J., et al., Mol Cell Biol 22, 6921-6929 (2002); Jaillard, C, ei al, Edg8/S1 P5: an oligodendroglial receptor with dual function on process retraction and cell survival. J Neurosci 25, 1459-1469 (2005); and Saba, J. D. Journal of cellular biochemistry 92, 967-992 (2004); each of which is incorporated by reference in its entirety). LPAi and S1P5 are specific for ODCs, and their expression highly correlates with the process of myelination. LPA1 is expressed in restricted fashion within the neuroblasts of the neuroproliferatve Ventricular Zone (VZ) of the developing cortex, in the dorsal olfactory bulb, along the pial cells of neural crest origin, and in developing facial bone tissue. Expression is observed during E11-E18, corresponding to a time period during which neurogenesis occurs. LPA1 expression is undetectable in the VZ after this point, to reappear during the first postnatal week within ODCs. Notably, Schwann cells (the myelinating cells of the Peripheral Nervous System; PNS) express high levels of LPA1 early in development and persistently throughout life, suggesting an influence of LPA on myelinating processes (Weiner. J. A. & Chun, J., Proc Natl Acad Sci USA 96, 5233-5238 (1999), which is incorporated by reference in its entirety).

The above data strongly support a critical role for ATX and LPA signaling in neuronal development, oligodendrocyte differentiation and myelination, as well as possibly in the autoregulation of astrocyte activation. Moreover, the regulation of ATX and thus LPA production at local sites of CNS injury, inflammatory or autoimmune, could contribute to tissue homeostasis through the numerous effects of LPA. As demyelination and deregulated cerebrospinal fluid homeostasis are the hallmarks of multiple sclerosis, a role of ATX and LPA signaling in the pathophysiology of multiple sclerosis seems very likely.

The S1P modulating agents and/or ATX modulating agents of formula (I) can be used to various forms of MS including relapsing-remitting, secondary-progressive, primary-progressive, and progressive-relapsing forms. In addition, S1P modulating agents and/or ATX modulating agents of formula (I) can be used alone or in conjunction with other agents to treat or prevent MS. In some embodiments, the compounds and salts described herein can be used to treat or prevent MS in combination with an immunomodulating therapy such as corticosteroids, beta interferon-1a (such as Avonex® or Rebif®), beta interferon-1b (Betaseron®), natalizumab (Tysabri®), glatiramer, and mitoxantrone.

Pain Mediation

Pain experienced by mammals can be divided into two main categories: acute pain (or nociceptive) and chronic pain which can be subdivided into chronic inflammatory pain and chronic neuropathic pain. Acute pain is a response to stimulus that causes tissue injury and is a signal to move away from the stimulus to minimize tissue damage. Chronic pain, on the other hand, serves no biological function and develops as a result of inflammation caused by tissue damage (inflammatory pain) or by damage to the nervous system such as demyelination (neuropathic pain). Chronic pain is generally characterized by stimulus-independent, persistent pain or by abnormal pain perception triggered by innocuous stimuli.

LPA has been found to be a mediator of both inflammatory pain and neuropathic pain. The transient receptor potential channel TRPV1 is known to be the originator of inflammatory pain. LPA has been shown to directly activate TRPV1 thereby creating pain stimulus by binding to its intracellular C-terminus (Tigyi, *Nature Chemical Biology* (January 2012), 8:22-23). Thus, compounds and salts which inhibit the formation of LPA by inhibiting the action of ATX would be useful in treating inflammatory pain.

LPA has also been shown to play a role in neuropathic pain. For example, sciatic nerve injury has been shown to induce demyelination, down-regulation of myelin-associated glycoprotein (MAG) and damage to Schwann cell partitioning of C-fiber-containing Remak bundles in the sciatic nerve and dorsal root. However, demyelination, MAG down-regulation and Remak bundle damage in the dorsal root were abolished in $LPA_1$ receptor-deficient (Lpar1$^{-/-}$) mice (Nagai, et al., *Molecular Pain* (2010), 6:78). These results indicate that compounds and salts that inhibit the formation of LPA by inhibiting the action of ATX would decrease dorsal root demyelination following nerve injury and decrease or eliminate neuropathic pain.

Thus the compounds and salts described herein are useful in treating or preventing chronic pain such as inflammatory pain and neuropathic pain in mammals. Rheumatoid Arthritis (RA)

Studies in human and animal models of RA suggest that ATX plays a role in the development and progress of the disease. For example, increased ATX mRNA expression was detected in synovial fibroblasts (SFs) from animal models of RA during differential expression profiling, and human RA SFs were shown to express mRNA for both ATX and LPARs (Aidinis, V., et al., PLoS genetics 1, e48 (2005); Zhao, C, et al., Molecular pharmacology 73, 587-600 (2008); each of which is incorporated by reference in its entirety). ATX is overexpressed from activated SFs in arthritic joints, both in animal models and human patients (see WO 2011/151461). ATX expression was shown to be induced from TNF, the major pro-inflammatory factor driving RA.

Disease development was assessed in well-established animal models of RA. When ATX expression was conditionally ablated specifically in SFs, the lack of ATX expression in the joints resulted in marked decreased inflammation and synovial hyperplasia. This suggested an active involvement of the ATX-LPA axis in the pathogenesis of the disease. Similar results were also obtained with pharmacologic inhibition of ATX enzymatic activity and LPA signaling. A series of ex vivo experiments on primary SFs revealed that ATX, through LPA production, stimulates rearrangements of the actin cytoskeleton, proliferation and migration to the extracellular matrix (ECM), as well as the secretion of proinflammatory cytokines and matrix metalloproteinases (MMPs). Moreover, the LPA effect was shown to be synergistic with TNF and dependent on the activation of MAPK cellular signaling pathways. See, e.g., Armaka, M., et al., The Journal of experimental medicine 205, 331-337 (2008); which is incorporated by reference in its entirety.

In one embodiment a method for treating an individual with RA or the individual at risk of suffering thereof comprises administering to said individual an S1P modulating agent and/or ATX modulating agent of formula (I) in conjunction with an anti-TNF antibody for use in the treatment of RA. Examples of suitable anti-TNF antibodies are adalimumab, etanercept, golimumab, and infliximab (Taylor P C, Feldmann M. Anti-TNF biologic agents: still the therapy of choice for rheumatoid arthritis. Nat Rev Rheumatol. 2009 October; 5(10):578-82).

Pulmonary Fibrosis

Evidence also suggests a role for ATX in pulmonary fibrosis. Mice lacking lysophosphatidic acid (LPA) receptor 1 (LPAR1) were protected from Bleomycin (BLM)-induced pulmonary fibrosis and mortality, suggesting a major role for LPA in disease pathophysiology. The majority of circulating LPA is produced by the phospholipase D activity of Autotaxin (ATX) and the hydrolysis of lysophosphatidylcholine (LPC). Increased ATX expression has been previously reported in the hyperplastic epithelium of fibrotic lungs of human patients and animal models.

Therefore, we hypothesized that genetic or pharmacologic inhibition of ATX activity would reduce local or circulating LPA levels and hence attenuate disease pathogenesis.

Lung Cancer

Increased ATX expression has been detected in a large number of malignancies, including mammary, thyroid, hepatocellular and renal cell carcinomas, glioblastoma and neuroblastoma, as well as NSCLC. Strikingly, transgenic overexpression of ATX was shown to induce spontaneous mammary carcinogenesis. In accordance, in vitro ATX overexpression in various cell types promotes proliferation and metastasis while inhibiting apoptosis. LPA's actions are concordant with many of the "hallmarks of cancer", indicating a role for LPA in the initiation or progression of malignant disease. Indeed LPA levels are significantly increased in malignant effusions, and its receptors are aberrantly expressed in several human cancers.

See, for example: Euer, N., et al., Anticancer Res 22, 733-740 (2002); Liu, S., et al., Cancer Cell 15, 539-550 (2009); Zhang, G., et al., Chin Med J (Engl) 112, 330-332 (1999); Stassar, M. J., et al., Br J Cancer 85. 1372-1382 (2001); Kishi, Y., et al., J Biol Chem 281, 17492-17500 (2006); Kawagoe, H., et al., Cancer Res 57, 2516-2521 (1997); Yang, Y., et al., Am J Respir Cell Mol Biol 21, 216-222 (1999); and Toews, M. L., et al. Biochim Biophys Acta 1582, 240-250 (2002); each of which is incorporated by reference in its entirety.

Pharmaceutical compositions can include a compound of formula (I), or a pharmaceutically acceptable salt thereof. More particularly, such compounds and salts can be formulated as pharmaceutical compositions using standard pharmaceutically acceptable carriers, fillers, solubilizing agents and stabilizers known to those skilled in the art. For example, a pharmaceutical composition including a compound of formula (I), or a pharmaceutically acceptable salt thereof, as described herein, is used to administer the appropriate compound, or a pharmaceutically acceptable salt thereof, to a subject.

The compounds of formula (I), or a pharmaceutically acceptable salt thereof, are useful for treating a disease or disorder associated with S1P receptor activity, and/or ATX activity. In one embodiment, a therapeutically effective amount of a compound of formula (I), or a pharmaceutically acceptable salt thereof, is administered to a subject in need thereof. In another embodiment, a pharmaceutical composition comprising a therapeutically effective amount of a compound of formula (I), or a pharmaceutically acceptable salt thereof, and a pharmaceutically-acceptable carrier is administered to a subject in need thereof.

The compounds and salts described herein can be used in combination with at least one further active ingredient, such as a medicament used in the treatment of multiple sclerosis such as Tysabri®, dimethyl fumarate, an interferon (such as pegylated or non-pegylated interferons, such as interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxyl)ethyl-rapamycin etc.); corticosteroids; cyclophosphamide; azathioprine; mitoxanthrone, methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD20 (e.g., rituximab and ocrelizumab), CD25, CD28, B7, CD40, CD45, CD56 (e.g., daclizumab), or CD58 or their ligands; or other immunomodulating agenty compounds, e.g. CTLA4Ig, or other adhesion molecule inhibitors, e.g. mAbs or low molecular weight inhibitors including Selectin antagonists and VLA-4 antagonists (such as Tysabri®); remyelinating agents such as BIIB033. Compounds and salts described herein can also be used in combination with agents which treat the symptoms of multiple sclerosis such as fampridine.

The dose of a compound of formula (I), or a pharmaceutically acceptable salt thereof, administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the compound, or a pharmaceutically acceptable salt thereof, can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering the compound, or a pharmaceutically acceptable salt thereof, to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound of formula (I), or a pharmaceutically acceptable salt thereof. Monitoring a property can include monitoring the property after the sample or subject has been administered a compound, or a pharmaceutically acceptable salt thereof. Monitoring a property can include monitoring a property after the sample or subject has been administered a known concentration of a compound, or a pharmaceutically acceptable salt thereof.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

Promoting myelination, remyelination or oligodendrocyte progenitor cell differentiation can prevent or can treat a pathological condition or symptom in a mammal. A number of diseases or disorders involve demyelination of the central or peripheral nervous system which can occur for a number of reasons such as immune dysfunction as in multiple sclerosis, encephalomyelitis, Guillain-Barre Syndrome, chronic inflammatory demyelinating polyneuropathy (CIDP), transverse myelitis, and optic neuritis; demyelination due to injury such as spinal cord injury, traumatic brain injury, stroke, acute ischemic optic neuropathy, or other ischemia, cerebral palsy, neuropathy (e.g. neuropathy due to diabetes, chronic renal failure, hypothyroidism, liver failure, or compression of the nerve), post radiation injury, and central pontine myelolysis (CPM); inherited conditions such as Charcot-Marie-Tooth disease (CMT), Sjogren-Larsson syndrome, Refsum disease, Krabbe disease, Canavan disease, Alexander disease, Friedreich's ataxia, Pelizaeus-Merzbacher disease, Bassen-Kornzweig syndrome, metachromatic leukodystrophy (MLD), adrenoleukodystrophy, and nerve damage due to pernicious anemia; viral infection such as progressive multifocal leukoencephalopathy (PML), Lyme disease, or tabes dorsalis due to untreated syphilis; toxic exposure due to chronic alcoholism (which is a possible cause of Marchiafava-Bignami disease), chemotherapy, or exposure to chemicals such as organophosphates; or dietary deficiencies such as vitamin B12 deficiency, vitamin E deficiency, and copper deficiency. Some demyelination disorders can have unknown or multiple causes such as trigeminal neuralgia, Marchiafava-Bignami disease and Bell's palsy. In addition, demyelination can contribute to neuropathic pain. Compounds and salts described herein are expected to be useful in treating demyelination disorders.

Since LPA is a proinflammatory factor reducing the amount of LPA producted by inhibiting ATX is useful for treating inflammatory disorders such as asthma, allergies, arthritis, inflammatory neuropathies, transplantation rejection, Crohn's disease, ulcerative colitis, lupus erythematosis, psoriasis, an inflammatory bowel condition, and diabetes.

LPA has been shown to be involved in wound healing and stimulates the proliferation and migration of endothelial cells promoting processes such as angiogenesis. However, these same processes when deregulated can promote tumor growth and metastasis, and LPA is thought to contribute to the development, progression, and metastasis of several types of cancer including ovarian, prostate, melanoma, breast, head and neck cancers (see Gendaszewska-Darmach, Acta Biochimica Polonica (2008), 55(2):227-240). In addition, since ATX is located outside the cell in circulation, ATX inhibitors are expected to be of most benefit outside the cell. Therefore, ATX inhibitors are expected to be useful in treating cancer, particularly multidrug resistant (MDR) cancers where drug efflux mechanisms are the largest contributor to the drug resistance.

A compound of formula (I), or a pharmaceutically acceptable salt thereof, formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes.

Thus, compound of formula (I), or a pharmaceutically acceptable salt thereof, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound, or a pharmaceutically acceptable salt thereof, may be combined with one or more excipients and used in the form of ingestible tablets, buccal tablets, troches, capsules, elixirs, suspensions, syrups, or wafers, and the like. Such compositions and preparations should contain at least about 0.1% of active compound, or a pharmaceutically acceptable salt thereof. The percentage of the compositions and preparations may, of course, be varied and may conveniently be between about 2 to about 60% of the weight of a given unit dosage form. The amount of active compound, or a pharmaceutically acceptable salt thereof, in such therapeutically useful compositions can be such that an effective dosage level will be obtained.

The tablets, troches, pills, capsules, and the like can include the following: binders such as gum tragacanth, *acacia*, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, or a pharmaceutically acceptable salt thereof, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound, or a pharmaceutically acceptable salt thereof, may be incorporated into sustained-release preparations and devices.

The active compound, or a pharmaceutically acceptable salt thereof, may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, isotonic agents, for example, sugars, buffers or sodium chloride, will be included. Prolonged absorption of the injectable compositions can be brought about by the use in the compositions of agents delaying absorption, for example, aluminum monostearate or gelatin.

Sterile injectable solutions can be prepared by incorporating the active compound, or a pharmaceutically acceptable salt thereof, in the required amount in the appropriate solvent with various of the other ingredients enumerated above, as required, followed by filter sterilization. In the case of sterile powders for the preparation of sterile injectable solutions, the methods of preparation can be vacuum drying and the freeze drying techniques, which can yield a powder of the active ingredient plus any additional desired ingredient present in the previously sterile-filtered solutions.

For topical administration, a compound of formula (I), or a pharmaceutically acceptable salt thereof, may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds and salts can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I), or a pharmaceutically acceptable salt thereof, to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of formula (I), or a pharmaceutically acceptable salt thereof, can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of formula (I), or a pharmaceutically acceptable salt thereof, in a liquid composition, such as a lotion, can be from about 0.1 to about 25 weight percent, such as from about 0.5-10 weight percent. The concentration in a semi-solid or solid composition such as a gel or a powder can be about 0.1-5 wt-%, such as about 0.5-2.5 weight percent based on the total weight of the composition.

The amount of the compound, or a pharmaceutically acceptable salt thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound, or a pharmaceutically acceptable salt thereof, can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound, or a pharmaceutically acceptable salt thereof. The desired peak plasma concentration can be from about 0.5 µM to about 75 µM, such as, about 1 µM to 50 µM, or about 2 µM to about 30 µM. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound of formula (I), or a pharmaceutically acceptable salt thereof, and instructional material which can describe administering the compound, or a pharmaceutically acceptable salt thereof, or a composition comprising the compound, or a pharmaceutically acceptable salt thereof, to a cell or a subject. This should be construed to include other embodiments of kits that are known to those skilled in the art, such as a kit comprising a (such as sterile) solvent for dissolving or suspending the compound, or a pharmaceutically acceptable salt thereof, or composition prior to administering the compound or composition to a cell or a subject. In some embodiments, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

The compounds of formula (I), or a pharmaceutically acceptable salt thereof, can be prepared from readily available starting materials using the following general methods and procedures. It will be appreciated that where typical or preferred process conditions (i.e., reaction temperatures, times, mol ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the compounds of formula (I) may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The compounds of formula (I) can be prepared by the synthetic protocols illustrated in Scheme 1, where X, $X^1$, $X^2$, $X^3$, $X^4$, $X^5$, $R^1$, $R^2$, L, $L^1$ and A are as defined herein, Hal is a halogen, and LG is a leaving group, such as a halogen, or a functional group suitable for a coupling reaction, such as a double or triple bond.

Scheme 1

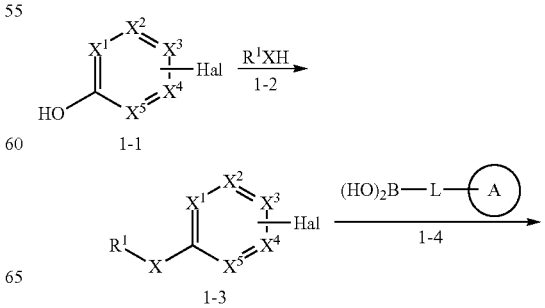

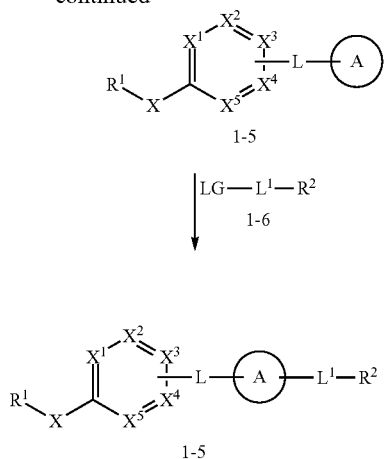

Compound 1-1 is reacted with at least a stoichiometric amount and in some embodiments an excess of compound 1-2. The reaction is typically conducted under conventional coupling conditions well known in the art. In one embodiment, the reaction is conducted with the use of a coupling agent such as DIAD in the presence of $PPh_3$ in a suitable solvent, such as toluene. The reaction is continued until substantially complete which typically occurs within about 1 to 12 hours. Upon reaction completion, compound 1-3 can be recovered by conventional techniques such as neutralization, extraction, precipitation, chromatography, filtration and the like.

A halogenated compound 1-3, in some embodiments a brominated compound, is then reacted with an appropriately substituted boronic acid derivative of formula $B(OH)_2$-L-A (compound 1-4), or a boronic ester thereof, in an inert solvent, for example aqueous 1,4-dioxane, in the presence of a mild base, for example potassium carbonate or sodium bicarbonate. In some embodiments the reaction is conducted in the presence of a metal catalyst with an appropriate ligand, for example dichlorobis(triphenylphosphine) palladium(II) or [1,1'-bis(diphenylphosphino)ferrocene]dichloropalladium(II), at an elevated temperature (e.g., 90-170° C.), for about 10 minutes to about 5 hours. Upon reaction completion, compound 1-5 can be recovered by conventional techniques such as neutralization, extraction, precipitation, chromatography, filtration and the like.

It will be appreciated that the -L-$R^2$ substituent can be modified or added to ring A either after (as shown in Scheme 1) or before the addition of the -L-A moiety. The -L-$R^2$ moiety may be coupled to compound 1-5 under substitution reaction conditions with an appropriate reagent of formula LG-$L^1$-$R^2$ (where LG is a leaving group such as a halo, hydroxyl, alkoxy, and the like, or a functional group suitable for a coupling reaction, such as a double or triple bond) as shown in Scheme 1. Typical substitution reaction conditions include the presence of a base, such as cesium carbonate, potassium carbonate, sodium bicarbonate, triethylamine, and the like, in a polar aprotic solvent, such as N,N-dimethylformamide, and optionally an elevated temperature of about 100-150° C., or in a microwave. Upon reaction completion, compounds of formula (I) can be recovered by conventional techniques such as neutralization, extraction, precipitation, chromatography, filtration and the like.

| \multicolumn{2}{l}{List of Abbreviations and Acronyms} |  |
|---|---|
| Abbreviation | Meaning |
| ° C. | Degree Celsius |
| Ac | Acetate |
| atm | Atmosphere |
| ATX | Autotaxin |
| BINAP | 2,2'-Bis(diphenylphosphino)-1,1'-binaphthyl |
| BOC | tert-Butoxycarbonyl |
| bs | Broad singlet |
| BSA | Bovine serum albumin |
| Bu | Butyl |
| cat | Catalytic amount |
| CNTF | Ciliary neurotrophic factor |
| conc | Concentrated |
| Cy | Cyclohexyl |
| d | Doublet |
| d | day |
| dba | dibenzylideneacetone |
| DCE | Dichloroethane |
| DCM | Dichloromethane |
| dd | Doublet of doublets |
| $ddH_2O$ | Double-distilled water |
| DIAD | Diisopropyl azodicarboxylate |
| DMEM | Dulbecco's modified Eagle's medium |
| DMF | Dimethylformamide |
| DMSO | Dimethylsulfoxide |
| DNase | Deoxyribonuclease |
| dppf | 1,1'-Bis(diphenylphosphino)ferrocene |
| EA | Ethylacetate |
| $EC_{50}$ | Half maximal effective concentration |
| $EC_{80}$ | Eighty percent maximal effective concentration |
| EGTA | Ethylene glycol tetraacetic acid |
| Emax | Mmaximum possible effect |
| eq | Equivalents |
| ESI-MS | Electrospray ionization |
| Et | Ethyl |
| g | Grams |
| h/H | Hours |
| HBSS | Hank's buffered saline solution |
| HEPES | 4-(2-hydroxyethyl)-1-piperazineethanesulfonic acid |
| HPCD | Hydroxypropyl-β-cyclodextrin |
| HPLC | High-performance liquid chromatography |
| Hz | Hertz |
| $IC_{50}$ | The half maximal inhibitory concentration |
| Iu/iu | International unit |
| J | Coupling constant |
| KDa | KiloDalton |
| Kg | Kilogram |
| L | Liter |
| LCMS | Liquid chromatography-mass spectrometry |
| LPA | Lysophosphatidic acid |
| LPC | Lysolecithin |
| LPLD | Lysophospholipase D |
| m | multiplet |
| M | Molar |
| m | multiplet |
| m/z | mass-to-charge ratio |
| M + H | Mass peak plus hydrogen |
| MAG | Myelin associated glycoprotein |
| MBP | Myelin basic protein |
| Me | Methyl |
| mg | Milligram |
| MHz | Megahertz |
| min | Minute |
| mL | Milliliter |
| mM | Millimolar |
| mm | Millimeter |
| mmol | Millimole |
| MOG | Myelin oligodendrocyte glycoprotein |
| mol | Mole |
| MS | Mass spectrometry |
| Ms | Methanesulfonyl |
| MSD | Meso Scale Discovery-R |
| MW | Microwave |
| N | Normal |
| nL | Nanoliter |
| nM | Nanometer |
| NMR | Nuclear magnetic resonance |
| OPC | Oligodendrocyte precursor cells |

-continued

List of Abbreviations and Acronyms

| Abbreviation | Meaning |
| --- | --- |
| PAGE | Polyacrylamide gel electrophoresis |
| PBS | Phosphate buffered saline |
| PE | Petroleum ether |
| PEA | Paraformaldehyde |
| Ph | Phenyl |
| pmol | Picomole |
| prep | Preparative |
| q | Quartet |
| rpm | Revolutions per minute |
| rpm | Revolutions per minute |
| rt | Room temperature |
| s | Singlet |
| s.c. | Subcutaneously |
| SDS | Sodium dodecyl sulfate |
| sec | Second |
| t | Triplet |
| t-Bu | tert-Butyl |
| TFA | Trifluoroacetic acid |
| THF | Tetrahydrofuran |
| Y | Yield |
| δ | Chemical shift |
| μg | Microgram |
| μL | Microliter |
| μM | Micromolar |
| μm | Micrometer |

Intermediate 1: 1-Bromo-4-(octyloxy)benzene

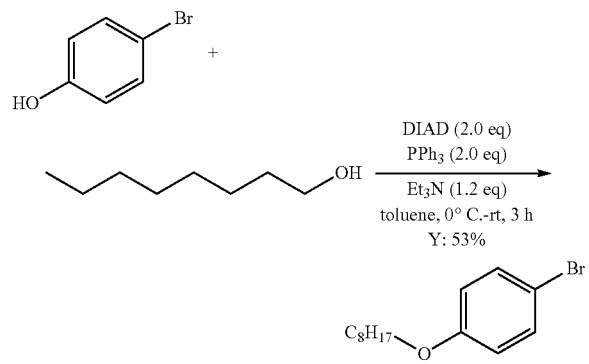

To a mixture of 4-bromophenol (8.0 g, 46.5 mmol, 1.0 eq), octan-1-ol (7.25 g, 55.8 mmol, 1.2 eq) and PPh$_3$ (24.4 g, 93.0 mmol, 2.0 eq) in toluene (50 mL) was added dropwise DIAD (18.8 g, 93.0 mmol, 2.0 eq) at 0° C. The reaction mixture was stirred at rt for 3 hours. And then, the solvent was removed under reduced pressure to give the crude title product, which was purified by column chromatography on silica gel, eluting with petroleum ether to furnish the target compound 1-bromo-4-(octyloxy)benzene as a colorless oil (7.0 g, 53% yield). LCMS: m/z 285.1 [M+H]$^+$; $^1$H NMR (CDCl$_3$, 400 MHz) δ: 7.38-7.34 (m, 2H), 6.79-6.75 (m, 2H), 3.91 (t, J=6.8 Hz, 2H), 1.80-1.73 (m, 2H), 1.46-1.28 (m, 10H), 0.89 (t, J=6.8 Hz, 3H).

Intermediate 2: 1-Bromo-4-(trans-4-tert-butylcyclohexyloxy)benzene

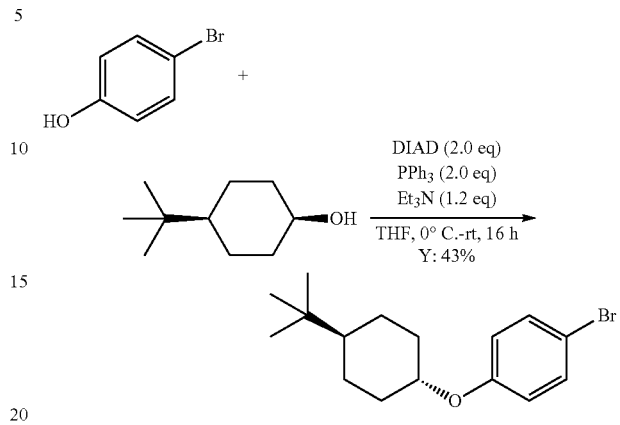

To a mixture of 4-bromophenol (11.5 g, 66.9 mmol, 1.0 eq), cis-4-tert-butylcyclohexanol (12.5 g, 80.2 mmol, 1.2 eq), PPh$_3$ (35 g, 133.8 mmol, 2.0 eq) and triethylamine (8.1 g, 80.3 mol, 1.2 eq) in THF (100 mL) was added dropwise DIAD (27.1 g, 133.8 mmol, 2.0 eq) at 0° C. The mixture was allowed to warm up to rt and stirred for 16 hours. The solvent was then removed under reduced pressure and the residue was purified by column chromatography on silica gel, eluting with petroleum ether to afford the target compound 1-bromo-4-(trans-4-tert-butylcyclohexyloxy)benzene as a white solid (9.0 g, 43% yield). $^1$H NMR (CDCl$_3$, 400 MHz) δ: 7.35-7.33 (m, 2H), 6.78-6.76 (m, 2H), 4.06-4.04 (m, 1H), 2.18-2.14 (m, 2H), 1.87-1.84 (m, 2H), 1.38-1.35 (m, 2H), 1.13-1.07 (m, 3H), 0.87 (s, 9H).

Intermediate 3: 3-(4-(Octyloxy)phenyl)pyridine

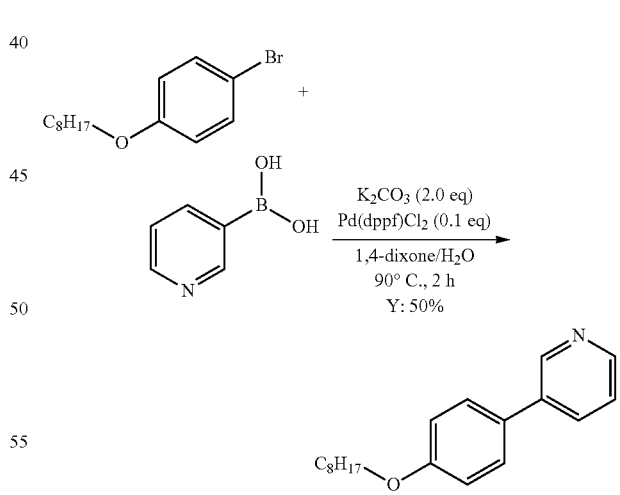

A mixture of 1-bromo-4-(octyloxy)benzene (1.1 g, 3.87 mmol, 1.0 eq), pyridin-3-ylboronic acid (476 mg, 3.87 mmol, 1.0 eq), Pd(dppf)Cl$_2$.DCM (310 mg, 0.38 mmol, 0.1 eq) and K$_2$CO$_3$ (1.07 g, 7.74 mmol, 2.0 eq) in mixed solvents (1,4-dioxane/H$_2$O, 4/1, 9 mL) was heated to 90° C. and stirred for 2 h under N$_2$. After cooling down to rt, the solvents were removed in vacuo, and the residue was suspended with EtOAc (10 mL), followed by filtration. The filtrate was concentrated under reduced pressure, and the residue was purified by column chromatography on silica gel (petroleum ether/EtOAc=10/1) to give the title compound as a white solid (498 mg, 50% yield). LCMS: m/z 284.1 [M+H]⁺; ¹HNMR (400 MHz, CDCl₃) δ: 8.84 (s, 1H), 8.56 (d, J=4.0 Hz, 1H), 7.85 (d, J=7.6 Hz, 1H), 7.53-7.50 (m, 2H), 7.37-7.33 (m, 1H), 7.01 (d, J=8.4 Hz, 2H), 4.02 (t, J=6.8 Hz, 2H), 1.86-1.79 (m, 2H), 1.51-1.27 (m, 10H), 0.92-0.89 (t, J=6.8 Hz, 3H).

Intermediate 4: 3-(4-(Octyloxy)phenyl)piperidine

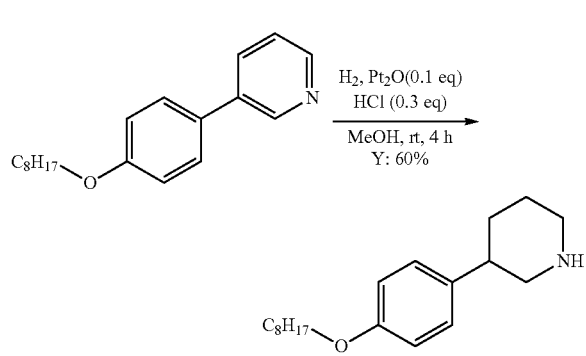

To a mixture of 3-(4-(octyloxy)phenyl)pyridine (600 mg, 2.12 mmol, 1.0 eq) and conc. HCl (60 mg, 0.6 mmol, 0.3 eq) in MeOH (3 mL) was added PtO₂ (48 mg, 0.2 mmol, 0.1 eq). The mixture was purged with H₂ for three times and then stirred at rt for 4 hours. The mixture was then filtered, and the filtrate was concentrated in vacuo. The residue was purified by prep-HPLC (MeOH/H₂O from 30% to 95%, containing 0.05% TFA) to give the title compound as a white solid (364 mg, 60% yield). ¹HNMR (400 MHz, CDCl₃) δ: 7.08 (d, J=8.0 Hz, 2H), 6.84 (d, J=8.0 Hz, 2H), 3.92 (t, J=6.8 Hz, 2H), 3.44 (bs, 2H), 3.08-3.02 (m, 1H), 2.86 (bs, 2H), 2.08-2.00 (m, 4H), 1.80-1.73 (m, 2H), 1.46-1.28 (m, 10H), 0.90-0.87 (m, 3H).

Intermediate 5: Ethyl 3-(3-(4-(octyloxy)phenyl)piperidin-1-yl)propanoate

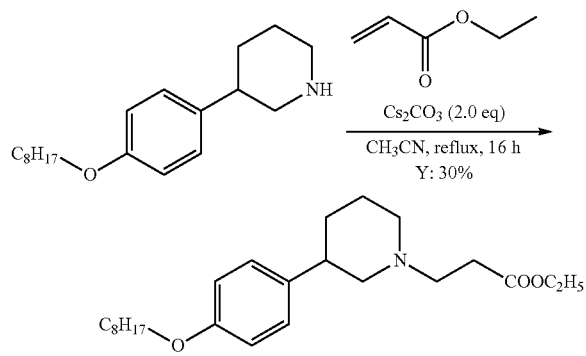

A stirred mixture of 3-(4-(octyloxy)phenyl)piperidine (140 mg, 0.48 mmol, 1.0 eq), ethyl acrylate (71.5 mg, 0.55 mmol, 1.1 eq) and Cs₂CO₃ (312 mg, 0.96 mol, 2.0 eq) in CH₃CN (3 mL) was heated to reflux for 16 hours. After cooling down to rt, the mixture was filtrated, and the filtrate was concentrated in vacuo, and the residue was purified by prep-HPLC (MeOH/H₂O from 30% to 95%, containing 0.05% TFA) to give the title compound as a colorless oil (56 mg, 30% yield). LCMS: m/z 390.2 [M+H]⁺.

Example 1

3-(3-(4-(Octyloxy)phenyl)piperidin-1-yl)propanoic acid (Compound 5)

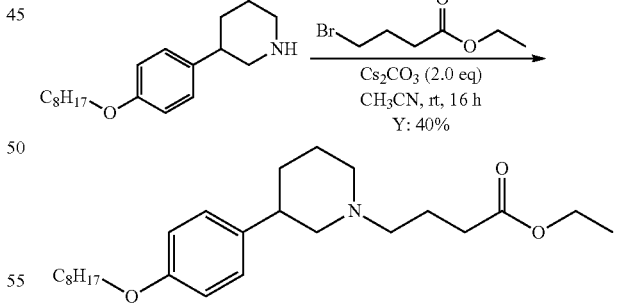

To a mixture of ethyl 3-(3-(4-(octyloxy)phenyl)piperidin-1-yl)propanoate (50 mg, 0.13 mmol, 1.0 eq) in mixed solvents (THF/H₂O, 8/1, 2 mL) was added LiOH.H₂O (10 mg, 0.26 mmol, 2.0 eq). The mixture was stirred at rt for 16 h. The reaction mixture was then adjusted to pH=6 with dilute aq. HCl. The solvent was removed in vacuo and the residue was purified by pre-HPLC (MeOH/H₂O from 30% to 95%, containing 0.05% TFA) to give 3-(3-(4-(octyloxy)phenyl)piperidin-1-yl)propanoic acid as a colorless oil (14 mg, 30% yield). LCMS: m/z 362.3 [M+H]⁺; ¹H NMR (400 MHz, CD₃OD) δ: 7.20 (d, J=8.4 Hz, 2H), 6.89 (d, J=8.4 Hz, 2H), 3.95 (t, J=6.8 Hz, 2H), 3.64-3.53 (m, 2H), 3.40 (t, J=6.8 Hz, 2H), 3.06-2.74 (m, 5H), 2.11-1.72 (m, 6H), 1.49-1.32 (m, 10H), 0.93-0.89 (m, 3H).

Intermediate 6: Ethyl 4-(3-(4-(octyloxy)phenyl)piperidin-1-yl)butanoate

To a stirred mixture of 3-(4-(octyloxy)phenyl)piperidine (100 mg, 0.35 mmol, 1.0 eq) and Cs₂CO₃ (228 mg, 0.7 mol, 2.0 eq) in CH₃CN (3 mL) was added ethyl 4-bromobutanoate (74 g, 0.38 mol, 1.1 eq). The mixture was heated to reflux for 16 hours. After cooling down rt, the mixture was filtrated, and the filtrate was concentrated in vacuo, and the residue was purified by prep-HPLC (MeOH/H₂O from 30% to 95%, containing 0.05% TFA) to give the title compound as a yellow oil (56 mg, 40% yield). LCMS: m/z 404.1 [M+H]⁺.

Example 2

4-(3-(4-(Octyloxy)phenyl)piperidin-1-yl)butanoic acid (Compound 6)

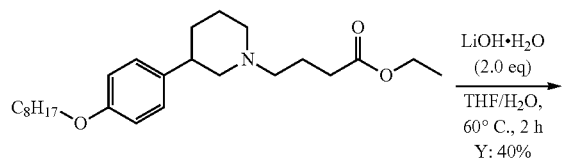

Using standard hydrolysis condition as described in example 1, 4-(3-(4-(octyloxy)phenyl)piperidin-1-yl)butanoic acid was obtained as a yellow oil (30 mg, 40% yield). LCMS: m/z 376.3 [M+H]$^+$; $^1$H NMR (400 MHz, CD$_3$OD) δ: 7.20 (d, J=8.4 Hz, 2H), 6.89 (d, J=8.4 Hz, 2H), 3.95 (t, J=6.4 Hz, 2H), 3.65-3.51 (m, 2H), 3.21-3.17 (m, 2H), 3.06-3.00 (m, 3H), 2.46 (t, J=6.8 Hz, 2H), 2.10-1.71 (m, 8H), 1.50-1.31 (m, 10H), 0.92-0.89 (m, 3H).

Intermediate 7: 3-(4-(trans-4-tert-Butylcyclohexyloxy)phenyl)pyridine

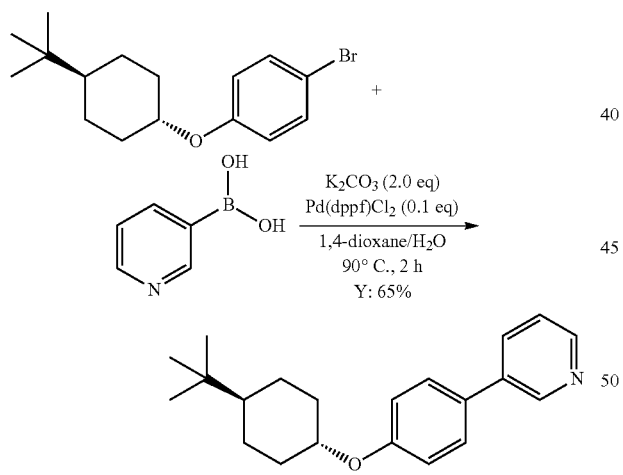

3-(4-(trans-4-tert-butylcyclohexyloxy)phenyl)pyridine was prepared using the same condition as that of 3-(4-(octyloxy)phenyl)pyridine as in intermediate 3. The title compound was obtained as a white solid (130 mg, 65% yield). LCMS m/z 310.2 [M+H]$^+$; $^1$HNMR (400 MHz, CDCl$_3$) δ: 8.81 (d, J=2.0 Hz, 1H), 8.54 (dd, J=3.6, 1.2 Hz, 1H), 7.84-7.81 (m, 1H), 7.50-7.48 (dd, J=6.4, 1.6 Hz, 2H), 7.34-7.26 (m, 1H), 6.99 (d, J=2.0 Hz, 2H), 4.18-4.16 (m, 1H), 2.25-2.21 (m, 2H), 1.89-1.87 (m, 2H), 1.44-1.40 (m, 2H), 1.16-1.08 (m, 3H), 0.89 (s, 9H).

Intermediate 8: 3-(4-(trans-4-tert-Butylcyclohexyloxy)phenyl)piperidine

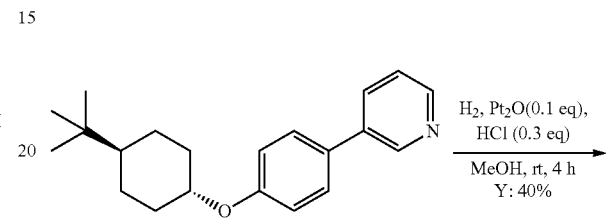

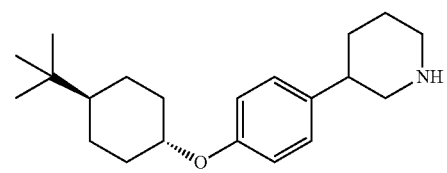

3-(4-(trans-4-tert-Butylcyclohexyloxy)phenyl)piperidine was prepared using the same condition as that of 3-(4-(octyloxy)phenyl)piperidine in intermediate 4. The title compound was obtained as a white solid (80 mg, 40% yield). LCMS m/z 316.2 [M+H]$^+$; $^1$HNMR (400 MHz, CDCl$_3$) δ: 8.91 (bs, 1H), 7.06 (d, J=8.4 Hz, 2H), 6.84 (d, J=8.8 Hz, 2H), 4.11-4.04 (m, 1H), 3.47-3.42 (m, 2H), 3.40-2.84 (m, 3H), 2.18-1.84 (m, 7H), 1.67-1.63 (m, 1H), 1.41-1.32 (m, 2H), 1.17-1.05 (m, 3H), 0.87 (s, 9H).

Example 3

3-(3-(4-(trans-4-tert-Butylcyclohexyloxy)phenyl)piperidin-1-yl)propanoic acid (Compound 3)

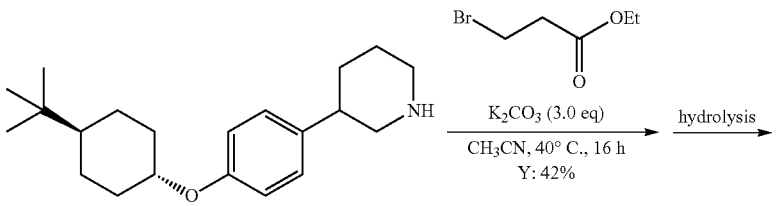

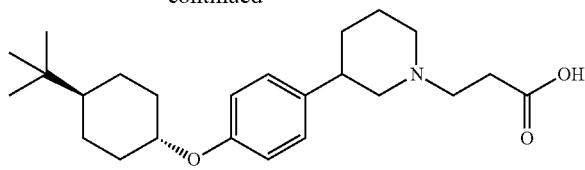

Using the same condition as that of ethyl 4-(3-(4-(octyloxy)phenyl)piperidin-1-yl)butanoate in intermediate 6, ethyl 3-(3-(4-(trans-4-tert-butylcyclohexyloxy)phenyl)piperidin-1-yl)propanoate was obtained as a yellow oil (42 mg, 42% yield). LCMS m/z 416.2 [M+H]$^+$.

Using standard hydrolysis condition, the title compound was obtained as a colorless oil (13 mg, 40% yield). LCMS m/z 388.3 [M+H]$^+$; $^1$HNMR (400 MHz, CD$_3$OD) δ: 7.19 (d, J=8.4 Hz, 2H), 6.88 (d, J=8.4 Hz, 2H), 4.16-4.15 (m, 1H), 3.60-3.37 (m, 2H), 3.36-3.33 (m, 2H), 3.03-2.99 (m, 3H), 2.69-2.65 (m, 2H), 2.18-1.86 (m, 8H), 1.35-1.11 (m, 5H), 0.90 (s, 9H).

Example 4

4-(3-(4-(cis-4-tert-Butylcyclohexyloxy)phenyl)piperidin-1-yl)butanoic acid (Compound 4)

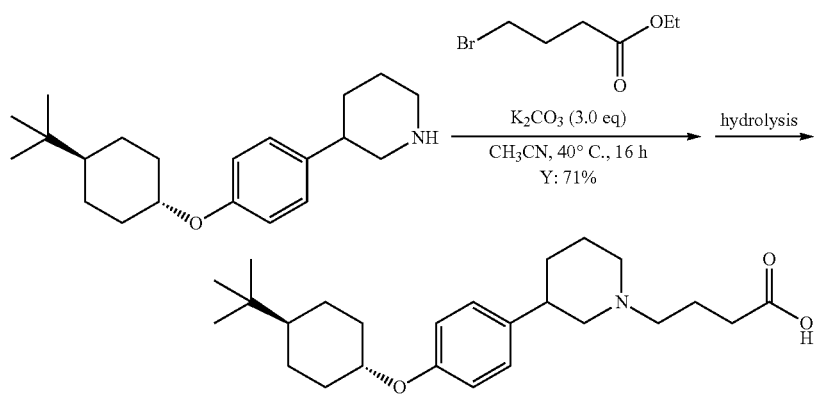

Using the same condition as that of ethyl 4-(3-(4-(octyloxy)phenyl)piperidin-1-yl)butanoate in intermediate 6, ethyl 4-(3-(4-(trans-4-tert-butylcyclohexyloxy)phenyl)piperidin-1-yl)butanoate was obtained as a yellow oil (67 mg, 71% yield). LCMS m/z 430.2 [M+H]$^+$.

Using standard hydrolysis condition, the title compound was obtained as a colorless oil (22 mg, 37% yield). LCMS m/z 402.3 [M+H]$^+$; $^1$HNMR (400 MHz, CD$_3$OD) δ: 7.19 (d, J=8.4 Hz, 2H), 6.88 (d, J=8.8 Hz, 2H), 4.16-4.14 (m, 1H), 3.64-3.53 (m, 2H), 3.19-3.16 (m, 2H), 3.01-2.96 (m, 3H), 2.48-2.45 (m, 2H), 2.18-1.86 (m, 10H), 1.36-1.08 (m, 5H), 0.90 (s, 9H).

Intermediate 9: 1-Bromo-3-(octyloxy)benzene

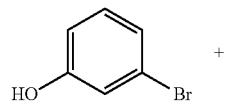

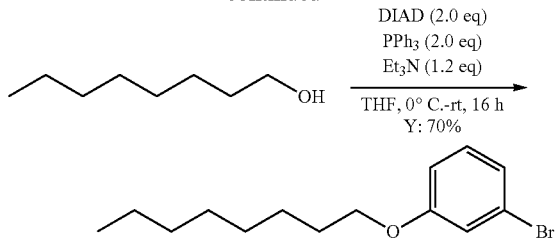

A mixture of 3-bromophenol (1.9 g, 10.9 mmol, 1.0 eq), octan-1-ol (1.4 g, 10.9 mmol, 1.0 eq), Et$_3$N (1.3 g, 13.1 mmol, 1.2 eq) and PPh$_3$ (5.7 g, 21.8 mmol, 2.0 eq) in THF (10 mL) was stirred at rt for 1 h. Then DIAD (4.4 g, 21.8 mmol, 2.0 eq) was added dropwise at 0° C. The mixture was stirred at rt for another 16 h. Then the solvent was removed and the residue was purified by column chromatography (PE/EA=8/1) to give the title compound as a yellow oil (2.2 g, 70% yield). LCMS m/z 285.1 [M+H]$^+$.

Intermediate 10: 3-(3-(Octyloxy)phenyl)pyridine

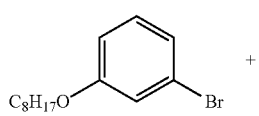

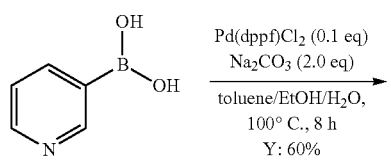

-continued

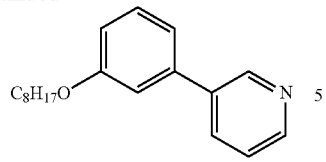

A mixture of 1-bromo-3-(octyloxy)benzene (1.4 g, 4.9 mmol, 1.0 eq), pyridin-3-ylboronic acid (723 mg, 5.9 mmol, 1.2 eq), Na₂CO₃ (1.0 g, 9.8 mmol, 2.0 eq) and Pd(dppf)Cl₂.DCM (400 mg, 0.5 mmol, 0.1 eq) in mixed solvents (toluene/EtOH/H₂O, 4/2/1, 10 mL) was heated to 100° C. and stirred for 8 h under N₂. After cooling down to rt, the resulting mixture was filtered and the filtrate was diluted with water (10 mL), extracted with ethyl acetate (30 mL×3). The combined organic layers were washed with brine (30 mL), dried over anhydrous Na₂SO₄ and filtered. The solvent was evaporated under reduced pressure to give the residue, which was purified by column chromatography on silica gel (PE/EA=10/1) to give the title compound as a yellow solid (837 mg, 60% yield). LCMS m/z 284.1 [M+H]⁺.

Intermediate 11: 3-(3-(Octyloxy)phenyl)piperidine

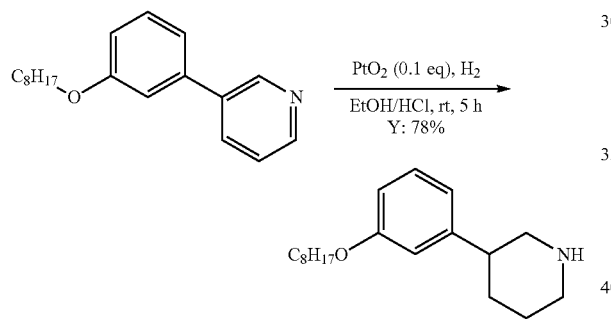

To a mixture of 3-(3-(octyloxy)phenyl)pyridine (500 mg, 1.8 mmol, 1.0 eq) and conc. HCl (cat) in MeOH (3 mL) was added PtO₂ (43 mg, 0.18 mmol, 0.1 eq). The mixture was purged with H₂ for three times and then stirred at rt for 5 h. The mixture was then filtered, and the filtrate was concentrated in vacuo to give the title compound as a colorless oil (400 mg, 78% yield). LCMS m/z 290.1 [M+H]⁺.

Example 5

3-(3-(3-(Octyloxy)phenyl)piperidin-1-yl)propanoic acid (Compound 49)

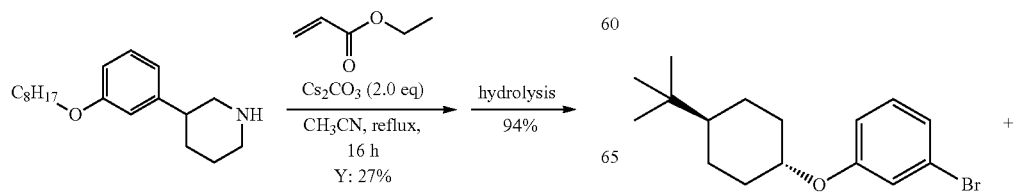

-continued

A stirred mixture of 3-(3-(octyloxy)phenyl)piperidine (100 mg, 0.35 mmol, 1.0 eq), ethyl acrylate (70 mg, 0.7 mmol, 2.0 eq) and Cs₂CO₃ (228 mg, 0.70 mmol, 2.0 eq) in CH₃CN (3 mL) was heated to reflux for 16 h. After cooling down to rt, the mixture was filtrated. The filtrate was concentrated in vacuo and the residue was purified by prep-HPLC (MeCN/H₂O from 30% to 95%, containing 0.05% TFA) to give ethyl 3-(3-(3-(octyloxy)phenyl)piperidin-1-yl)propanoate as a yellow oil (36 mg, 27% yield). LCMS m/z 390.3 [M+H]⁺.

Following standard hydrolysis condition, the title compound was obtained as a yellow solid (30 mg, 91% yield). LCMS m/z 362.3 [M+H]⁺; ¹H NMR (400 MHz, CD₃OD) δ: 7.16-7.12 (m, 1H), 6.74-6.70 (m, 3H), 3.85 (t, J=6.4 Hz, 2H), 3.52-3.44 (m, 2H), 3.26 (bs, 2H), 2.97-2.89 (m, 3H), 2.55 (bs, 2H), 1.96-1.89 (m, 3H), 1.69-1.62 (m, 3H), 1.38-1.33 (m, 2H), 1.25-1.21 (m, 8H), 0.80 (t, J=6.4 Hz, 3H).

Example 6

4-(3-(3-(Octyloxy)phenyl)piperidin-1-yl)butanoic acid (Compound 50)

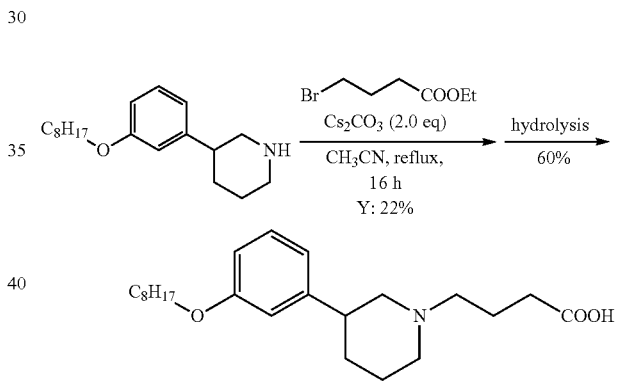

Using the same condition as that of ethyl 4-(3-(4-(octyloxy)phenyl)piperidin-1-yl)butanoate in intermediate 6, ethyl 4-(3-(3-(octyloxy)phenyl)piperidin-1-yl)butanoate as a yellow oil (46 mg, 22% yield). LCMS m/z 404.2 [M+H]⁺.

Following standard hydrolysis condition, the title compound was obtained as a yellow oil (25 mg, 60% yield). LCMS m/z 376.3 [M+H]⁺; ¹H NMR (400 MHz, CD₃OD) δ: 7.26-7.22 (m, 1H), 6.86-6.80 (m, 3H), 3.96 (t, J=6.4 Hz, 2H), 3.60-3.51 (m, 2H), 3.13-2.83 (m, 5H), 2.49-2.46 (m, 2H), 2.07-1.89 (m, 5H), 1.80-1.69 (m, 3H), 1.51-1.44 (m, 2H), 1.37-1.32 (m, 8H), 0.92-0.86 (m, 3H).

Intermediate 12: 3-(3-((trans-4-(tert-Butyl)cyclohexyl)oxy)phenyl)pyridine

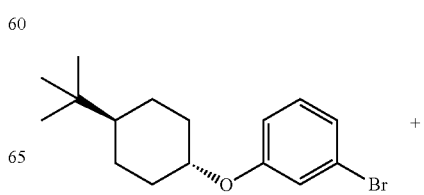

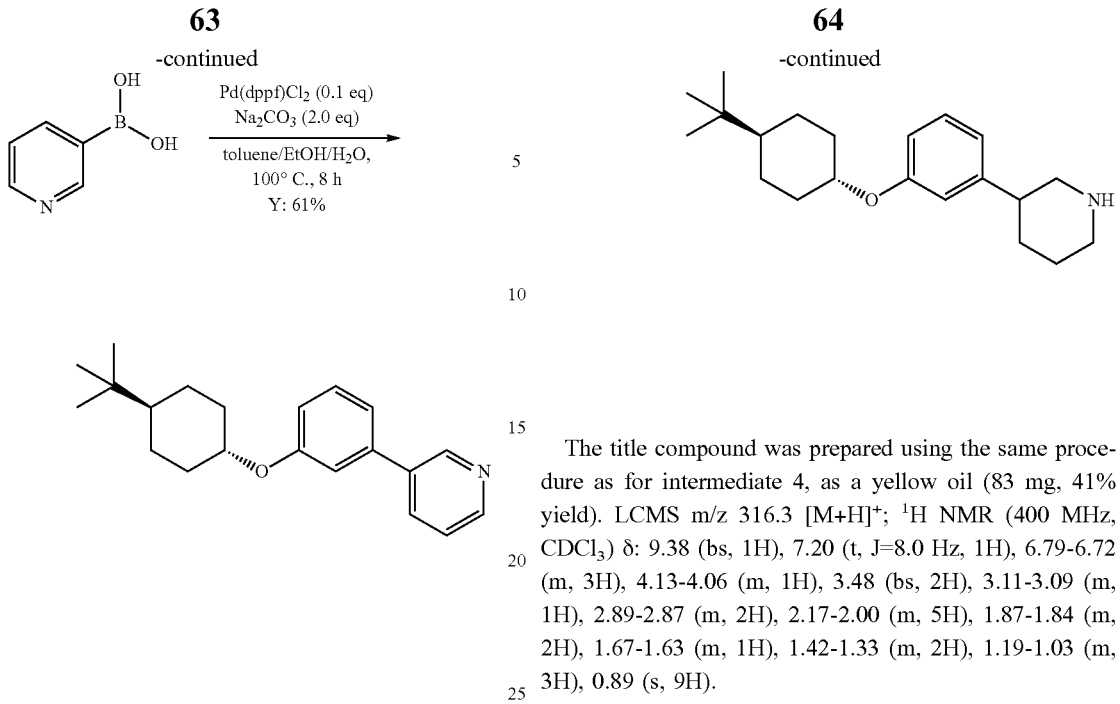

The title compound was prepared using the same procedure as for intermediate 3, as a yellow oil (200 mg, 61% yield). LCMS m/z 310.2 [M+H]$^+$; $^1$H NMR (400 MHz, CDCl$_3$) δ: 8.84 (d, J=2.0 Hz, 1H), 8.59-8.58 (m, 1H), 7.87-7.85 (m, 1H), 7.38-7.34 (m, 2H), 7.14-7.10 (m, 2H), 6.94-6.93 (m, 1H), 4.21-4.16 (m, 1H), 2.25-2.21 (m, 2H), 1.90-1.86 (m, 2H), 1.44-1.38 (m, 2H), 1.17-1.08 (m, 3H), 0.89 (s, 9H).

The title compound was prepared using the same procedure as for intermediate 4, as a yellow oil (83 mg, 41% yield). LCMS m/z 316.3 [M+H]$^+$; $^1$H NMR (400 MHz, CDCl$_3$) δ: 9.38 (bs, 1H), 7.20 (t, J=8.0 Hz, 1H), 6.79-6.72 (m, 3H), 4.13-4.06 (m, 1H), 3.48 (bs, 2H), 3.11-3.09 (m, 1H), 2.89-2.87 (m, 2H), 2.17-2.00 (m, 5H), 1.87-1.84 (m, 2H), 1.67-1.63 (m, 1H), 1.42-1.33 (m, 2H), 1.19-1.03 (m, 3H), 0.89 (s, 9H).

Example 7

3-(3-(3-((trans-4-(tert-Butyl)cyclohexyl)oxy)phenyl)piperidin-1-yl)propanoic acid (Compound 18)

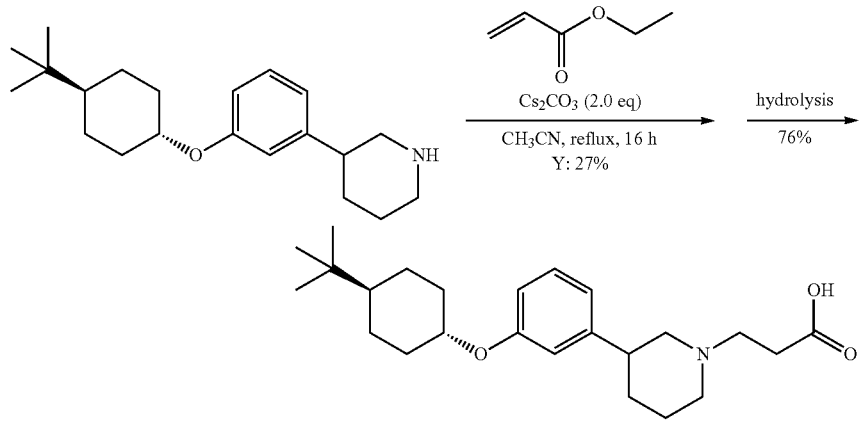

Intermediate 13: 3-(3-((trans-4-(tert-Butyl)cyclohexyl)oxy)phenyl)piperidine

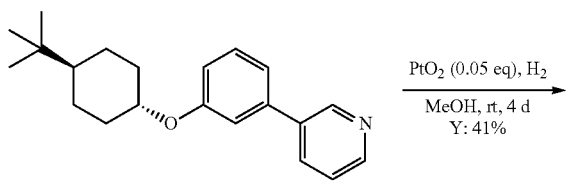

Using the same procedure as for intermediate 5, ethyl 3-(3-(3-((trans-4-(tert-butyl)cyclohexyl)oxy)phenyl)piperidin-1-yl)propanoate as a yellow oil (237 mg, 62% yield). LCMS m/z 416.3 [M+H]$^+$; $^1$H NMR (400 MHz, CDCl$_3$) δ: 7.15 (t, J=8.0 Hz, 1H), 6.75-6.67 (m, 3H), 4.11-4.02 (m, 3H), 3.68-3.59 (m, 2H), 3.36-3.26 (m, 2H), 3.13-3.07 (m, 1H), 2.83-2.80 (m, 2H), 2.64-2.54 (m, 2H), 2.11-1.96 (m, 5H), 1.80-1.78 (m, 2H), 1.60-1.56 (m, 1H), 1.36-1.26 (m, 2H), 1.17 (t, J=8.0 Hz, 3H), 1.11-0.96 (m, 3H), 0.85 (s, 9H).

Using standard hydrolysis condition, the title compound was obtained as a yellow oil (142 mg, 76% yield). LCMS m/z 388.3 [M+H]$^+$; $^1$H NMR (400 MHz, DMSO-d$_6$) δ: 7.22 (t, J=8.4 Hz, 1H), 6.83-6.79 (m, 3H), 4.22-4.20 (m, 1H), 3.46-3.42 (m, 2H), 3.26 (t, J=7.6 Hz, 2H), 3.04-2.89 (m, 3H), 2.79-2.74 (m, 2H), 2.12-2.09 (m, 2H), 1.90-1.77 (m, 5H), 1.66-1.64 (m, 1H), 1.30-1.03 (m, 5H), 0.86 (s, 9H).

Example 8

4-(3-(3-((trans-4-(tert-Butyl)cyclohexyl)oxy)phenyl)piperidin-1-yl)butanoic acid (Compound 19)

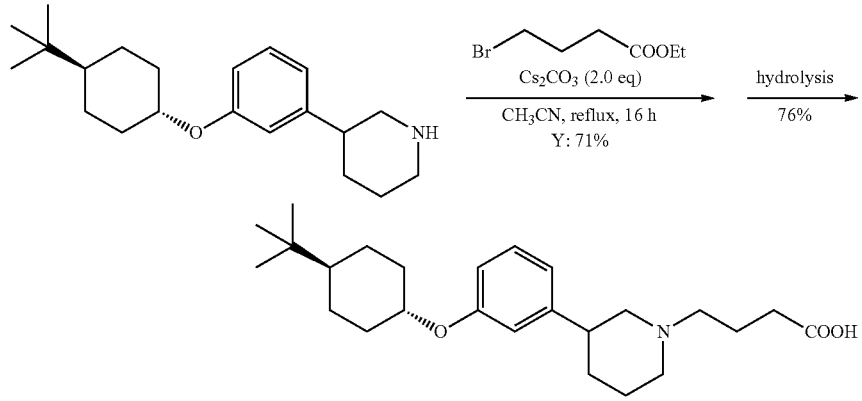

Using the same procedure as for intermediate 6, ethyl 4-(3-(3-((trans-4-(tert-butyl)cyclohexyl)oxy)phenyl)piperidin-1-yl)butanoate was obtained as a yellow oil (267 mg, 71% yield). LCMS m/z 430.3 [M+H]+; $^1$H NMR (400 MHz, CDCl$_3$) δ: 7.15 (t, J=8.0 Hz, 1H), 6.75-6.68 (m, 3H), 4.08-4.02 (m, 3H), 3.70-3.61 (m, 2H), 3.15-3.01 (m, 3H), 2.59-2.54 (m, 2H), 2.35 (t, J=6.4 Hz, 2H), 2.12-1.95 (m, 7H), 1.81-1.78 (m, 2H), 1.59-1.55 (m, 1H), 1.36-1.26 (m, 2H), 1.17 (t, J=7.2 Hz, 3H), 1.12-0.99 (m, 3H), 0.85 (s, 9H).

Using standard hydrolysis condition the title compound was obtained as a yellow oil (117 mg, 76% yield). LCMS m/z 402.3 [M+H]+; $^1$H NMR (400 MHz, DMSO-d$_6$) δ: 7.21 (t, J=8.4 Hz, 1H), 6.83-6.79 (m, 3H), 4.22-4.19 (m, 1H), 3.41-3.35 (m, 2H), 2.98-2.91 (m, 4H), 2.77-2.76 (m, 1H), 2.31 (t, J=7.2 Hz, 2H), 2.12-2.09 (m, 2H), 1.91-1.77 (m, 7H), 1.30-1.28 (m, 1H), 1.26-1.03 (m, 5H), 0.86 (s, 9H).

Intermediate 14: 3-(4-(Octyloxy)phenyl)cyclohex-2-enone

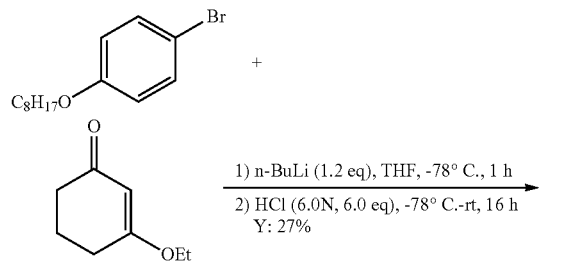

To a stirred solution of 1-bromo-4-(octyloxy)benzene (1.4 g, 4.94 mmol, 1.0 eq) in anhydrous THF (25 mL) was added dropwise n-BuLi (3.7 mL, 5.93 mmol, 1.2 eq) at −78° C. under N$_2$. After addition, the mixture was allowed to stir for 1 h. 3-Ethoxycyclohex-2-enone (761 mg, 5.43 mmol, 1.1 eq) was then added. The resulting mixture was allowed to stir for additional 1 h, and the reaction was then quenched with dilute HCl (6.0 N, 4.9 mL, 29.4 mmol, 6.0 eq), the resulting solution was allowed to warm up to rt and stir for 16 h. The mixture was extracted with EtOAc (50 mL×3). The combined extracts were washed with brine (30 mL), dried over anhydrous Na$_2$SO$_4$, and concentrated in vacuo. The residue was purified by column chromatography on silica gel (petroleum ether/EtOAc=10:1) to give the title compound as a yellow solid (400 mg, 27% yield). LCMS m/z 301.1 [M+1]+.

Intermediate 15: 3-Ethoxycyclohex-2-enone

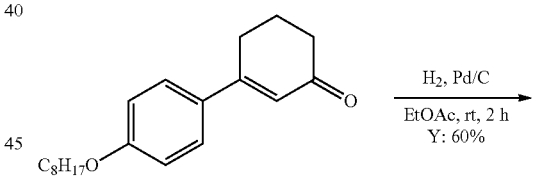

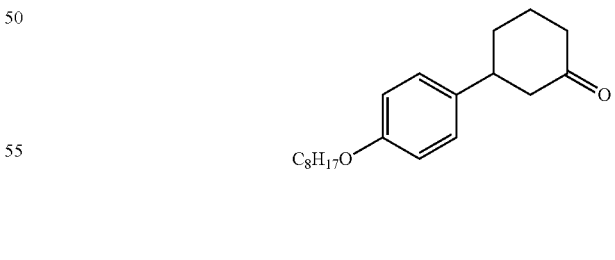

A mixture of 3-(4-(octyloxy)phenyl)cyclohex-2-enone (250 mg, 0.83 mmol, 1.0 eq) and Pd/C (50 mg, 0.17 mmol, 0.2 eq) in EtOAc (2 mL) was purged with H$_2$ for three times and then stirred at rt for 2 h under H$_2$ atmosphere. The mixture was then filtered, and the filtrate was concentrated in vacuo to give the title compound as a white solid (150 mg, 60% yield), which was used in the next step without further purification. LCMS m/z 303.2 [M+1]+.

Intermediate 16: Ethyl 1-(3-(4-(octyloxy)phenyl) cyclohexyl)piperidine-4-carboxylate

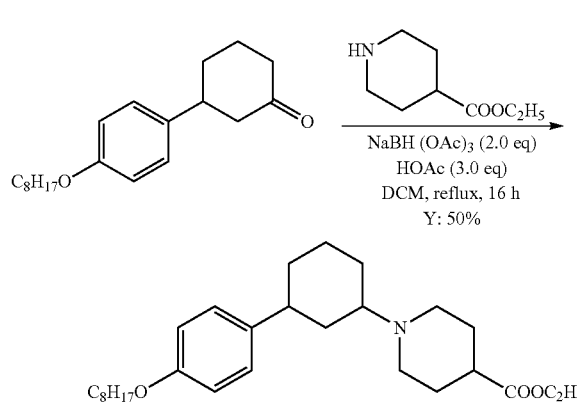

A mixture of 3-(4-(octyloxy)phenyl)cyclohexanone (150 mg, 0.50 mmol, 1.0 eq), ethyl piperidine-4-carboxylate (94 mg, 0.60 mmol, 1.2 eq) and HOAc (90 mg, 1.5 mmol, 3.0 eq) in DCM (5 mL) was heated to reflux for 30 min. Then NaBH(OAc)$_3$ (212 mg, 1.0 mmol, 2.0 eq) was added and the mixture was reflux for another 16 h. After cooling down to rt, the reaction was quenched with saturated aqueous NaHCO$_3$ (1 mL) and the mixture was adjusted to pH=8 with saturated aqueous NaHCO$_3$. The resultant mixture was diluted with DCM (20 mL) and washed with H$_2$O (10 mL×3), dried over anhydrous Na$_2$SO$_4$. The organic phase was concentrated in vacuo and purified by prep-HPLC (MeOH/H$_2$O from 30% to 95%, containing 0.05% TFA) to give the title compound as a white solid (110 mg, 50% yield). LCMS m/z 444.2 [M+1]$^+$.

Example 9

1-(3-(4-(octyloxy)phenyl)cyclohexyl)piperidine-4-carboxylic acid (Compound 16)

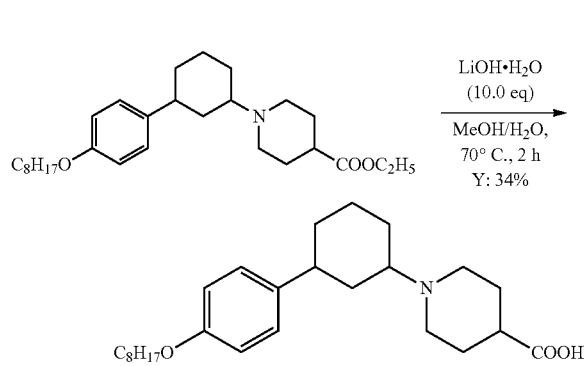

Using standard hydrolysis condition, and purified by prep-HPLC (MeOH/H$_2$O from 30% to 95%, containing 0.05% TFA), the title compound was obtained as a white solid (35 mg, 34% yield). LCMS m/z 416.4 [M+1]$^+$; $^1$HNMR (400 MHz, CD$_3$OD) δ: 7.27-7.16 (m, 2H), 6.90-6.84 (m, 2H), 3.97-3.93 (m, 2H), 3.49 (bs, 2H), 3.14-3.06 (m, 3H), 2.68-2.38 (m, 2H), 2.20-1.57 (m, 12H), 1.49-1.31 (m, 12H), 0.93-0.90 (m, 3H).

Intermediate 17: 3-(4-(trans-4-tert-butylcyclohexyloxy)phenyl)cyclohex-2-enone

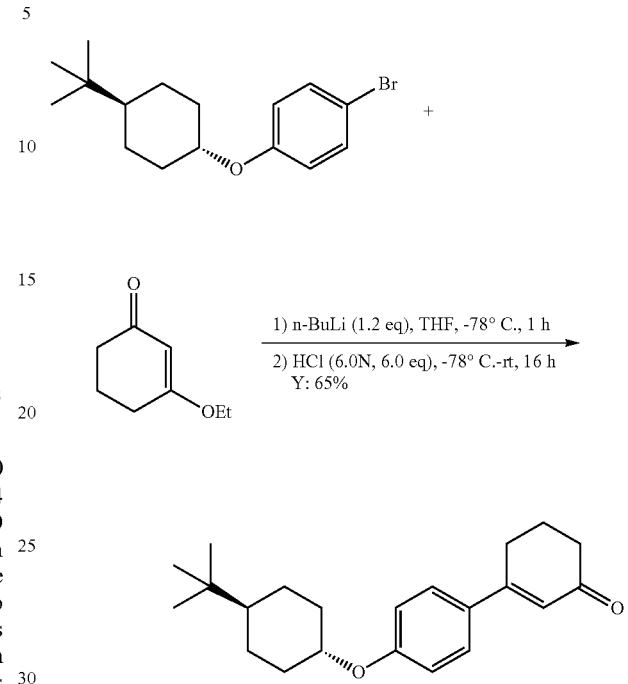

3-(4-(trans-4-tert-Butylcyclohexyloxy)phenyl)cyclohex-2-enone was prepared using the same condition as that for the synthesis of 3-(4-(octyloxy)phenyl)cyclohex-2-enone in intermediate 14. The title compound was obtained as a yellow solid (1.27 g, 65% yield). LCMS m/z 327.2 [M+1]$^+$.

Intermediate 18: 3-(4-(trans-4-tert-Butylcyclohexyloxy)phenyl)cyclohexanone

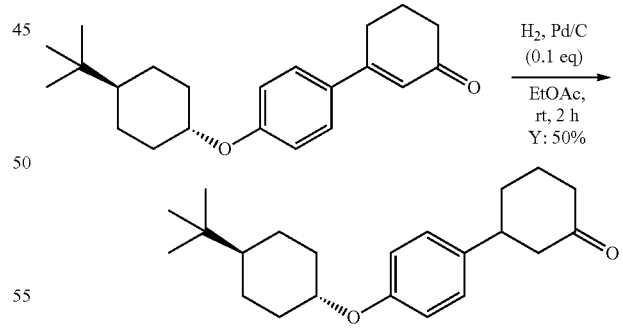

3-(4-(trans-4-tert-Butylcyclohexyloxy)phenyl)cyclohexanone prepared using the same condition as that for the synthesis of 3-ethoxycyclohex-2-enone in intermediate 15. The title compound was obtained as a white solid (220 mg, 50% yield). LCMS m/z 329.1 [M+1]$^+$; $^1$HNMR (400 MHz, CDCl$_3$) δ: 7.11-7.09 (m, 2H), 6.86-6.84 (m, 2H), 4.12-4.04 (m, 1H), 2.98-2.91 (m, 1H), 2.59-2.34 (m, 4H), 2.20-2.04 (m, 4H), 1.87-1.73 (m, 4H), 1.42-1.33 (m, 2H), 1.17-1.02 (m, 3H), 0.87 (s, 9H).

Intermediate 19: Ethyl 1-(3-(4-(trans-4-tert-butylcyclohexyloxy)phenyl)cyclohexyl)piperidine-4-carboxylate

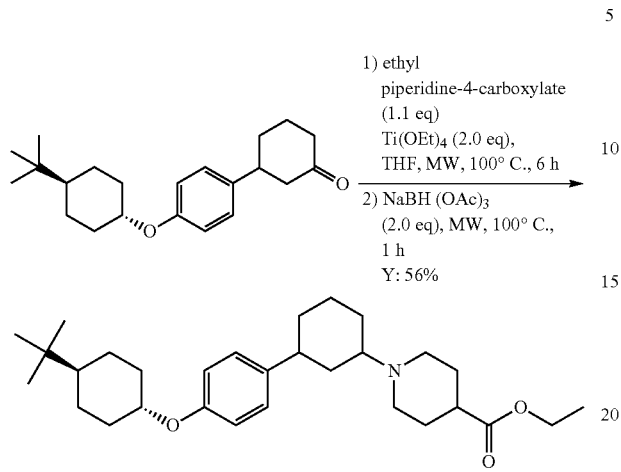

Ethyl 1-(3-(4-(trans-4-tert-butylcyclohexyloxy)phenyl)cyclohexyl)piperidine-4-carboxylate was prepared using the same condition as that for the synthesis of 1-(3-(4-(octyloxy)phenyl)cyclohexyl)piperidine-4-carboxylic acid in intermediate 16. The title compound was obtained as a yellow solid (90 mg, 56% yield). LCMS m/z 470.1 [M+1]$^+$.

Example 10

1-(3-(4-(trans-4-tert-butylcyclohexyloxy)phenyl)cyclohexyl)piperidine-4-carboxylic acid (Compound 11)

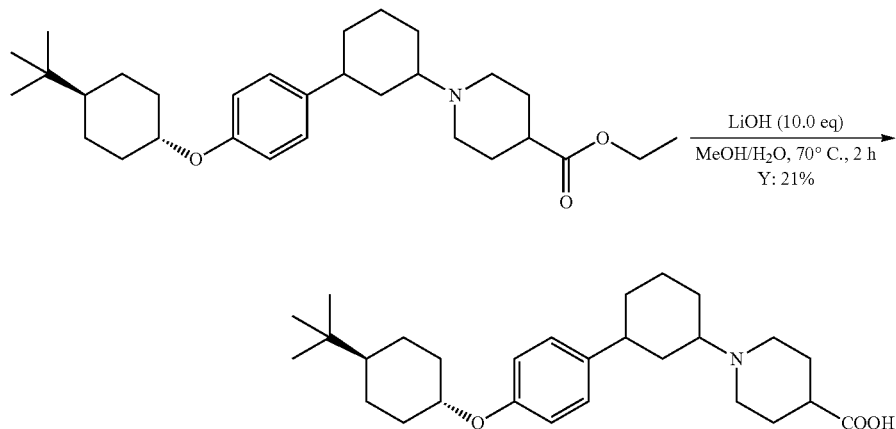

Using standard hydrolysis condition, the title compound was obtained as a yellow solid (20 mg, 21% yield). LCMS m/z 442.3 [M+1]$^+$; $^1$HNMR (400 MHz, CD$_3$OD) δ: two isomers, 7.26-7.15 (m, 2H), 6.89-6.83 (m, 2H), 4.14-4.13 (m, 1H), 3.62-3.46 (m, 2H), 3.39-3.36 (m, 0.37H), 3.27-3.22 (m, 1.63H), 3.17-3.06 (m, 1.81H), 2.87-2.85 (m, 0.24H), 2.67-2.59 (m, 1H), 2.45-1.55 (m, 16H), 1.39-1.05 (m, 5H), 0.90 (s, 9H).

Intermediate 20: 2-Chloro-5-(octyloxy)pyridine

A mixture of 1-bromooctane (390 mg, 3.0 mmol, 1.0 eq), 1-bromooctane (690 mg, 3.6 mmol, 1.2 eq) and K$_2$CO$_3$ (840 mg, 6.0 mmol, 2.0 eq) in DMF (10 mL) was heated to 80° C. and stirred for 3 h. After cooling down to rt, the mixture was diluted with H$_2$O (50 mL) and extracted with EA (50 mL×3). The extracts were combined, dried over anhydrous Na$_2$SO$_4$, and concentrated under reduced pressure. The residue was purified by silica gel column chromatography (petroleum ether/EtOAc=50:1) to give the title compound as a yellow oil (570 mg, 65% yield). LCMS: m/z 242.1 [M+H]$^+$.

Intermediate 21: tert-Butyl 3-(5-(octyloxy)pyridin-2-ylamino)piperidine-1-carboxylate

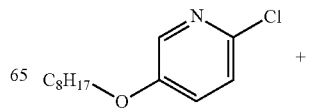

-continued

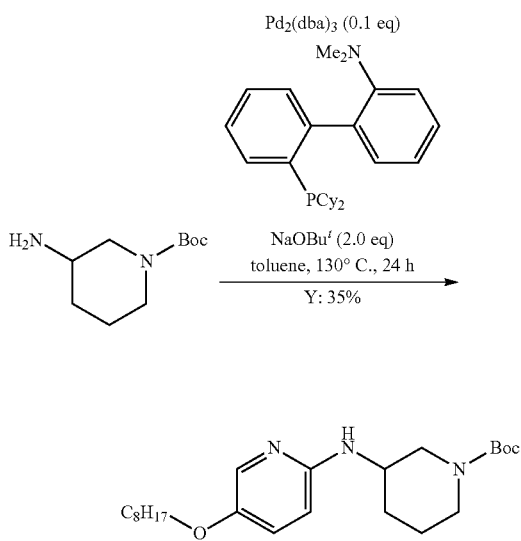

A stirred mixture of 2-chloro-5-(octyloxy)pyridine (240 mg, 1.0 mmol, 1.0 eq), tert-butyl 3-aminopiperidine-1-carboxylate (250 mg, 1.2 mmol, 1.2 eq) and NaO$^t$Bu (180 mg, 2.0 mmol, 2.0 eq) in anhydrous toluene (5 mL) was purged with $N_2$ for 5 minutes, 2'-(dicyclohexylphosphino)-N,N-dimethylbiphenyl-2-amine (80 mg, 0.2 mmol, 0.2 eq) and Pd$_2$(dba)$_3$ (92 mg, 0.1 mmol, 0.1 eq) were then added. The mixture was purged with $N_2$ for three times again and heated to 130° C. for 24 h. After cooling down to rt, the mixture was then filtered, and the filtrate was concentrated in vacuo. The residue was purified by prep-TLC (petroleum ether/EtOAc=4:1) to give the title compound as a yellow oil (140 mg, 35% yield). LCMS: m/z 406.4 [M+H]$^+$. $^1$HNMR (400 MHz, CDCl$_3$) δ: 7.90 (d, J=3.2 Hz, 1H), 7.13 (dd, J=9.2, 3.2 Hz, 1H), 6.68 (d, J=9.2 Hz, 1H), 4.86 (bs, 1H), 3.91 (t, J=6.4 Hz, 2H), 3.79 (bs, 1H), 3.59-3.21 (m, 4H), 1.84-1.71 (m, 5H), 1.62 (bs, 3H), 1.44 (bs, 11H), 1.31 (bs, 6H), 0.88 (t, J=6.8 Hz, 3H).

Intermediate 22: 5-(Octyloxy)-N-(piperidin-3-yl)pyridin-2-amine

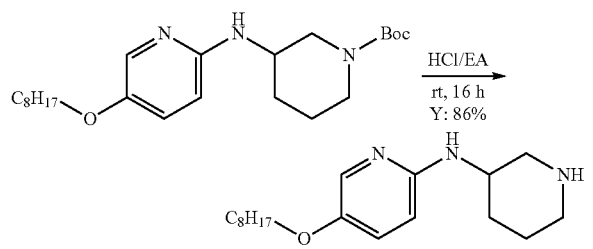

A mixture of tert-utyl 3-(5-(octyloxy)pyridin-2-ylamino) piperidine-1-carboxylate (400 mg, 1.0 mmol, 1.0 eq) in a solution of HCl in EtOAc (3 mL, sat.) was stirred at rt for 16 h. The reaction solution was concentrated to yield a crude product, as yellow oil (260 mg, 86% yield), which was used for next step without further purification. LCMS: m/z 306.3 [M+H]$^+$.

Intermediate 23: Ethyl 3-(3-(5-(octyloxy)pyridin-2-ylamino)piperidin-1-yl)propanoate

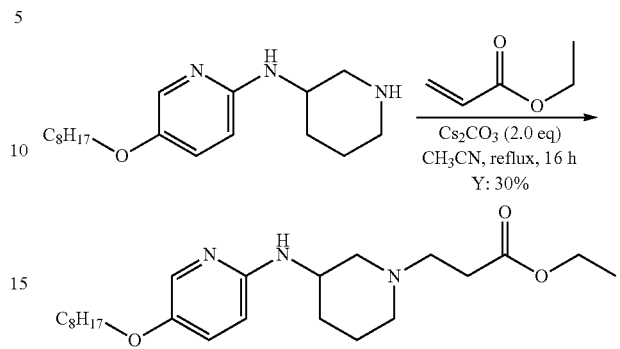

A stirred mixture of 5-(octyloxy)-N-(piperidin-3-yl)pyridin-2-amine (240 mg, 0.8 mmol, 1.0 eq), ethyl acrylate (120 mg, 1.2 mmol, 1.5 eq) and Cs$_2$CO$_3$ (510 mg, 1.6 mmol, 2.0 eq) in CH$_3$CN (2 mL) was heated to reflux for 16 h. After cooling down to rt, the mixture was diluted with H$_2$O (20 mL) and extracted with EtOAc (20 mL×3). The organic layers were combined, dried with Na$_2$SO$_4$ and filtered. The filtrate was concentrated in vacuo, and the residue was purified by prep-TLC (petroleum ether/EtOAc=1:1) to give the title compound as a yellow oil (100 mg, 30% yield). LCMS: m/z 406.4 [M+H]$^+$; $^1$HNMR (400 MHz, CDCl$_3$) δ: 7.78 (d, J=3.2 Hz, 1H), 7.08 (dd, J=9.2, 3.2 Hz, 1H), 6.37 (d, J=9.2 Hz, 1H), 4.86 (bs, 1H), 4.15 (q, J=7.6 Hz, 2H), 3.89 (t, J=6.4 Hz, 2H), 3.79 (bs, 1H), 2.71-2.68 (m, 3H), 2.51-2.34 (m, 5H), 1.77-1.70 (m, 4H), 1.55 (bs, 2H), 1.43 (bs, 2H), 1.31-1.24 (bs, 11H), 0.90-0.87 (m, 3H).

Example 11

3-(3-(5-(Octyloxy)pyridin-2-ylamino)piperidin-1-yl)propanoic acid (Compound 12)

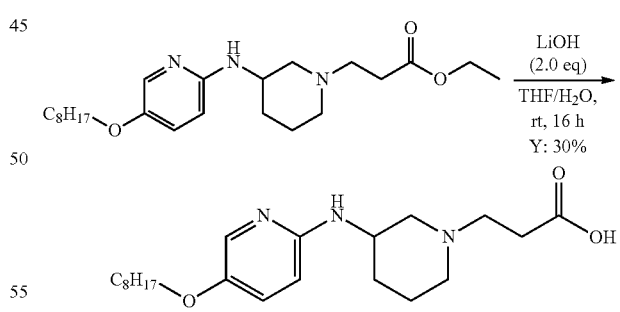

Using standard hydrolysis condition and purified by prep-HPLC (MeOH and H$_2$O with 0.05% TFA as mobile phase), the title compound was obtained as a yellow oil (30 mg, 30% yield). LCMS: m/z 378.4 [M+H]$^+$; $^1$H NMR (400 MHz, CD$_3$OD) δ: 7.70 (dd, J=9.2, 2.8 Hz, 1H), 7.57 (d, J=2.8 Hz, 1H), 7.07 (d, J=9.2 Hz, 1H), 4.17-4.09 (m 1H), 3.99 (t, J=6.4 Hz, 2H), 3.73 (bs, 1H), 3.54-3.41 (m, 3H), 3.10 (bs, 2H), 2.87 (t, J=7.2 Hz, 2H), 2.19-2.11 (m, 2H), 2.02-1.91 (m, 1H), 1.83-1.70 (m, 3H), 1.52-1.45 (m, 2H), 1.37-1.32 (m, 8H), 0.91 (t, J=6.8 Hz, 3H).

Intermediate 24: 5-(trans-4-tert-butylcyclohexyloxy)-2-chloropyridine

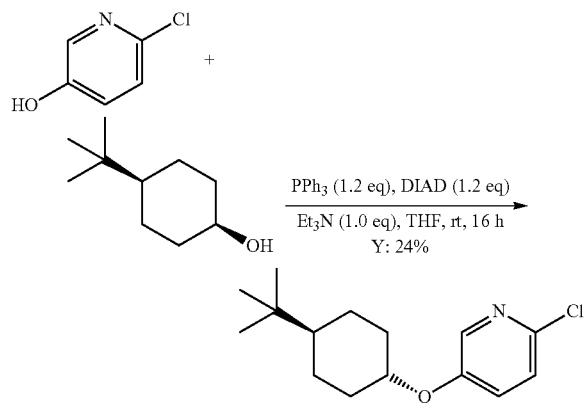

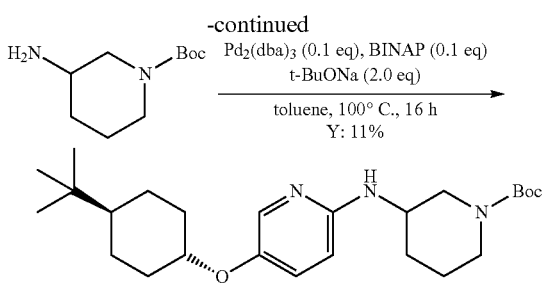

To a mixture of 6-chloropyridin-3-ol (258 mg, 2.0 mmol, 1.0 eq), cis-4-tert-butylcyclohexanol (374 mg, 2.4 mmol, 1.2 eq), PPh₃ (629 mg, 2.4 mmol, 1.2 eq) and Et₃N (202 mg, 2.0 mmol, 1.0 eq) in THF (5 mL) was added dropwise DIAD (485 mg, 2.4 mmol, 1.2 eq) at 0° C. The reaction mixture was stirred at rt for 16 h. And then, the solvent was removed under reduced pressure to give the crude title product, which was purified by column chromatography on silica gel, eluting with petroleum ether/EtOAc (20/1) to give the title compound as a white solid (150 mg, 24% yield). LCMS: m/z 268.1 [M+H]⁺. ¹HNMR (400 MHz, CDCl₃) δ: 8.03 (d, J=2.4 Hz, 1H), 7.21-7.15 (m, 2H), 4.13-4.07 (m, 1H), 2.19-2.15 (m, 2H), 1.89-1.86 (m, 2H), 1.44-1.35 (m, 2H), 1.13-1.05 (m, 3H), 0.88 (s, 9H).

Intermediate 25: tert-butyl 3-(5-(trans-4-tert-butyl-cyclohexyloxy)pyridin-2-ylamino)piperidine-1-carboxylate

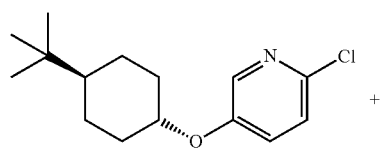

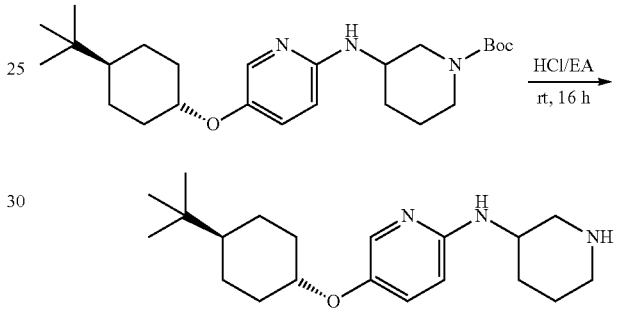

Using the same condition as that for the synthesis of tert-Butyl 3-(5-(octyloxy)pyridin-2-ylamino)piperidine-1-carboxylate in intermediate 21, the title compound was obtained as a yellow solid (96 mg, 11% yield). LCMS m/z 432.3 [M+H]⁺.

Intermediate 26: 5-(trans-4-tert-butylcyclohexyloxy)-N-(piperidin-3-yl)pyridin-2-amine Using the same condition as that for the synthesis of 5-(octyloxy)-N-(piperidin-3-yl)pyridin-2-amine in intermediate 22, the title compound was obtained as a yellow oil (72 mg, 96% yield). LCMS m/z 332.3 [M+H]⁺.

Example 12

3-(3-(5-(trans-4-tert-butylcyclohexyloxy)pyridin-2-ylamino)piperidin-1-yl)propanoic acid (Compound 13)

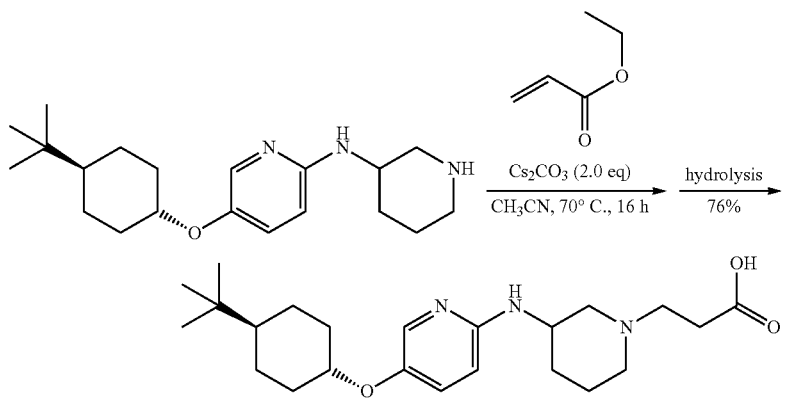

Using the same procedure as for intermediate 23, ethyl 3-(3-(5-(trans-4-tert-butylcyclohexyloxy)pyridin-2-ylamino)piperidin-1-yl)propanoate was obtained as a white solid (56 mg, 39% yield). LCMS m/z 432.3 [M+H]+.

Using standard hydrolysis condition, the title compound was obtained as a yellow oil (64 mg, 76% yield). LCMS m/z 404.3 [M+H]+; ¹HNMR (400 MHz, CDCl₃) δ: 7.71 (m, 1H), 7.62 (d, J=2.4 Hz, 1H), 7.03 (m, 1H), 4.13 (m, 2H), 3.73 (s, 1H), 3.52-3.42 (m, 3H), 3.15-3.02 (m, 2H), 2.87 (t, J=7.0 Hz, 2H), 2.19-2.11 (m, 4H), 1.98-1.88 (m, 3H), 1.72-1.67 (m, 1H), 1.42-1.34 (m, 2H), 1.25-1.09 (m, 3H), 0.90 (s, 9H).

Intermediate 27: tert-Butyl 3-((4-((trans-4-(tert-butyl)cyclohexyl)oxy)phenyl)amino)piperidine-1-carboxylate

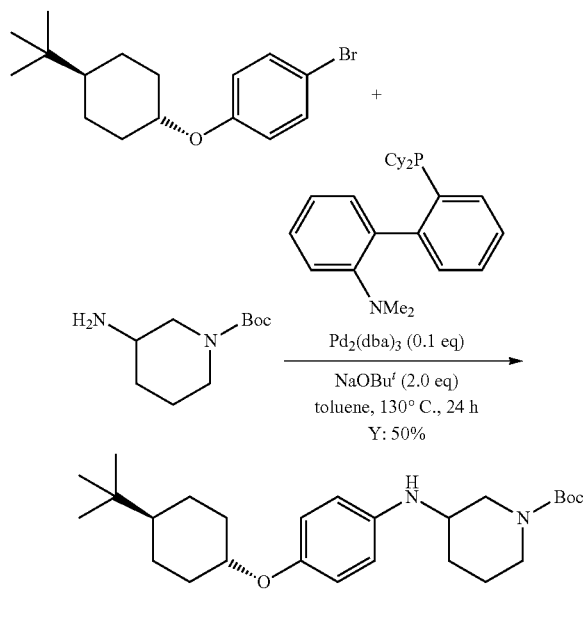

Intermediate 28: N-(4-((trans-4-(tert-butyl)cyclohexyl)oxy)phenyl)piperidin-3-amine

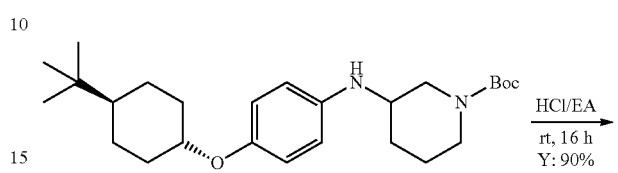

tert-Butyl 3-((4-((trans-4-(tert-butyl)cyclohexyl)oxy)phenyl)amino)piperidine-1-carboxylate (430 mg, 1.0 mmol, 1.0 eq) was dissolved in a solution of HCl in EtOAc (sat. 3 mL) and stirred at rt for 16 h. The mixture was concentrated to give the crude title compound as a yellow oil (300 mg, 90% yield), which was used for next step without further purification. LCMS: m/z 331.3 [M+H]+.

Example 13

3-(3-((4-((trans-4-(tert-Butyl)cyclohexyl)oxy)phenyl)amino)piperidin-1-yl)propanoic acid (Compound 14)

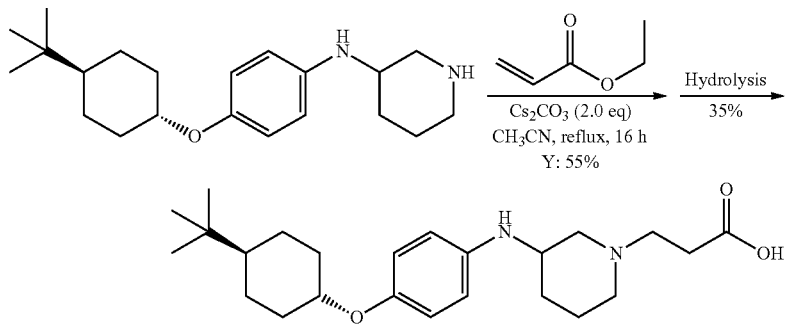

1-Bromo-4-((trans-4-(tert-butyl)cyclohexyl)oxy)benzene (620 mg, 2.0 mmol, 1.0 eq), tert-butyl 3-aminopiperidine-1-carboxylate (500 mg, 2.4 mmol, 1.2 eq) and NaOBuᵗ (360 mg, 4.0 mmol, 2.0 eq) were dissolved in anhydrous toluene (5 mL). The mixture was purged with N₂ for 5 minutes, 2'-(dicyclohexylphosphino)-N,N-dimethyl-[1,1'-biphenyl]-2-amine (160 mg, 0.4 mmol, 0.2 eq) and Pd₂(dba)₃ (185 mg, 0.2 mmol, 0.1 eq) were added thereto. The stirred mixture was purged with N₂ for three times, and then heated to 130° C. for 24 h. After cooling down to rt, the mixture was then filtered, and the filtrate was concentrated in vacuo. The residue was purified by prep-TLC (PE/EA=4:1) to give the title compound as a yellow oil (440 mg, 50% yield). LCMS: m/z 431.4 [M+H]+.

Using the same procedure as for intermediate 5, ethyl 3-(3-((4-((trans-4-(tert-butyl)cyclohexyl)oxy)phenyl)amino)piperidin-1-yl)propanoate was obtained as a yellow oil (110 mg, 55% yield). LCMS: m/z 431.4 [M+H]+.

Using standard hydrolysis condition, the title compound as a yellow oil (40 mg, 35% yield). LCMS: m/z 403.4 [M+H]+; ¹H NMR (400 MHz, CD₃OD) δ: 6.66 (d, J=8.4 Hz, 2H), 6.55 (d, J=8.4 Hz, 2H), 3.89-3.81 (m, 1H), 3.56 (bs, 1H), 3.41-3.28 (m, 4H), 2.95 (bs, 1H), 2.80-2.67 (m, 3H), 2.04-1.99 (m, 4H), 1.75 (bs, 3H), 1.48 (bs, 1H), 1.24-1.15 (m, 2H), 1.08-0.95 (m, 3H), 0.78 (s, 9H)

Intermediate 29: tert-Butyl 4-(4-(octyloxy)phenyl)piperazine-1-carboxylate

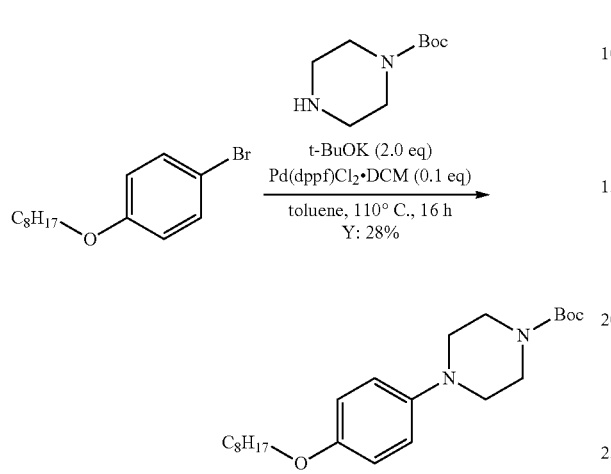

A mixture of 1-bromo-4-(octyloxy)benzene (568 mg, 2.0 mmol, 1.0 eq), tert-butyl piperazine-1-carboxylate (372 mg, 2.0 mmol, 1.0 eq), t-BuOK (448 mg, 4.0 mmol, 2.0 eq) and Pd(dppf)Cl$_2$.DCM (163 mg, 0.2 mmol, 0.1 eq) in toluene (5 mL) was stirred at 110° C. for 16 h. After cooling down to rt, the mixture was filtrated and the filtrate was concentrated in vacuo. The residue was purified by column chromatography (PE/EA=8/1) to give the title compound as a white solid (218 mg, 28% yield). LCMS m/z 391.1 [M+1]$^+$.

Intermediate 30: 1-(4-(Octyloxy)phenyl)piperazine

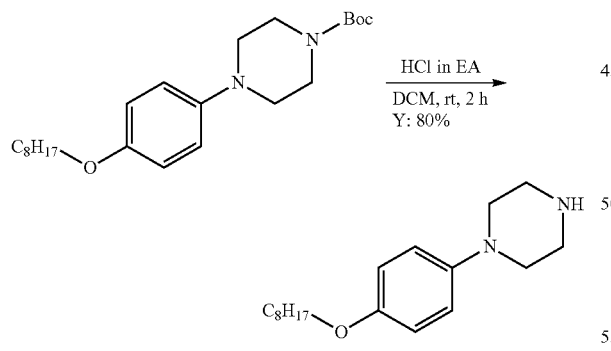

To a solution of tert-butyl 4-(4-(octyloxy)phenyl)piperazine-1-carboxylate (600 mg, 1.54 mmol, 1.0 eq) in DCM (2 mL) was added HCl in EA (4M, 3 mL). Then the mixture was stirred at rt for 2 h. Then the solvent was removed in vacuo to give the title compound as a yellow solid (357 mg, 80% yield), which was used in the next step without further purification. LCMS m/z 291.1 [M+1]$^+$; $^1$HNMR (400 MHz, CDCl$_3$) δ: 6.91-6.83 (m, 4H), 3.92 (t, J=6.8 Hz, 2H), 3.10 (bs, 6H), 2.63 (bs, 2H), 1.80-1.73 (m, 2H), 1.49-1.29 (m, 10H), 0.89 (t, J=6.8 Hz, 3H).

Example 14

3-(4-(4-(Octyloxy)phenyl)piperazin-1-yl)propanoic acid (Compound 7)

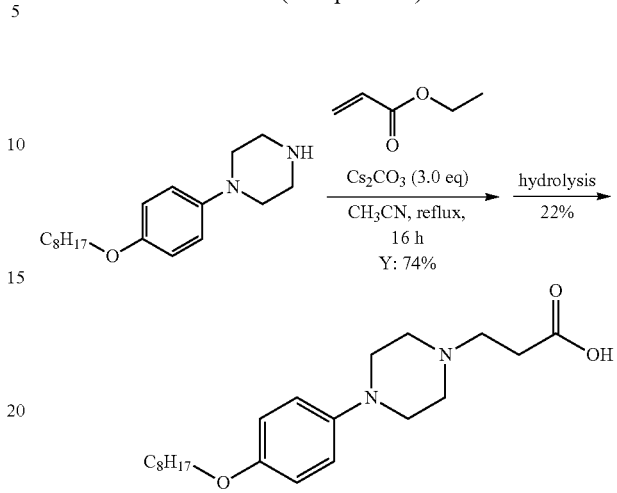

Using the same procedure as for intermediate 5, ethyl 3-(4-(4-(octyloxy)phenyl)piperazin-1-yl)propanoate was obtained as a yellow solid (120 mg, 74% yield), which was used in the next step without further purification. LCMS m/z 391.1 [M+1]$^+$.

Using standard hydrolysis condition, the title compound as a yellow solid (20 mg, 22% yield). LCMS m/z 363.3 [M+1]$^+$; $^1$HNMR (400 MHz, CDCl$_3$) δ: 6.89-6.82 (m, 4H), 3.90 (t, J=6.8 Hz, 2H), 3.18 (bs, 4H), 2.88 (bs, 6H), 2.58-2.55 (m, 2H), 1.78-1.71 (m, 2H), 1.45-1.28 (m, 10H), 0.88 (t, J=6.8 Hz, 3H).

Example 15

4-(4-(4-(Octyloxy)phenyl)piperazin-1-yl)butanoic acid (Compound 8)

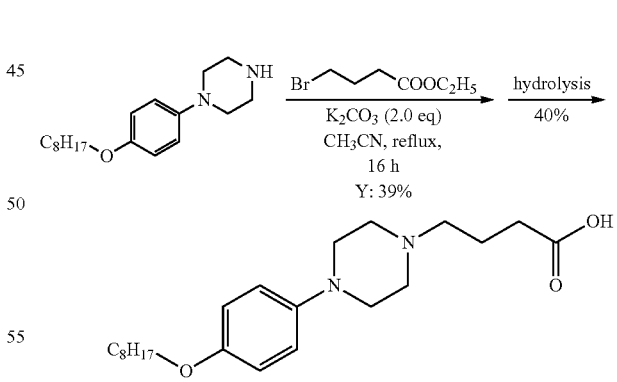

Using the same procedure as for intermediate 6, ethyl 4-(4-(4-(octyloxy)phenyl)piperazin-1-yl)butanoate was obtained as a yellow oil (54 mg, 39% yield). LCMS m/z 405.2 [M+H]$^+$.

Using standard hydrolysis condition, the title compound was obtained as a yellow solid (18 mg, 40% yield). LCMS m/z 377.3 [M+H]$^+$; $^1$H NMR (400 MHz, CD$_3$OD) δ: 6.87-6.85 (m, 2H), 6.76-6.73 (m, 2H), 3.81 (t, J=6.8 Hz, 2H), 3.16 (bs, 8H), 2.96 (t, J=6.4 Hz, 2H), 2.39-2.36 (m, 2H), 1.87-

1.81 (m, 2H), 1.67-1.60 (m, 2H), 1.39-1.32 (m, 2H), 1.25-1.20 (m, 8H), 0.80 (t, J=6.8 Hz, 3H).

Example 16

4-((4-(4-(Octyloxy)phenyl)piperazin-1-yl)methyl)bicyclo[2.2.2]octane-1-carboxylic acid (Compound 9)

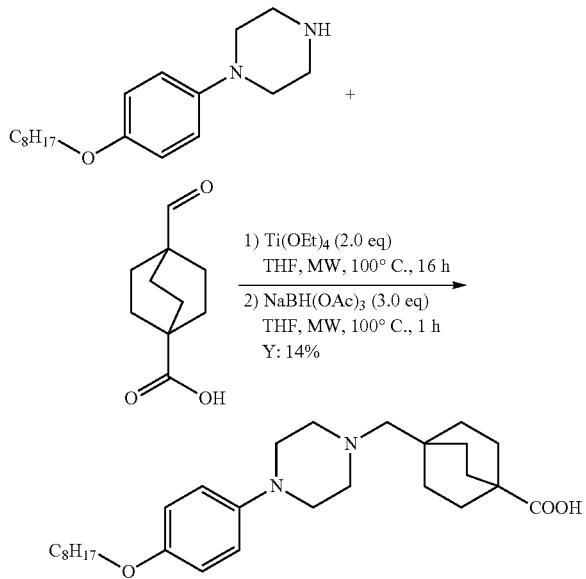

A mixture of 1-(4-(octyloxy)phenyl)piperazine (100 mg, 0.34 mmol, 1.0 eq), (56 mg, 0.31 mmol, 0.9 eq) and Ti(OEt)$_4$ (155 mg, 0.68 mmol, 2.0 eq) in THF (2 mL) was stirred at 100° C. under MW for 16 h. After cooling to rt, NaBH(OAc)$_3$ (216 mg, 1.02 mmol, 3.0 eq) was added and then the mixture was stirred for another 1 h under same condition. After the mixture was cooled to rt once again, the Celite and water (2 mL) were added, the resulting suspension was filtered through Celite and eluted with EA (10 mL). The filtrate was separated, and the aqueous layer was extracted with EA (10 mL×3). The combined organic phase was dried over anhydrous Na$_2$SO$_4$ and concentrated under reduced pressure. The residue was purified by silica gel column chromatography (DCM/MeOH=20/1) to give the title compound (15 mg, 14% yield) as a white solid. LCMS m/z 457.3 [M+H]$^+$; $^1$H NMR (400 MHz, DMSO-d$_6$) δ: 12.01 (bs, 1H), 6.84-6.77 (m, 4H), 3.86 (t, J=6.4 Hz, 2H), 2.95-2.94 (m, 4H), 2.55-2.52 (m, 4H), 2.04 (s, 2H), 1.67-1.63 (m, 8H), 1.41-1.26 (m, 16H), 0.86 (t, J=6.8 Hz, 3H).

Intermediate 31: tert-Butyl 4-(4-((trans-4-(tert-butyl)cyclohexyl)oxy)phenyl)piperazine-1-carboxylate

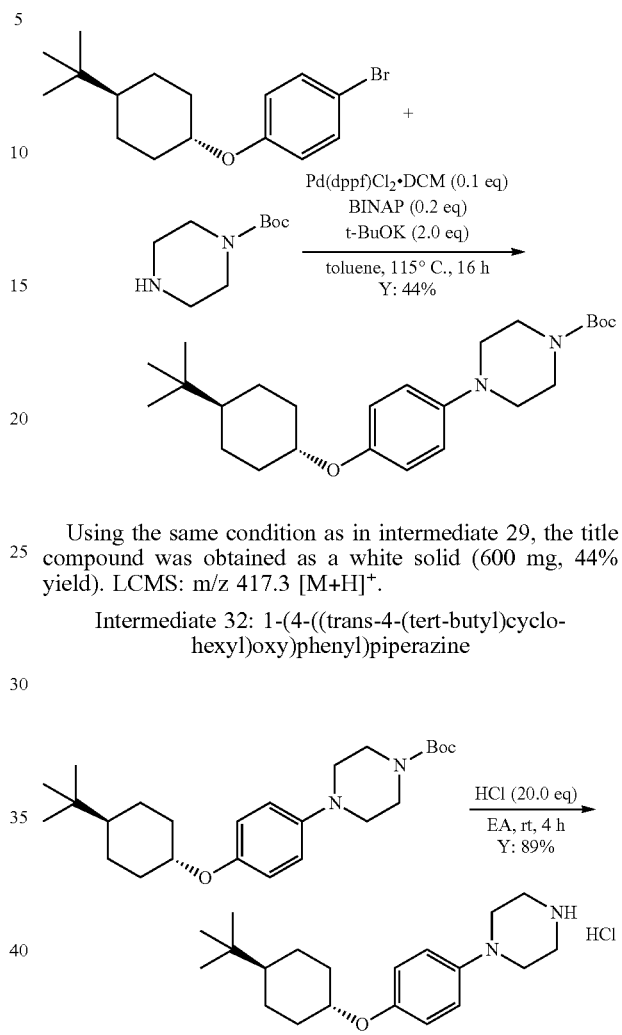

Using the same condition as in intermediate 29, the title compound was obtained as a white solid (600 mg, 44% yield). LCMS: m/z 417.3 [M+H]$^+$.

Intermediate 32: 1-(4-((trans-4-(tert-butyl)cyclohexyl)oxy)phenyl)piperazine

Using the same condition as in intermediate 30, the title compound was obtained as a yellow solid (340 mg, 89% yield). LCMS: m/z 317.0 [M+H]$^+$; $^1$H NMR (400 MHz, DMSO-d$_6$) δ: 6.83-6.77 (m, 4H), 4.05-4.00 (m, 1H), 2.90-2.88 (m, 4H), 2.82-2.79 (m, 4H), 2.08-2.05 (m, 2H), 1.77-1.74 (m, 2H), 1.25-1.01 (m, 5H), 0.84 (s, 9H).

Example 17

3-(4-(4-((trans-4-(tert-Butyl)cyclohexyl)oxy)phenyl)piperazin-1-yl)propanoic acid (Compound 1)

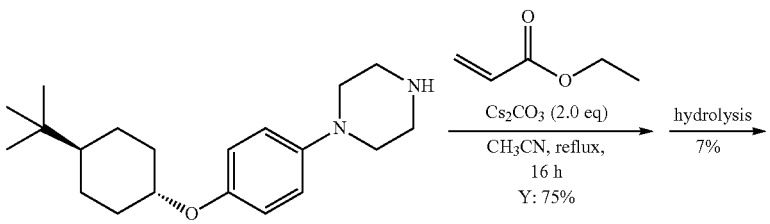

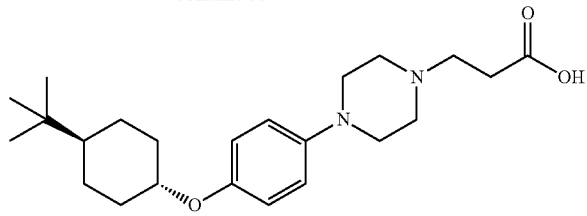

Using the same procedure as for intermediate 5, ethyl 3-(4-(4-((trans-4-(tert-butyl)cyclohexyl)oxy)phenyl)piperazin-1-yl)propanoate was obtained as a yellow solid (120 mg, 75% yield). LCMS: m/z 417.3 [M+H]$^+$; $^1$H NMR (400 MHz, CDCl$_3$) δ: 6.88-6.82 (m, 4H), 4.15 (q, J=6.8 Hz, 2H), 4.01-3.96 (m, 1H), 3.10 (bs, 4H), 2.78-2.55 (m, 7H), 2.17-2.15 (m, 2H), 1.85-1.82 (m, 2H), 1.60 (bs, 1H), 1.39-1.31 (m, 2H), 1.26 (t, J=7.2 Hz, 3H), 1.11-1.03 (m, 3H), 0.86 (s, 9H).

Using standard hydrolysis condition, the title compound was obtained as a yellow solid (5 mg, 7% yield). LCMS: m/z 389.3 [M+H]$^+$; $^1$H NMR (400 MHz, CD$_3$OD) δ: 6.97-6.94 (m, 2H), 6.87-6.85 (m, 2H), 4.10-4.03 (m, 1H), 3.27-3.21 (m, 10H), 2.61-2.57 (m, 2H), 2.18-2.15 (m, 2H), 1.88-1.85 (m, 2H), 1.41-1.30 (m, 1H), 1.25-1.08 (m, 4H), 0.90 (s, 9H).

Example 18

4-(4-(4-((trans-4-(tert-Butyl)cyclohexyl)oxy)phenyl)piperazin-1-yl)butanoic acid (Compound 2)

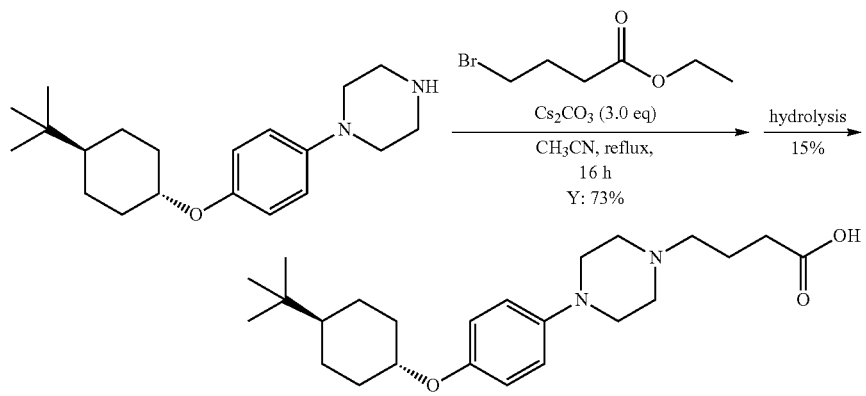

Using the same procedure as for intermediate 6, ethyl 4-(4-(4-((trans-4-(tert-butyl)cyclohexyl)oxy)phenyl)piperazin-1-yl)butanoate was obtained as a yellow solid (100 mg, 73% yield). LCMS: m/z 431.3 [M+H]$^+$; $^1$H NMR (CDCl$_3$, 400 MHz) δ: 6.94-6.92 (m, 2H), 6.88-6.85 (m, 2H), 4.15 (q, J=7.2 Hz, 2H), 4.06-3.99 (m, 1H), 3.70-3.10 (m, 8H), 2.46 (t, J=6.8 Hz, 2H), 2.17-2.08 (m, 6H), 1.87-1.83 (m, 2H), 1.40-1.32 (m, 2H), 1.27 (t, J=7.2 Hz, 3H), 1.15-1.04 (m, 3H), 0.87 (s, 9H).

Using standard hydrolysis condition, the title compound was obtained as a white solid (10 mg, 15% yield). LCMS: m/z 403.3 [M+H]$^+$; $^1$H NMR (400 MHz, CD$_3$OD) δ: 6.97-6.95 (m, 2H), 6.88-6.84 (m, 2H), 4.10-4.04 (m, 1H), 3.27 (bs, 8H), 3.08-3.06 (m, 2H), 2.51-2.48 (m, 2H), 2.18-2.15 (m, 2H), 1.96-1.86 (m, 4H), 1.35-1.30 (m, 2H), 1.19-1.11 (m, 3H), 0.90 (s, 9H).

Example 19

4-((4-(4-((trans-4-(tert-Butyl)cyclohexyl)oxy)phenyl)piperazin-1-yl)methyl)bicyclo[2.2.2]octane-1-carboxylic acid (Compound 10)

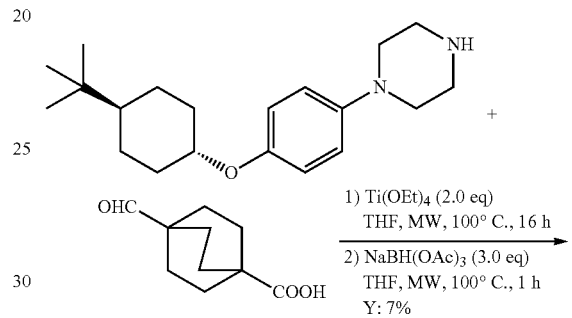

-continued

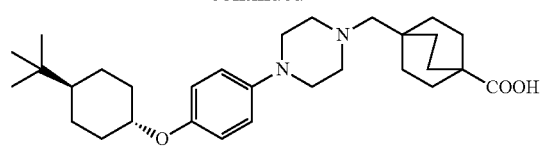

Using the same procedure as for example 16, the title compound was obtained as a white solid (50 mg, 7% yield). LCMS: m/z 483.4 [M+H]$^+$; $^1$H NMR (400 MHz, DMSO-d$_6$) δ: 12.16 (s, 1H), 6.91-6.84 (m, 4H), 4.12-4.05 (m, 1H), 3.55-3.48 (m, 4H), 3.26-3.03 (m, 6H), 2.09-2.05 (m, 2H), 1.78-1.70 (m, 8H), 1.59-1.55 (m, 6H), 1.29-1.20 (m, 2H), 1.16-0.98 (m, 3H), 0.85 (s, 9H).

Intermediate 33: 3-Chloro-6-(octyloxy)pyridazine

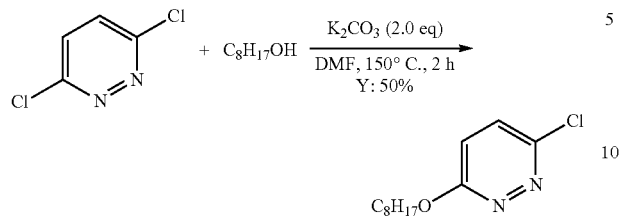

3,6-Dichloropyridazine (450 mg, 3.0 mmol, 1.0 eq), octan-1-ol (450 mg, 3.3 mmol, 1.1 eq) and K$_2$CO$_3$ (840 mg, 6.0 mmol, 2.0 eq) were dissolved in DMF (6 mL). The mixture was heated to 150° C. for 2 h. After cooling down to rt, the mixture was purified by prep-TLC (PE/EA=10/1) to give the title compound as a yellow solid (400 mg, 50% yield). LCMS m/z 243.1 [M+H]$^+$; $^1$H NMR (400 MHz, CDCl$_3$) δ: 7.35 (d, J=9.2 Hz, 1H), 6.94 (d, J=9.2 Hz, 1H), 4.47 (t, J=6.4 Hz, 2H), 1.84-1.77 (m, 2H), 1.48-1.41 (m, 2H), 1.37-1.28 (m, 8H), 0.89 (t, J=6.4 Hz, 3H).

Intermediate 34: tert-Butyl 4-(6-(ctyloxy)pyridazin-3-yl)piperazine-1-carboxylate

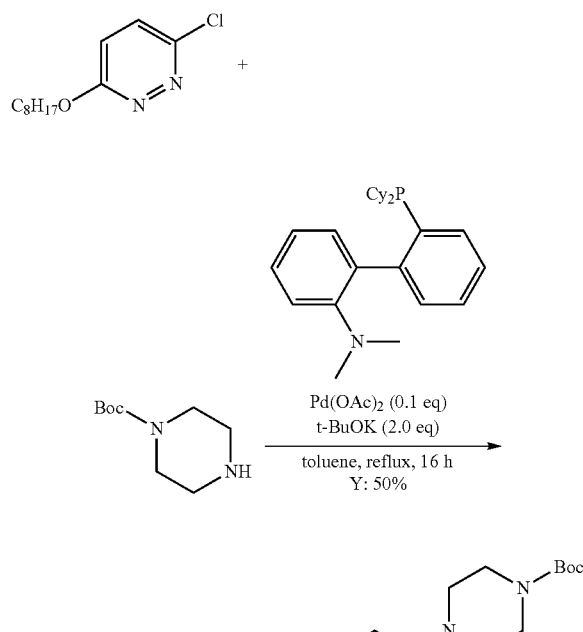

Using the same condition as in intermediate 29, the title compound was obtained as a yellow oil (200 mg, 50% yield). LCMS m/z 393.4 [M+H]$^+$; $^1$H NMR (400 MHz, CDCl$_3$) δ: 7.02 (d, J=9.6 Hz, 1H), 6.85 (d, J=9.6 Hz, 1H), 4.39 (t, J=6.8 Hz, 2H), 3.56 (bs, 4H), 3.49 (bs, 4H), 1.82-1.75 (m, 2H), 1.49 (s, 9H), 1.45-1.39 (m, 2H), 1.30-1.27 (m, 8H), 0.88 (t, J=6.8 Hz, 3H).

Intermediate 35: 3-(Octyloxy)-6-(piperazin-1-yl)pyridazine

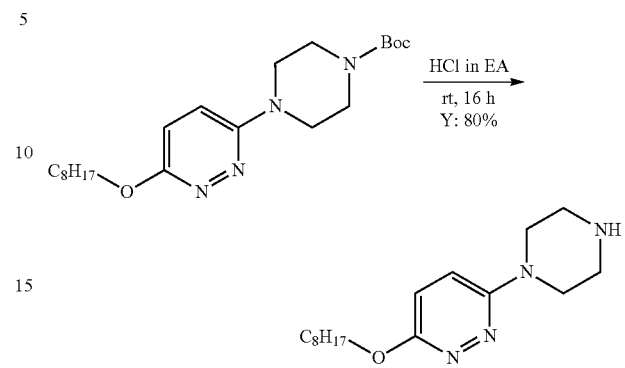

Using the same condition as in intermediate 30, the title compound was obtained as a yellow solid (120 mg, 80% yield), which was used for next step without further purification. LCMS m/z 293.2 [M+H]$^+$.

Example 20

3-(4-(6-(Octyloxy)pyridazin-3-yl)piperazin-1-yl)propanoic acid (Compound 22)

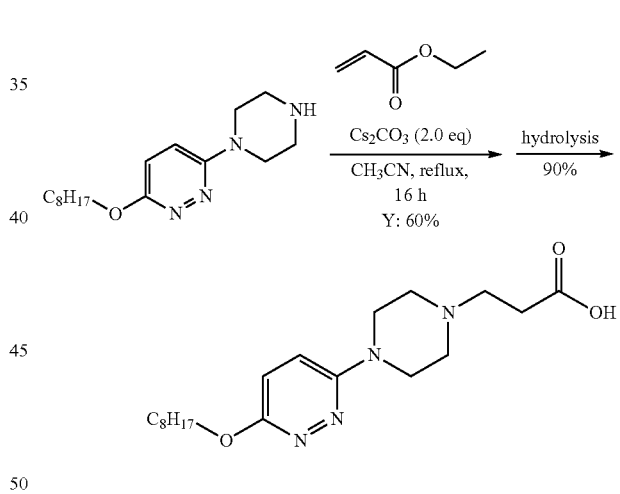

Using the same procedure as for intermediate 5, ethyl 3-(4-(6-(octyloxy)pyridazin-3-yl)piperazin-1-yl)propanoate was obtained as a yellow solid (80 mg, 60% yield). LCMS m/z 393.3 [M+1]$^+$; $^1$H NMR (400 MHz, CDCl$_3$) δ: 7.00 (d, J=9.6 Hz, 1H), 6.82 (d, J=9.6 Hz, 1H), 4.38 (t, J=6.8 Hz, 2H), 4.15 (q, J=7.2 Hz, 2H), 3.52 (bs, 4H), 2.76 (t, J=7.2 Hz, 2H), 2.61 (bs, 4H), 2.54 (t, J=7.2 Hz, 2H), 1.81-1.74 (m, 2H), 1.46-1.39 (m, 2H), 1.31-1.25 (m, 11H), 0.88 (t, J=6.4 Hz, 3H).

Using standard hydrolysis condition, the title compound was obtained as a yellow oil (65 mg, 90% yield). LCMS m/z 365.3 [M+1]$^+$; $^1$H NMR (400 MHz, CD$_3$OD) δ: 7.50 (d, J=10.0 Hz, 1H), 7.13 (d, J=10.0 Hz, 1H), 4.23 (t, J=6.0 Hz, 2H), 3.77 (bs, 4H), 3.42-3.38 (m, 6H), 2.80 (t, J=7.2 Hz, 2H), 1.74-1.67 (m, 2H), 1.42-1.21 (m, 10H), 0.80 (t, J=7.2 Hz, 3H).

Intermediate 36: 2-Chloro-5-(octyloxy)pyrimidine

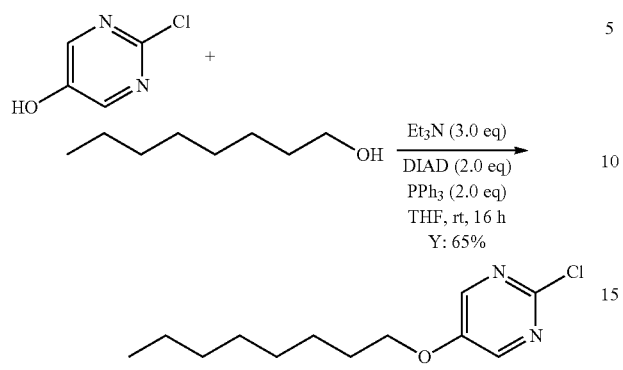

To a mixture of 2-chloropyrimidin-5-ol (700 mg, 5.4 mmol, 1.0 eq), octan-1-ol (1.05 g, 8.1 mmol, 1.5 eq), PPh$_3$ (2.8 g, 10.8 mmol, 2.0 eq) and triethylamine (1.63 g, 16.2 mol, 3.0 eq) in THF (14 mL) was added dropwise DIAD (2.18 g, 10.8 mmol, 2.0 eq) at 0° C. The mixture was allowed to warm up to rt and stirred for 16 h. The solvent was then removed under reduced pressure and the residue was purified by column chromatography on silica gel (PE/EA=10/1) to give the title compound as a yellow oil (847 mg, 65% yield). LCMS m/z 243.1 [M+H]$^+$; 1H NMR (CDCl3, 400 MHz) δ: 8.28 (s, 2H), 4.05 (t, J=6.8 Hz, 2H), 1.85-1.78 (m, 2H), 1.42-1.26 (m, 10H), 0.90-0.86 (m, 3H).

Intermediate 37: 5-(Octyloxy)-2-(piperazin-1-yl)pyrimidine

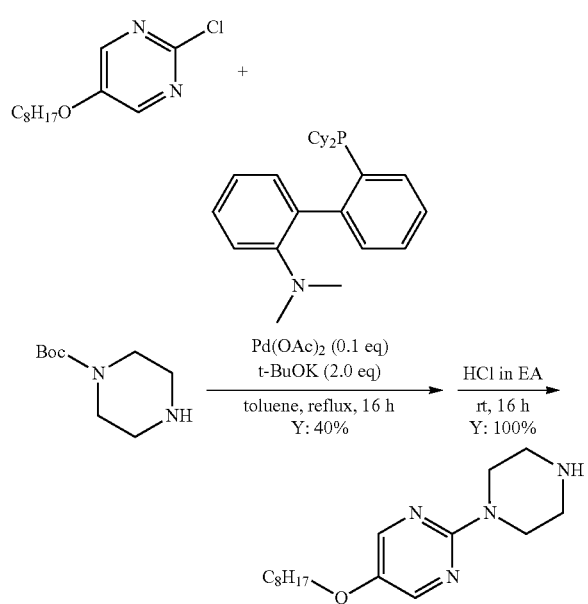

Using the same procedure as for intermediate 29, tert-butyl 4-(5-(octyloxy)pyrimidin-2-yl)piperazine-1-carboxylate was obtained as a yellow oil (290 mg, 40% yield). LCMS m/z 393.4 [M+H]$^+$; $^1$H NMR (400 MHz, CDCl$_3$) δ: 8.09 (s, 2H), 3.91 (t, J=6.4 Hz, 2H), 3.71-3.69 (m, 4H), 3.51-3.48 (m, 4H), 1.78-1.71 (m, 2H), 1.49 (s, 9H), 1.49-1.40 (m, 2H), 1.31 (bs, 8H), 0.89 (t, J=6.8 Hz, 3H).

Using the same procedure as for intermediate 30, the title compound was obtained as a yellow solid (230 mg, 100% yield). LCMS m/z 293.3 [M+H]$^+$.

Example 21

3-(4-(5-(Octyloxy)pyrimidin-2-yl)piperazin-1-yl)propanoic acid (Compound 23)

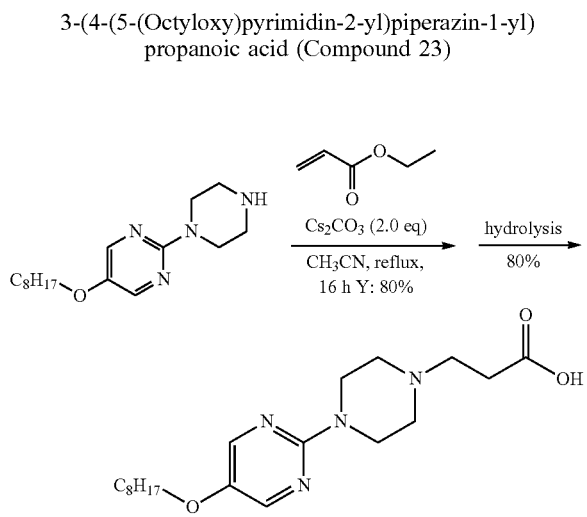

Using the same procedure as for intermediate 5, ethyl 3-(4-(5-(octyloxy)pyrimidin-2-yl)piperazin-1-yl)propanoate was obtained as a yellow solid (240 mg, 80% yield). LCMS m/z 393.4 [M+1]$^+$.

Using standard hydrolysis condition, the title compound was obtained as a gray solid (160 mg, 80% yield). LCMS m/z 365.3 [M+1]$^+$; $^1$H NMR (400 MHz, CD$_3$OD) δ: 8.09 (s, 2H), 3.91-3.88 (m, 2H), 3.39-3.30 (m, 8H), 2.81-2.78 (m, 2H), 1.65 (bs, 2H), 1.38-1.22 (m, 12H), 0.81 (bs, 3H).

Intermediate 38: 2-Bromo-5-(octyloxy)pyridine

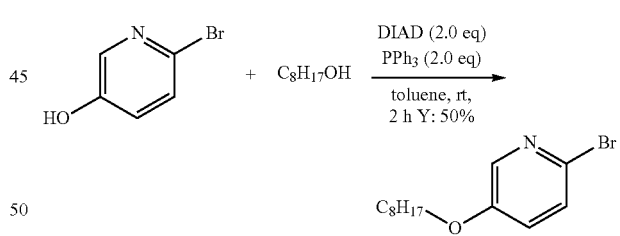

Using the same procedure as for intermediate 33, the title compound was obtained as a yellow oil (730 mg, 50% yield). LCMS: m/z 286.1 [M+H]$^+$.

Intermediate 39: 1-(5-(Octyloxy)pyridin-2-yl)piperazine

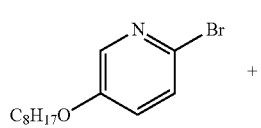

87

-continued

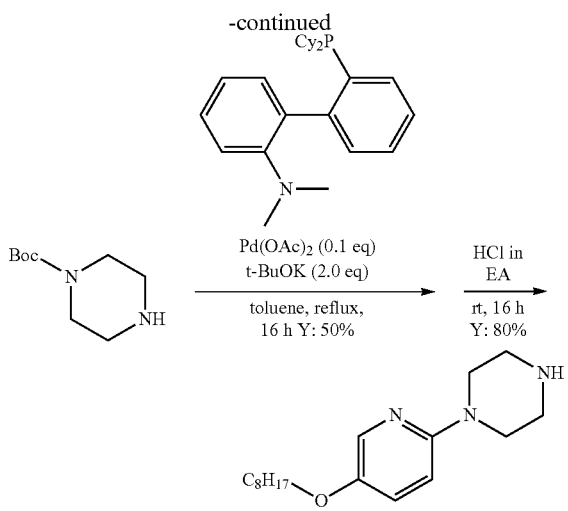

Using the same procedure as for intermediate 29, tert-butyl 4-(5-(octyloxy)pyridin-2-yl)piperazine-1-carboxylate was obtained as a yellow oil (500 mg, 50% yield). LCMS m/z 392.4 [M+H]$^+$; $^1$H NMR (400 MHz, CDCl$_3$) δ: 7.93 (d, J=2.8 Hz, 1H), 7.16 (d, J=9.2 Hz, 1H), 6.64 (d, J=9.2 Hz, 1H), 3.92 (t, J=6.4 Hz, 2H), 3.56-3.54 (m, 4H), 3.40-3.37 (m, 4H), 1.78-1.71 (m, 2H), 1.48 (s, 9H), 1.45-1.40 (m, 2H), 1.37-1.28 (m, 8H), 0.88 (t, J=6.8 Hz, 3H).

Using the same procedure as for intermediate 30 the title compound was obtained as a yellow solid, (200 mg, 80% yield). LCMS m/z 292.3 [M+H]$^+$.

Example 22

3-(4-(5-(Octyloxy)pyridin-2-yl)piperazin-1-yl)propanoic acid (Compound 24)

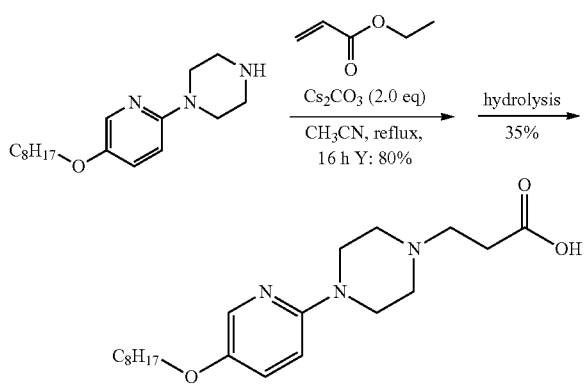

Using the same procedure as for intermediate 5, ethyl 3-(4-(5-(octyloxy)pyridin-2-yl)piperazin-1-yl)propanoate was obtained as a yellow solid (240 mg, 80% yield). LCMS m/z 392.4 [M+1]$^+$.

Using standard hydrolysis condition, the title compound was obtained as a yellow oil (80 mg, 35% yield). LCMS m/z 364.3 [M+1]$^+$; $^1$H NMR (400 MHz, CD$_3$OD) δ: 7.87 (d, J=3.2 Hz, 1H), 7.43 (dd, J=3.2, 9.2 Hz, 1H), 7.01 (d, J=9.2 Hz, 1H), 3.98 (t, J=6.4 Hz, 2H), 3.75-3.47 (m, 10H), 2.90 (t, J=6.8 Hz, 2H), 180-1.73 (m, 2H), 1.50-1.32 (m, 10H), 0.91 (t, J=6.8 Hz, 3H).

88

Intermediate 40: tert-Butyl 3-(4-((trans-4-(tert-butyl)cyclohexyl)oxy)phenyl)-2,5-dihydro-1H-pyrrole-1-carboxylate

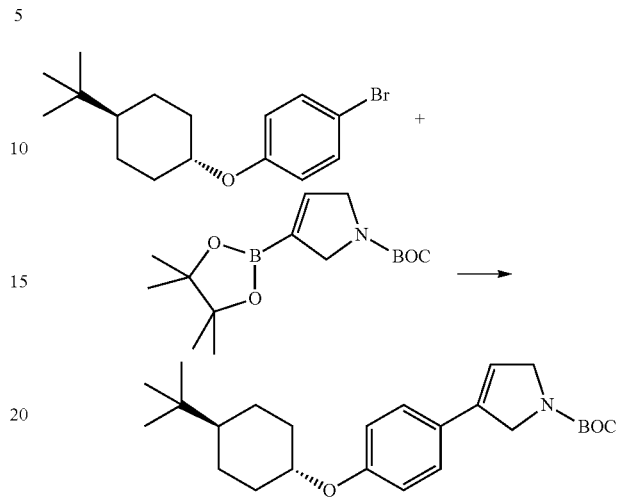

To a microwave vial loaded with 3-(4,4,5,5-tetramethyl-1,3,2-dioxaborolan-2-yl)-2,5-dihydro-pyrrole-1-carboxylic acid tert-butyl ester (177 mg, 0.600 mmol), 1-bromo-4-(4-tert-butyl-cyclohexyloxy)-benzene (156 mg, 0.500 mmol) and tetrakis(triphenylphosphine)palladium(0) (25 mg, 0.022 mmol) was added 1,2-dimethoxyethane (1.5 mL, 14 mmol), followed by ethanol (1.0 mL, 17 mmol) and saturated aqueous NaHCO$_3$ solution (0.5 mL). The reaction mixture was heated with microwave irritation at 120° C. for 20 min. It was then portioned between EtOAc and water. The organic phase was washed with brine, dried over MgSO$_4$, filtered and concentrated. The residue was purified by flash chromatography on silica gel column to get the title compound as a colorless oil (129 mg, 65% yield). $^1$H NMR (300 MHz, METHANOL-d$_4$) δ 7.24 (d, J=8.69 Hz, 2H), 6.84 (d, J=8.69 Hz, 2H), 4.06-4.22 (m, 1H), 3.74-3.93 (m, 2H), 2.95 (q, J=9.06 Hz, 2H), 2.17 (d, J=11.71 Hz, 2H), 1.87 (d, J=10.58 Hz, 2H), 1.51 (s, 9H), 1.01-1.43 (m, 5H), 0.89 (s, 9H); LCMS m/z 400.3 [M+H]$^+$.

Intermediate 41: 3-(4-((trans-4-(tert-Butyl)cyclohexyl)oxy)phenyl)pyrrolidine

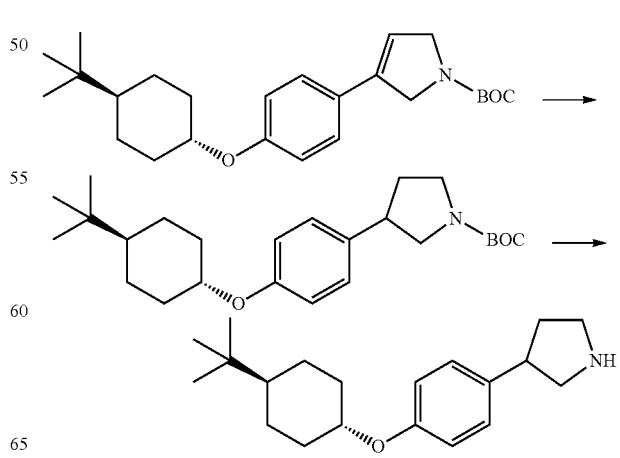

To a solution of tert-butyl 3-(4-((trans-4-(tert-Butyl)cyclohexyl)oxy)phenyl)-2,5-dihydro-1H-pyrrole-1-carboxylate (40 mg, 0.10 mmol) in methanol (4 mL) and EtOAc (2 mL) was added 10% Pd/C (10 mg, 0.09 mmol). The mixture was stirred at rt under H$_2$ atmosphere overnight. It was filtered through celite and concentrated to get an oil, which was treated with 10% TFA in CH$_2$Cl$_2$ (2 mL) at room temperature for 1 h. The reaction mixture was concentrated to give the TFA salt of the desired product (41 mg, yield 98%). $^1$H NMR (400 MHz, METHANOL-d$_4$) δ 7.20 (d, J=8.78 Hz, 2H), 6.89 (d, J=8.78 Hz, 2H), 4.00-4.25 (m, 1H), 3.60-3.72 (m, 1H), 3.35-3.58 (m, 3H), 3.12 (t, J=10.92 Hz, 1H), 2.31-2.49 (m, 1H), 1.96-2.24 (m, 3H), 1.80-1.92 (m, 2H), 1.02-1.45 (m, 5H), 0.89 (s, 9H); LCMS m/z 302.2 [M+H]$^+$.

Example 23

3-(3-(4-((trans-4-(tert-Butyl)cyclohexyl)oxy)phenyl)pyrrolidin-1-yl)propanoic acid (Compound 15)

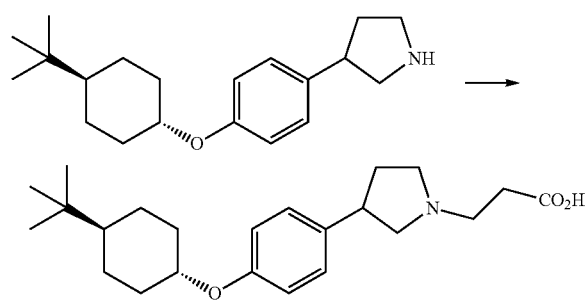

To a suspension of 3-(4-((trans-4-(tert-butyl)cyclohexyl)oxy)phenyl)pyrrolidine TFA salt (18 mg, 0.042 mmol) in acetonitrile (0.5 mL) was added N,N-diisopropylethyl amine (22 μL, 0.13 mmol) and stirred at rt for 2 minutes. 3-Bromopropanoic acid methyl ester (7.0 uL, 0.063 mmol) was then added. The suspension turned to a clear solution after heating with an oil bath (60° C.). The reaction solution was heated at 60° C. for 1 h. It was partitioned between EtOAc and saturated NaHCO$_3$ solution. The aqueous layer was extracted with EtOAc. The combined organic phases were dried over MgSO$_4$, filtered and concentrated. The residue was purified by flash chromatography on silica gel column to get the desired methyl ester as a colorless oil (11 mg, yield 67%). LCMS m/z 388.2 [M+H]$^+$.

To a solution of above methyl ester (8.4 mg, 0.022 mmol) in MeOH (0.3 mL) and THF (0.3 mL) was added 3 N NaOH solution (8.7 uL, 0.026 mmol). The reaction mixture was heated with microwave irritation at 80° C. for 30 min. The mixture was then concentrated and lyophilized to get the sodium salt of the desired acid as a white powder (8.9 mg, yield 100%). $^1$H NMR (300 MHz, METHANOL-d$_4$) δ 7.16 (d, J=8.69 Hz, 2H), 6.82 (d, J=8.69 Hz, 2H), 4.01-4.20 (m, 1H), 3.12-3.36 (m, 2H), 2.71-3.08 (m, 4H), 2.54 (t, J=9.25 Hz, 1H), 2.44 (t, J=7.93 Hz, 2H), 2.08-2.35 (m, 3H), 1.76-1.97 (m, 3H), 0.99-1.44 (m, 5H), 0.89 (s, 9H); LCMS m/z 374.2 [M+H]$^+$ Example 24

4-(3-(4-((trans-4-(tert-Butyl)cyclohexyl)oxy)phenyl)pyrrolidin-1-yl)butanoic acid (Compound 17)

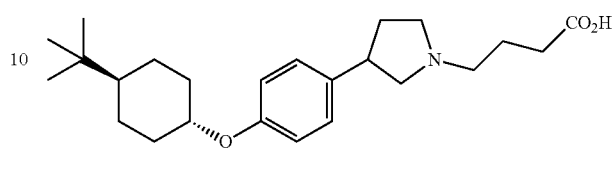

The titled compound was synthesized according to the procedure described in example 23 (9 mg, yield 50%). $^1$H NMR (400 MHz, METHANOL-d$_4$) δ 7.15 (d, J=8.53 Hz, 2H), 6.82 (d, J=8.53 Hz, 2H), 4.02-4.21 (m, 1H), 3.25-3.35 (m, 1H), 3.12 (t, J=8.66 Hz, 1H), 2.86-3.01 (m, 1H), 2.37-2.75 (m, 4H), 2.10-2.35 (m, 5H), 1.71-1.94 (m, 5H), 1.02-1.44 (m, 5H), 0.89 (s, 9H); LCMS m/z 388.3 [M+H]$^+$ Intermediate 42: Ethyl 4-(3-(4-hydroxyphenyl)piperidin-1-yl)cyclohexanecarboxylate

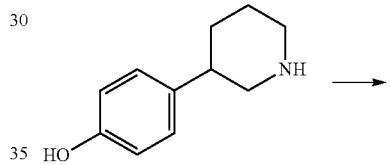

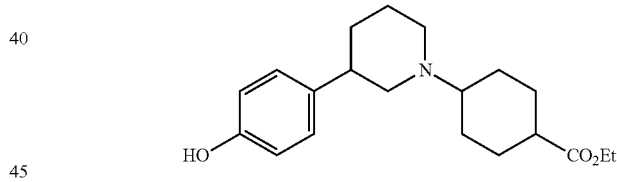

To a mixture of 4-piperidin-3-yl-phenol (89 mg, 0.50 mmol) and 4-oxo-cyclohexanecarboxylic acid ethyl ester (170 mg, 1.00 mmol) in 1,2-dichloroethane (2.5 mL) was added sodium triacetoxyborohydride (212 mg, 1.00 mmol), followed by acetic acid (28 μL, 0.49 mmol). The reaction mixture was stirred at rt for 1 h. It turned to a clear solution after EtOH (2 mL) was added. The reaction solution was stirred at rt overnight, and adjust pH 7 by adding saturated NaHCO$_3$ solution (~2 mL) and water. The mixture was extracted with EtOAc (×2). The combined organic phases were washed with brine, dried over MgSO$_4$, filtered and concentrated in vacuo to get the crude product as a colorless oil (207 mg, 120% yield). It was dissolved in THF (5 mL) to make a 0.1M stock solution for next step. LCMS m/z 332.2 [M+H]$^+$.

Example 25

4-(3-(4-((trans-4-(tert-Butyl)cyclohexyl)oxy)phenyl)piperidin-1-yl)cyclohexanecarboxylic acid (Compound 20)

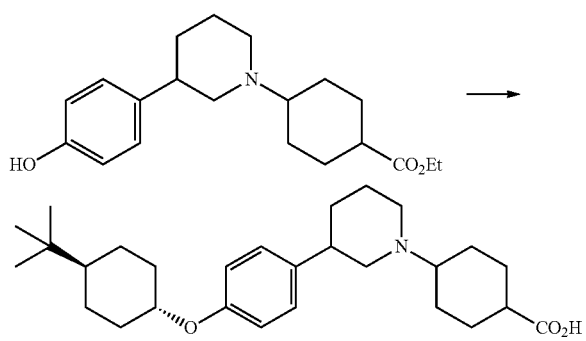

To a mixture of ethyl 4-(3-(4-hydroxyphenyl)piperidin-1-yl)cyclohexanecarboxylate stock solution from previous step (1 mL, 0.10 mmol), 4-tert-butyl-cyclohexanol (23 mg, 0.15 mmol), and triphenylphosphine (39 mg, 0.15 mmol) was added diisopropyl azodicarboxylate (31 uL, 0.15 mmol). The reaction mixture was stirred at rt for 3 h, and another portion of reagents were added and stirred overnight. The reaction mixture was purified by flash chromatography on silica gel column to provide desired ester. LCMS m/z 470.3 [M+H]$^+$ To the above ester in MeOH (0.5 mL) and THF (0.5 mL) was added 3 M NaOH (0.1 mL). The mixture was heated at 50° C. for 1 h, and then leave it stirred at rt overnight. It was neutralized with 2N HCl (150 μL) and purified by HPLC (TFA method) to get TFA salt of the desired product as a white powder after lyophilization (7 mg, 13% yield). $^1$H NMR (300 MHz, METHANOL-d$_4$) δ 7.19 (dd, J=2.83, 8.88 Hz, 2H), 6.88 (d, J=8.69 Hz, 2H), 4.04-4.24 (m, 1H), 2.88-3.74 (m, 7H), 1.44-2.40 (m, 16H), 0.99-1.42 (m, 5H), 0.89 (s, 9H); LCMS m/z 442.3 [M+H]$^+$

Example 26

4-(3-(4-(Octyloxy)phenyl)piperidin-1-yl)cyclohexanecarboxylic acid (Compound 21)

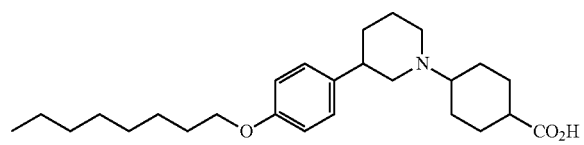 [SMILES: CCCCCCCCOc1ccc(C2CCCN(C3CCC(C(=O)O)CC3)C2)cc1]

The titled compound was synthesized according to the procedure described in Example 25 (4 mg, yield 7%). $^1$H NMR (300 MHz, METHANOL-d$_4$) δ 7.20 (dd, J=2.64, 8.69 Hz, 2H), 6.89 (d, J=8.69 Hz, 2H), 3.95 (t, J=6.42 Hz, 2H), 2.62-3.63 (m, 7H), 1.20-2.41 (m, 24H), 0.83-0.97 (m, 3H); LCMS m/z 416.3 [M+H]$^+$.

Intermediate 43: 1-Bromo-4-((trans-4-ethylcyclohexyl)oxy)benzene

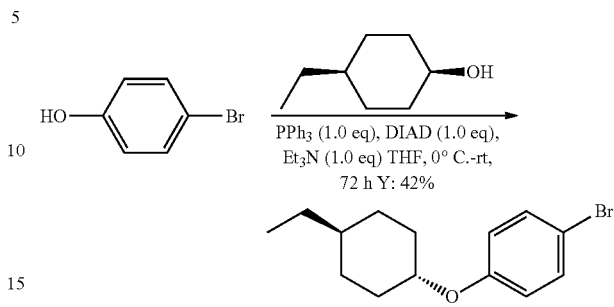

To a mixture of 4-bromophenol (0.9 g, 5.23 mmol, 1.0 eq), (cis)-4-ethylcyclohexanol (0.8 g, 6.28 mmol, 1.2 eq), PPh$_3$ (1.37 g, 5.23 mmol, 1.0 eq) and Et$_3$N (0.53 g, 5.23 mmol, 1.0 eq) in dry THF (40 mL) was quickly added DIAD (1.06 g, 5.23 mmol, 1.0 eq) in one portion at 0° C. under N$_2$. Then the reaction mixture was stirred at room temperature for 72 h. The solvent was removed under vacuum and the residue was purified by silica gel column (PE) to give the title compound as a yellow oil (0.62 g, 42% yield). $^1$H NMR (400 MHz, CDCl$_3$) δ: 7.34 (dd, J=7.2, 2.4 Hz, 2H), 6.77 (dd, J=7.2, 2.4 Hz, 2H), 4.10-4.05 (m, 1H), 2.13-2.09 (m, 2H), 1.84 (t, J=6.4 Hz, 2H), 1.41-1.38 (m, 2H), 1.26-1.19 (m, 3H), 1.04-0.97 (m, 2H), 0.89 (t, J=7.2 Hz, 3H).

Intermediate 44: tert-Butyl 4-(4-((trans-4-ethylcyclohexyl)oxy)phenyl)-5,6-dihydropyridine-1(2H)-carboxylate

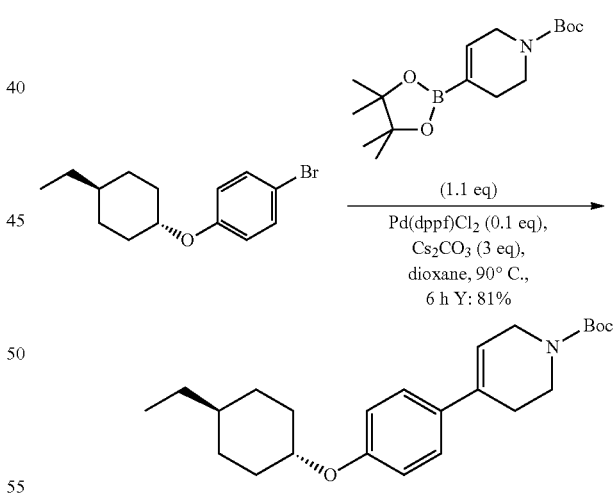

To a solution of 1-bromo-4-((trans-4-ethylcyclohexyl)oxy)benzene (0.6 g, 2.13 mmol, 1.0 eq) in dioxane (30 mL) were added tert-butyl 4-(4,4,5,5-tetramethyl-1,3,2-dioxaborolan-2-yl)-5,6-dihydropyridine-1(2H)-carboxylate (0.69 g, 2.34 mmol, 1.1 eq), Cs$_2$CO$_3$ (2.08 g, 6.39 mmol, 3.0 eq) and PdCl$_2$(dppf) (0.17 g, 0.21 mmol, 0.1 eq) at room temperature under N$_2$. Then the reaction mixture was heated to 90° C. with stirring for 16 h. After cooling to room temperature and filtration, the filtrate was concentrated in vacuo. The residue was purified by silica gel column (PE/EA=15:1) to give the title compound as a white solid (0.66 g, 81% yield). ESI-MS (M+H)+: 385.2. 1H NMR (400 MHz, CDCl3) δ: 7.27 (d, J=8.8 Hz, 2H), 6.84 (d, J=8.8 Hz, 2H), 5.93-5.91 (m, 1H), 4.16-4.08 (m, 1H), 4.04-4.03 (m, 2H), 3.62-3.59 (m, 2H), 2.49-2.47 (m, 2H), 2.15-2.12 (m, 2H), 1.86-1.83 (m, 2H), 1.48 (s, 9H), 1.42-1.38 (m, 2H), 1.26-1.20 (m, 3H), 1.02-0.98 (m, 2H), 0.89 (t, J=7.2 Hz, 3H).

Intermediate 45: 4-(4-((trans-4-Ethylcyclohexyl)oxy)phenyl)-1,2,3,6-tetrahydropyridine

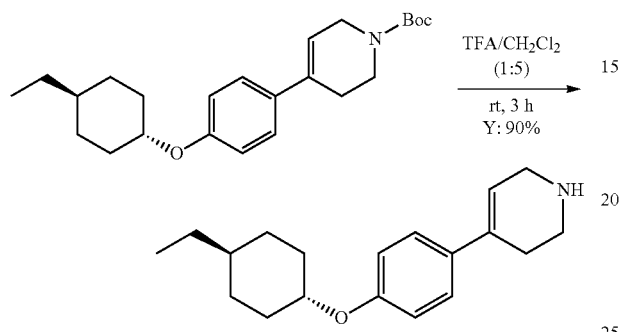

To the solution of tert-butyl 4-(4-(((trans)-4-ethylcyclohexyl)oxy)phenyl)-5,6-dihydropyridine-1(2H)-carboxylate (0.65 g, 1.69 mmol, 1.0 eq) in CH2Cl2 (25.0 mL) was carefully added TFA (5.0 mL) at room temperature. The reaction solution was stirred at room temperature for 16 h. The solvent was removed to give the title compound (0.43 g, 90% yield) as a crude product, which was directly used for the next step without further purification. ESI-MS (M+H)+: 286.2. 1H NMR (400 MHz, CDCl3) δ: 7.27 (m, 2H), 6.84 (m, 2H), 5.95-5.93 (m, 1H), 4.18-4.16 (m, 1H), 3.92-3.45 (m, 2H), 2.81-2.79 (m, 2H), 2.17-2.14 (m, 2H), 1.89-1.86 (m, 2H), 1.47-1.38 (m, 2H), 1.29-1.22 (m, 5H), 1.07-0.96 (m, 2H), 0.91 (t, J=7.2 Hz, 3H).

Intermediate 46: Ethyl 3-(4-(4-((trans-4-ethylcyclohexyl)oxy)phenyl)-5,6-dihydropyridin-1(2H)-yl)propanoate

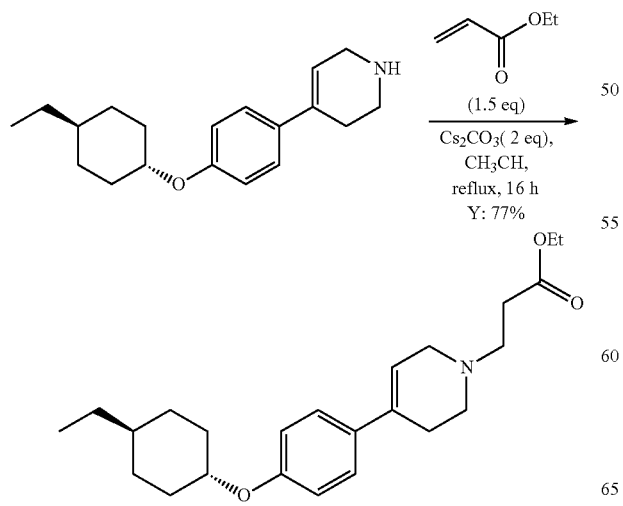

To the solution of 4-(4-((trans-4-ethylcyclohexyl)oxy)phenyl)-1,2,3,6-tetrahydropyridine (250 mg, 0.88 mmol, 1.0 eq) in CH3CN (20 mL) were added ethyl acrylate (132 mg, 1.32 mmol 1.5 eq) and Cs2CO3 (855 mg, 2.63 mmol, 3.0 eq). The mixture was refluxed for 16 h. After cooling to room temperature and filtration, the filtrate was concentrated and purified by silica gel column (PE:EA=2:1) to give the title compound as a yellow solid (260 mg, 77% yield). ESI-MS (M+H)+: 386.2. 1HNMR (400 MHz, CDCl3) δ: 7.29 (d, J=8.8 Hz, 2H), 6.84 (d, J=8.4 Hz, 2H), 5.97-5.95 (m, 1H), 4.17 (q, J=6.8 Hz, 2H), 4.15-4.13 (m, 1H), 3.20-3.18 (m, 2H), 2.86-2.83 (m, 2H), 2.76-2.74 (m, 2H), 2.62-2.55 (m, 4H), 2.16-2.14 (m, 2H), 1.87-1.85 (m, 2H), 1.43-1.39 (m, 2H), 1.29-1.22 (m, 6H), 1.03-0.98 (m, 2H), 0.91 (t, J=7.2 Hz, 3H).

Intermediate 47: Ethyl 3-(4-(4-((trans-4-ethylcyclohexyl)oxy)phenyl)piperidin-1-yl)propanoate

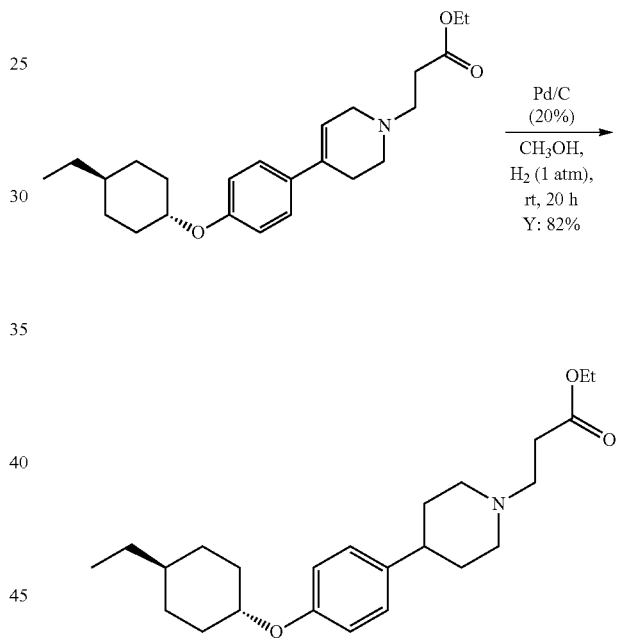

To a solution of ethyl 3-(4-(4-((trans-4-ethylcyclohexyl)oxy)phenyl)-5,6-dihydropyridin-1(2H)-yl)propanoate (120 mg, 0.312 mmol, 1.0 eq) in CH3OH (20 mL) was carefully added Pd/C (24 mg, 20% wt). The reaction solution was stirred at 25° C. under H2 at 1 atm for 20 h. Then the mixture was filtered and concentrated in vacuo to give the title compound as yellow gum (1.8 g, 82% yield). ESI-MS (M+H)+: 387.2. 1HNMR (400 MHz, CDCl3) δ: 7.12 (d, J=8.8 Hz, 2H), 6.82 (d, J=8.4 Hz, 2H), 4.13 (q, J=6.8 Hz, 2H), 4.13-4.11 (m, 1H), 3.44-3.42 (m, 2H), 2.84-2.82 (m, 2H), 2.58-2.55 (m, 2H), 2.43 (t, J=7.2 Hz, 3H), 2.13-2.11 (m, 4H), 1.95-1.82 (m, 4H), 1.41-1.36 (m, 2H), 1.28-1.20 (m, 6H), 1.00-0.97 (m, 2H), 0.88 (t, J=7.2 Hz, 3H).

Example 27

3-(4-(4-((trans-4-Ethylcyclohexyl)oxy)phenyl)-5,6-dihydropyridin-1(2H)-yl)propanoic acid (Compound 45)

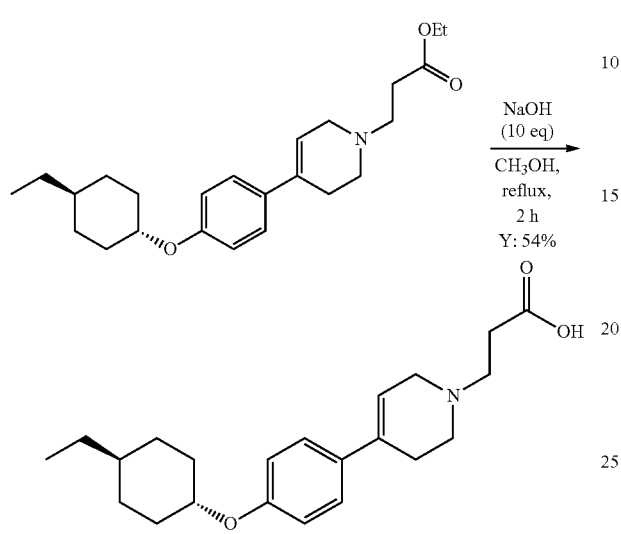

To the solution of ethyl 3-(4-(4-((trans-4-ethylcyclohexyl)oxy)phenyl)piperidin-1-yl)propanoate (90 mg, 0.234 mmol, 1.0 eq) in CH$_3$OH (20 mL) was added NaOH (94 mg, 2.34 mmol, 10.0 eq) in H$_2$O (4 ml). The reaction solution was heated to 80° C. for 2 h with stirring. After concentration, the residue was adjusted to pH=6 with 1N HCl, extracted with EtOAc (50 mL×2), washed with H$_2$O (15 mL) and brine (20 mL), dried over Na$_2$SO$_4$, filtered, and concentrated to give the title compound as a white solid (45 mg, 54% yield). ESI-MS (M+H)$^+$: 358.2. HPLC: 99.42%-100.00%. $^1$HNMR (400 MHz, CDCl$_3$) δ: 7.28 (d, J=8.8 Hz, 2H), 6.86 (d, J=8.8 Hz, 2H), 5.94-5.92 (m, 1H), 4.15-4.13 (m, 1H), 3.47-3.45 (m, 2H), 3.04-2.96 (m, 4H), 2.68-2.61 (m, 4H), 2.15-2.13 (m, 2H), 1.87-1.84 (m, 2H), 1.43-1.23 (m, 5H), 1.02-0.98 (m, 2H), 0.90 (t, J=7.2 Hz, 3H).

Example 28

3-(4-(4-((trans-4-ethylcyclohexyl)oxy)phenyl)piperidin-1-yl)propanoic acid (Compound 30)

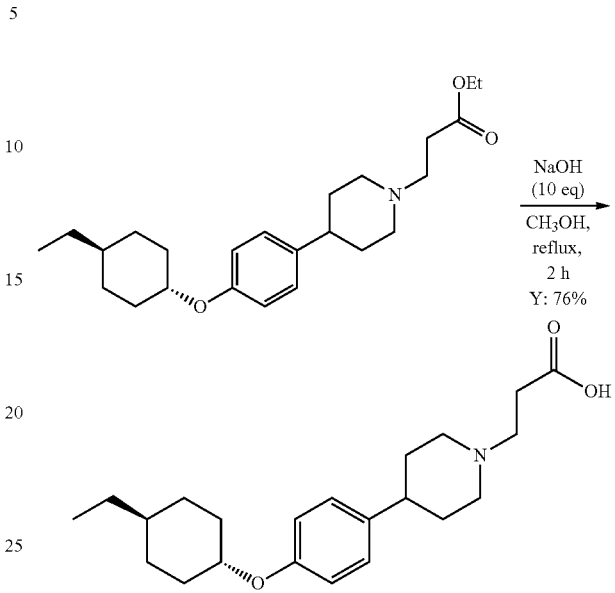

Using the same procedure as for example 27, the title compound was obtained as a white solid (70 mg, 76% yield). ESI-MS (M+H)$^+$: 360.2; $^1$HNMR (400 MHz, CDCl$_3$) δ: 7.09 (d, J=8.8 Hz, 2H), 6.84 (d, J=8.8 Hz, 2H), 4.11-4.09 (m, 1H), 3.32-3.29 (m, 2H), 2.89-2.87 (m, 2H), 2.60-2.57 (m, 3H), 2.47-2.45 (m, 2H), 2.14-2.12 (m, 2H), 1.95-1.83 (m, 6H), 1.42-1.23 (m, 5H), 1.01-0.98 (m, 2H), 0.88 (t, J=7.2 Hz, 3H).

Example 29

4-(4-(4-((trans-4-Ethylcyclohexyl)oxy)phenyl)-5,6-dihydropyridin-1(2H)-yl)butanoic acid (Compound 44)

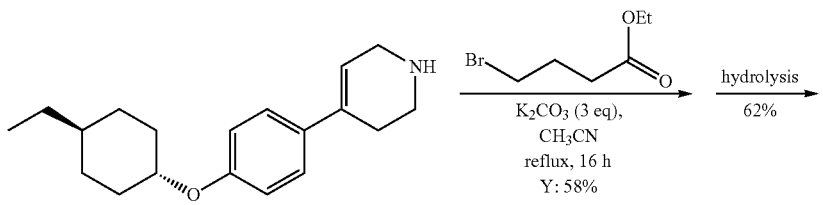

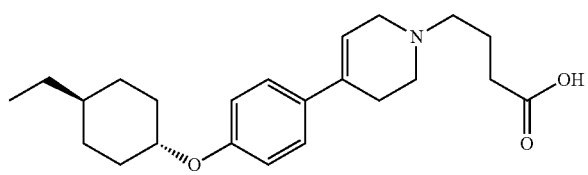

Using the same procedure as for intermediate 6, ethyl 4-(4-(4-((trans-4-ethylcyclohexyl)oxy)phenyl)-5,6-dihydropyridin-1(2H)-yl)butanoate was obtained as a yellow solid (240 mg, 58% yield). ESI-MS (M+H)+: 400.2. ¹HNMR (400 MHz, CDCl₃) δ: 7.28 (d, J=8.8 Hz, 2H), 6.83 (d, J=8.4 Hz, 2H), 5.96-5.94 (m, 1H), 4.14 (q, J=6.8 Hz, 2H), 4.15-4.13 (m, 1H), 3.14-3.13 (m, 2H), 2.70-2.67 (m, 2H), 2.53-2.46 (m, 4H), 2.37 (t, J=7.2 Hz, 2H), 2.15-2.12 (m, 2H), 1.91-1.83 (m, 5H), 1.45-1.27 (m, 2H), 1.26-1.21 (m, 5H), 1.03-0.98 (m, 2H), 0.89 (t, J=7.2 Hz, 3H).

Using standard hydrolysis condition, the title compound was obtained a white solid (52 mg, 62% yield). ESI-MS (M+H)+: 372.2. ¹HNMR (400 MHz, CDCl₃) δ: 7.20 (d, J=7.2 Hz, 2H), 6.78 (d, J=8.8 Hz, 2H), 5.84-5.82 (m, 1H), 4.08-4.06 (m, 1H), 3.44-3.42 (m, 2H), 3.01-2.99 (m, 2H), 2.82-2.80 (m, 2H), 2.65-2.55 (m, 4H), 2.08-2.06 (m, 2H), 1.89-1.86 (m, 2H), 1.80-1.77 (m, 2H), 1.35-1.17 (m, 5H), 0.93-0.91 (m, 2H), 0.83 (t, J=7.2 Hz, 3H).

Example 30

4-(4-(4-((trans-4-Ethylcyclohexyl)oxy)phenyl)piperidin-1-yl)butanoic acid (Compound 29)

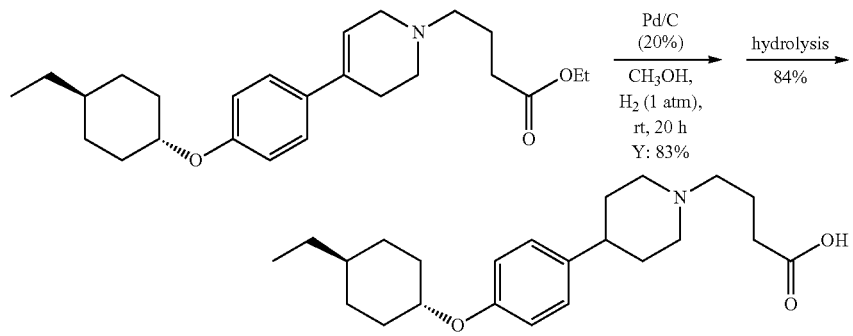

Using the same procedure as for intermediate 47, ethyl 4-(4-(4-((trans-4-ethylcyclohexyl)oxy)phenyl)piperidin-1-yl)butanoate was obtained as a yellow gum (125 mg, 83% yield). ESI-MS (M+H)+: 402.2. ¹HNMR (400 MHz, CDCl₃) δ: 7.06 (d, J=8.8 Hz, 2H), 6.76 (d, J=8.4 Hz, 2H), 4.10-4.03 (m, 3H), 3.38-3.35 (m, 2H), 2.78-2.76 (m, 2H), 2.52-2.50 (m, 2H), 2.37 (t, J=7.2 Hz, 2H), 2.33-2.05 (m, 5H), 1.88-1.75 (m, 4H), 1.34-1.30 (m, 2H), 1.21-1.12 (m, 8H), 0.98-0.91 (m, 2H), 0.82 (t, J=7.2 Hz, 3H).

Using standard hydrolysis condition, the title compound was obtained as a white solid (98 mg, 84% yield). ESI-MS (M+H)+: 374.3. ¹HNMR (400 MHz, CDCl₃) δ: 7.11 (d, J=8.4 Hz, 2H), 6.84 (d, J=8.4 Hz, 2H), 4.12-4.10 (m, 1H), 3.35-3.32 (m, 2H), 2.80-2.78 (m, 2H), 2.77-2.63 (m, 5H), 2.16-1.84 (m, 10H), 1.42-1.28 (m, 5H), 1.02-0.99 (m, 2H), 0.90 (t, J=7.2 Hz, 3H).

Example 31

5-(4-(4-((trans-4-Ethylcyclohexyl)oxy)phenyl)-5,6-dihydropyridin-1(2H)-yl)pentanoic acid (Compound 43)

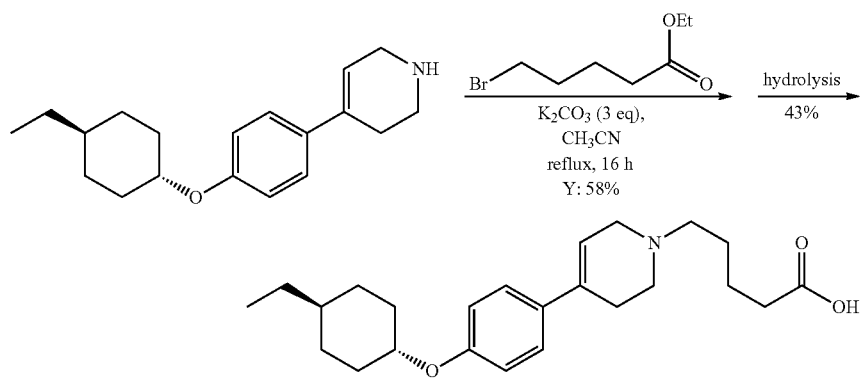

Using the same procedure as for intermediate 6, ethyl 5-(4-(4-((trans-4-ethylcyclohexyl)oxy)phenyl)-5,6-dihydropyridin-1(2H)-yl)pentanoate was obtained as a yellow solid (240 mg, 58% yield). ESI-MS (M+H)$^+$: 414.2. $^1$HNMR (400 MHz, CDCl$_3$) δ: 7.21 (d, J=8.4 Hz, 2H), 6.76 (d, J=8.8 Hz, 2H), 5.89-5.87 (m, 1H), 4.08-4.03 (m, 3H), 3.06-3.05 (m, 2H), 2.62-2.59 (m, 2H), 2.47-2.37 (m, 4H), 2.29-2.26 (m, 2H), 2.08-2.06 (m, 2H), 1.79-1.76 (m, 2H), 1.61-1.53 (m, 4H), 1.37-1.28 (m, 2H), 1.20-1.16 (m, 6H), 0.97-0.86 (m, 2H), 0.82 (t, J=7.2 Hz, 3H).

Using standard hydrolysis condition, the title compound was obtained as a pale yellow solid (32 mg, 43% yield). ESI-MS (M+H)$^+$: 386.3. $^1$HNMR (400 MHz, CDCl$_3$) δ: 7.21 (d, J=8.8 Hz, 2H), 6.77 (d, J=8.8 Hz, 2H), 5.86-5.84 (m, 1H), 4.08-4.06 (m, 1H), 3.39-3.36 (m, 2H), 2.98-2.96 (m, 2H), 2.65-2.59 (m, 3H), 2.20-2.18 (m, 2H), 2.07-2.04 (m, 2H), 1.79-1.76 (m, 2H), 1.56-1.54 (m, 4H), 1.35-1.33 (m, 2H), 1.21-1.14 (m, 4H), 0.96-0.93 (m, 2H), 0.82 (t, J=7.2 Hz, 3H).

Example 32

5-(4-(4-((trans-4-Ethylcyclohexyl)oxy)phenyl)piperidin-1-yl)pentanoic acid (Compound 28)

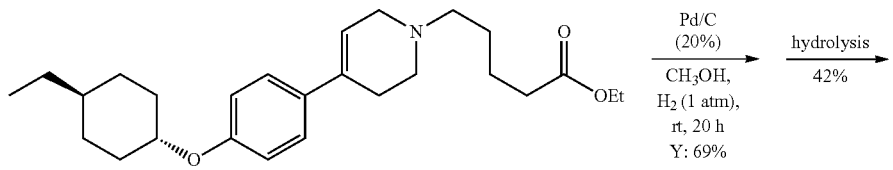

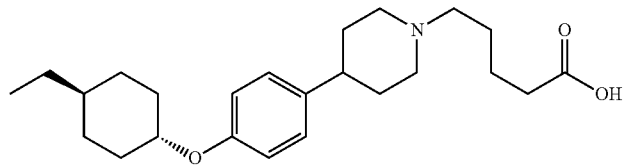

Using the same condition as in intermediate 47, ethyl 5-(4-(4-((trans-4-ethylcyclohexyl)oxy)phenyl)piperidin-1-yl)pentanoate was obtained as a yellow gum (104 mg, 69% yield). ESI-MS (M+H)$^+$: 416.3. $^1$HNMR (400 MHz, CDCl$_3$) δ: 7.13 (d, J=8.8 Hz, 2H), 6.82 (d, J=8.4 Hz, 2H), 4.16-4.11 (m, 3H), 3.44-3.42 (m, 2H), 2.84-2.82 (m, 2H), 2.59-2.55 (m, 2H), 2.43 (m, 3H), 2.26-2.24 (m, 2H), 2.13-2.11 (m, 4H), 1.95-1.82 (m, 4H), 1.39-1.36 (m, 2H), 1.28-1.20 (m, 8H), 1.01-0.97 (m, 2H), 0.88 (t, J=7.2 Hz, 3H).

Using standard hydrolysis condition, the title compound was obtained as a pale yellow solid (35 mg, 42% yield). ESI-MS (M+H)$^+$: 388.3. $^1$HNMR (400 MHz, CDCl$_3$) δ: 7.03 (d, J=8.4 Hz, 2H), 6.75 (d, J=8.8 Hz, 2H), 4.03-4.01 (m, 1H), 3.52-3.50 (m, 2H), 2.78-2.76 (m, 2H), 2.51-2.49 (m, 2H), 2.27-2.25 (m, 2H), 2.08-2.03 (m, 4H), 1.86-1.75 (m, 6H), 1.60-1.58 (m, 2H), 1.33-1.14 (m, 7H), 0.91-0.89 (m, 1H), 0.81 (t, J=7.2 Hz, 3H).

Intermediate 48:
1-Bromo-4-((cis-4-ethylcyclohexyl)oxy)benzene

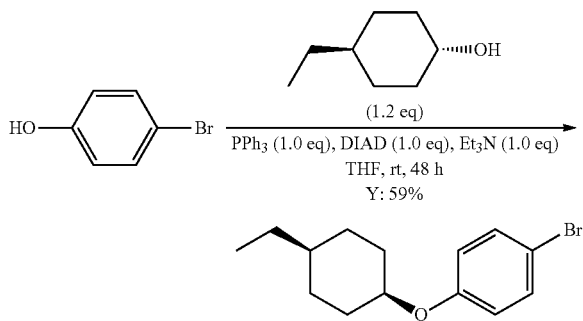

Using the same procedure as for intermediate 43, the title compound was obtained as, as yellow oil (2.5 g, 59% yield). $^1$H NMR (400 MHz, CDCl$_3$) δ: 7.39-7.36 (m, 2H), 6.83-6.78 (m, 2H), 4.49-4.47 (m, 1H), 2.02-1.98 (m, 1H), 1.60-1.53 (m, 3H), 1.41-1.28 (m, 7H), 0.92 (t, J=7.2 Hz, 3H).

Intermediate 49: tert-Butyl 4-(4-((cis-4-ethylcyclohexyl)oxy)phenyl)-5,6-dihydropyridine-1(2H)-carboxylate

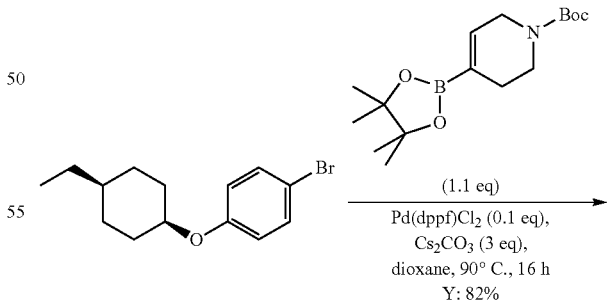

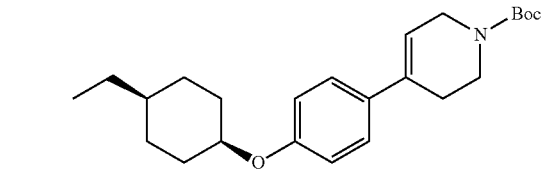

Using the same procedure as for intermediate 44, the title compound was obtained, as yellow gum (2.36 g, 82% yield). ESI-MS (M+H)+: 386.2. 1H NMR (400 MHz, CDCl3) δ: 7.19 (d, J=8.4 Hz, 2H), 6.78 (d, J=8.8 Hz, 2H), 5.85-5.83 (m, 1H), 4.42-4.40 (m, 1H), 3.97-3.95 (m, 2H), 3.54-3.52 (m, 2H), 2.41-2.39 (m, 2H), 1.91-1.88 (m, 2H), 1.48-1.42 (m, 4H), 1.40 (s, 9H), 1.34-1.31 (m, 2H), 1.22-1.18 (m, 3H), 0.81 (t, J=7.2 Hz, 3H).

Intermediate 50: 4-(4-((cis-4-Ethylcyclohexyl)oxy)phenyl)-1,2,3,6-tetrahydropyridine

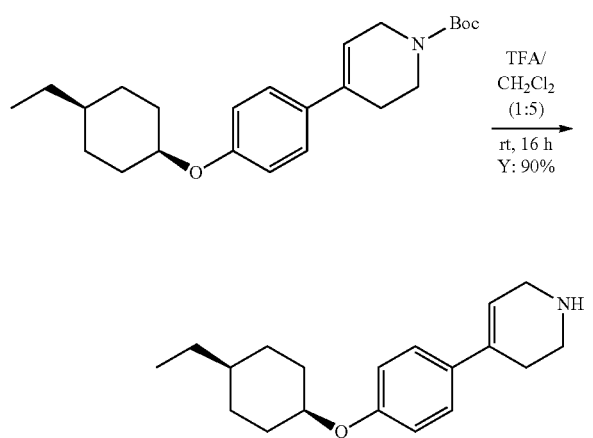

Using the same condition as in intermediate 45, the title compound was obtained as a pale yellow solid (220 mg, 90% yield). ESI-MS (M+H)+: 285.2. 1H NMR (400 MHz, CDCl3) δ: 8.20 (br, 1H), 7.17 (d, J=10.0 Hz, 2H), 6.79 (d, J=8.4 Hz, 2H), 5.82-5.80 (m, 1H), 4.43-4.42 (m, 1H), 3.81-3.79 (m, 2H), 3.41-3.40 (m, 2H), 2.69-2.67 (m, 2H), 1.90-1.86 (m, 2H), 1.49-1.43 (m, 4H), 1.32-1.30 (m, 2H), 1.26-1.15 (m, 3H), 0.79 (t, J=7.2 Hz, 3H).

Example 33

3-(4-(4-((cis-4-Ethylcyclohexyl)oxy)phenyl)-5,6-dihydropyridin-1(2H)-yl)propanoic acid (Compound 39)

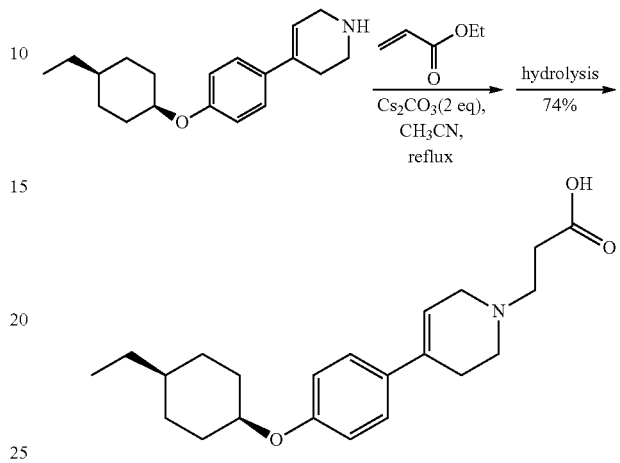

Using the same procedure as for intermediate 5, ethyl 3-(4-(4-((cis-4-ethylcyclohexyl)oxy)phenyl)-5,6-dihydropyridin-1(2H)-yl)propanoate was obtained as pale yellow solid (260 mg, 77% yield). ESI-MS (M+H)+: 386.2. 1H NMR (400 MHz, CD3Cl) δ: 7.21 (d, J=8.8 Hz, 2H), 6.78 (d, J=8.8 Hz, 2H), 5.89-5.86 (m, 1H), 4.43-4.41 (m, 1H), 4.08 (q, J=6.8 Hz, 2H), 3.12-3.10 (m, 2H), 2.78-2.73 (m, 2H), 2.68-2.66 (m, 2H), 2.54-2.41 (m, 4H), 1.42-1.40 (m, 4H), 1.23-1.15 (m, 10H), 0.80 (t, J=7.2 Hz, 3H).

Using standard hydrolysis condition, the title compound was obtained as a pale yellow solid (40 mg, 74% yield). ESI-MS (M+H)+: 358.2. 1HNMR (400 MHz, DMSO-d6) δ: 7.32 (d, J=8.8 Hz, 2H), 6.87 (d, J=8.8 Hz, 2H), 6.02-6.00 (m, 1H), 4.56-4.54 (m, 1H), 3.10-3.09 (m, 2H), 2.68-2.65 (m, 4H), 2.43-2.36 (m, 4H), 1.88-1.85 (m, 2H), 1.52-1.48 (m, 4H), 1.25-1.23 (m, 5H), 0.86 (t, J=7.2 Hz, 3H).

Example 34

3-(4-(4-((cis-4-Ethylcyclohexyl)oxy)phenyl)piperidin-1-yl)propanoic acid (Compound 26)

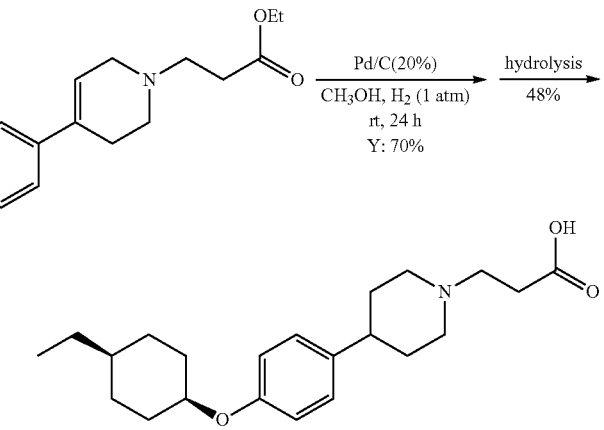

Using the same procedure as for intermediate 47, ethyl 3-(4-(4-((cis-4-ethylcyclohexyl)oxy)phenyl)piperidin-1-yl) propanoate was obtained as yellow gum (91 mg, 70% yield). ESI-MS (M+H)⁺: 386.2. ¹HNMR (400 MHz, CDCl₃) δ: 7.03 (d, J=8.4 Hz, 2H), 6.76 (d, J=8.4 Hz, 2H), 4.39-4.37 (m, 1H), 4.05 (q, J=7.2 Hz, 2H), 3.63-3.62 (m, 2H), 2.95-2.93 (m, 2H), 2.68-2.66 (m, 2H), 2.68-2.47 (m, 2H), 2.05-2.03 (m, 2H), 1.89-1.87 (m, 2H), 1.73-1.70 (m, 3H), 1.49-1.42 (m, 4H), 1.23-1.16 (m, 8H), 0.82 (t, 3H).

Using standard hydrolysis condition, the title compound was obtained as a pale yellow gum (40 mg, 48% yield). ESI-MS (M+H)⁺: 360.3. ¹HNMR (400 MHz, CDCl₃) δ: 7.01 (d, J=8.4 Hz, 2H), 6.76 (d, J=8.4 Hz, 2H), 4.38-4.36 (m, 1H), 3.34-3.31 (m, 2H), 2.96-2.94 (m, 2H), 2.52-2.50 (m, 4H), 1.87-1.85 (m, 6H), 1.47-1.17 (m, 10H), 0.81 (t, J=7.2 Hz, 3H).

Example 35

4-(4-(4-((cis-4-Ethylcyclohexyl)oxy)phenyl)-5,6-dihydropyridin-1(2H)-yl)butanoic acid (Compound 41)

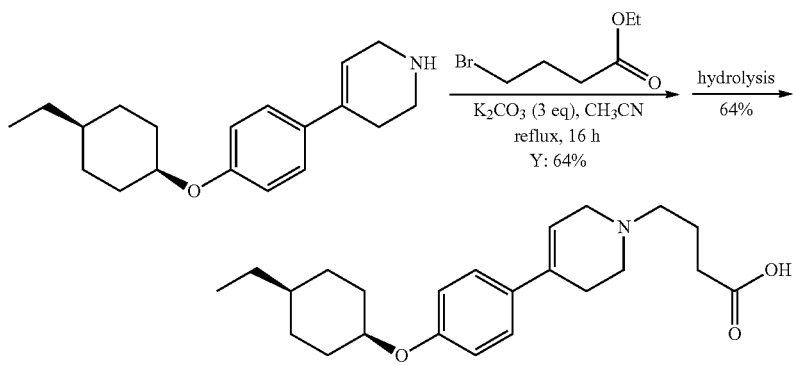

Using the same condition as in intermediate 6, ethyl 4-(4-(4-((cis-4-ethylcyclohexyl)oxy)phenyl)-5,6-dihydropyridin-1(2H)-yl)butanoate was obtained as a yellow solid (180 mg, 64% yield). ESI-MS (M+H)⁺: 400.2. ¹HNMR (400 MHz, CDCl₃) δ: 7.29 (d, J=8.8 Hz, 2H), 6.84 (d, J=8.8 Hz, 2H), 5.95-5.93 (m, 1H), 4.49-4.47 (m, 1H), 4.13-4.10 (m, 2H), 3.16-3.14 (m, 2H), 2.70-2.68 (m, 2H), 2.54-2.47 (m, 4H), 2.39-2.36 (m, 2H), 1.99-1.91 (m, 4H), 1.54-1.50 (m, 4H), 1.29-1.24 (m, 8H), 0.88 (t, J=7.2 Hz, 3H).

Using standard hydrolysis condition, the title compound was obtained as a white solid (40 mg, 61% yield). ESI-MS (M+H)⁺: 372.2. ¹HNMR (400 MHz, MeOD) δ: 7.28 (d, J=8.8 Hz, 2H), 6.80 (d, J=8.8 Hz, 2H), 5.92-5.90 (m, 1H), 4.48-4.46 (m, 1H), 3.73-3.71 (m, 2H), 3.34-3.33 (m, 2H), 3.10-3.08 (m, 2H), 2.74-2.73 (m, 2H), 2.39-2.36 (m, 2H), 1.89-1.85 (m, 4H), 1.49-1.45 (m, 4H), 1.29-1.18 (m, 5H), 0.80 (t, J=7.2 Hz, 3H).

Example 36

4-(4-(4-((cis-4-Ethylcyclohexyl)oxy)phenyl)piperidin-1-yl)butanoic acid (Compound 36)

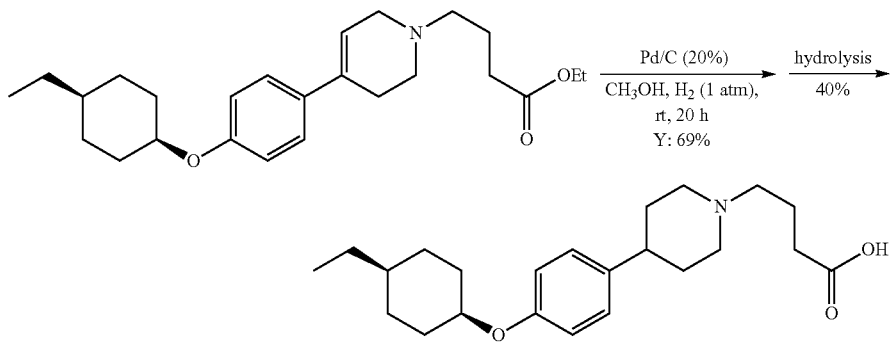

Using the same procedure as for intermediate 47, ethyl 4-(4-(4-((cis-4-ethylcyclohexyl)oxy)phenyl)piperidin-1-yl)butanoate was obtained, as a pale yellow gum (104 mg, 69% yield). ESI-MS (M+H)+: 402.2. ¹HNMR (400 MHz, CDCl₃) δ: 7.10 (d, J=8.4 Hz, 2H), 6.83 (d, J=8.4 Hz, 2H), 4.45-4.43 (m, 1H), 4.14-4.12 (m, 2H), 3.68-3.67 (m, 1H), 3.06-3.03 (m, 2H), 2.43-2.32 (m, 4H), 2.08-1.76 (m, 10H), 1.52-1.49 (m, 4H), 1.29-1.23 (m, 8H), 0.88 (t, J=7.2 Hz, 3H).

Using standard hydrolysis condition, the title compound was obtained as a yellow solid (33 mg, 40% yield). ESI-MS (M+H)+: 374.2. ¹HNMR (400 MHz, CDCl₃) δ: 7.03 (d, J=8.4 Hz, 2H), 6.76 (d, J=8.4 Hz, 2H), 4.40-4.38 (m, 1H), 3.28-3.26 (m, 2H), 2.74-2.72 (m, 2H), 2.54-2.44 (m, 4H), 1.95-1.82 (m, 8H), 1.46-1.43 (m, 4H), 1.32-1.18 (m, 6H), 0.82 (t, J=7.2 Hz, 3H).

Example 37

5-(4-(4-((cis-4-Ethylcyclohexyl)oxy)phenyl)-5,6-dihydropyridin-1(2H)-yl)pentanoic acid (Compound 42)

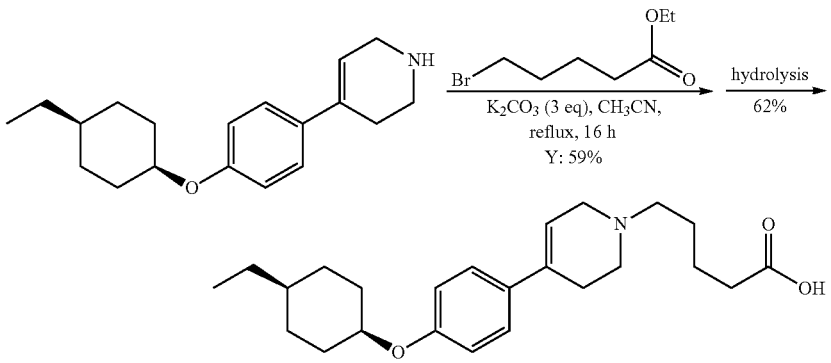

Using the same procedure as for intermediate 6, ethyl 5-(4-(4-((cis-4-ethylcyclohexyl)oxy)phenyl)-5,6-dihydropyridin-1(2H)-yl)pentanoate was obtained, as a pale yellow solid (170 mg, 59% yield). ESI-MS (M+H)+: 414.2. ¹HNMR (400 MHz, CDCl₃) δ: 7.22 (d, J=8.8 Hz, 2H), 6.77 (d, J=8.8 Hz, 2H), 5.89-5.87 (m, 1H), 4.41-4.40 (m, 1H), 4.05 (q, J=6.8 Hz, 2H), 3.07-3.06 (m, 2H), 2.62-2.60 (m, 2H), 2.47-2.37 (m, 4H), 2.28-2.26 (m, 2H), 1.92-1.90 (m, 2H), 1.63-1.44 (m, 9H), 1.19-1.18 (m, 7H), 0.82 (t, J=7.2 Hz, 3H).

Using standard hydrolysis condition, the title compound was obtained as a pale yellow gum (40 mg, 62% yield). ESI-MS (M+H)+: 386.3. ¹HNMR (400 MHz, CDCl₃) δ: 7.22 (d, J=8.8 Hz, 2H), 6.79 (d, J=8.8 Hz, 2H), 5.86-5.84 (m, 1H), 4.44-4.42 (m, 1H), 3.47-3.45 (m, 2H), 3.06-3.04 (m, 2H), 2.72-2.64 (m, 4H), 2.23-2.20 (m, 2H), 1.92-1.88 (m, 2H), 1.71-1.69 (m, 2H), 1.58-1.56 (m, 2H), 1.46-1.43 (m, 3H), 1.31-1.18 (m, 6H), 0.82 (t, J=7.2 Hz, 3H).

Example 38

5-(4-(4-((cis-4-Ethylcyclohexyl)oxy)phenyl)piperidin-1-yl)pentanoic acid (Compound 31)

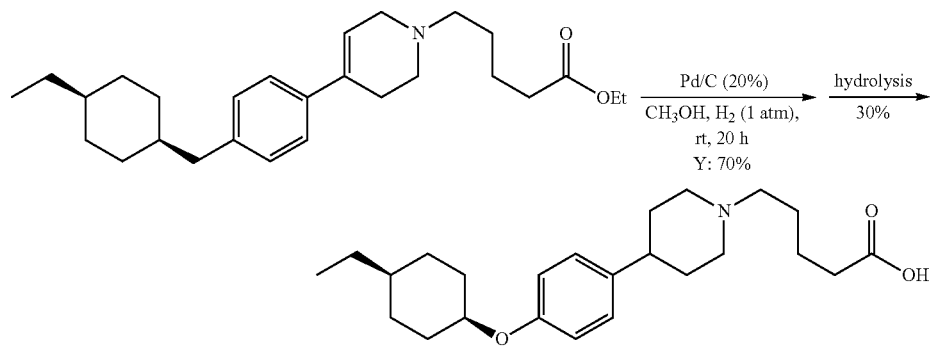

Using the same procedure as for intermediate 47, ethyl 5-(4-(4-((cis-4-ethylcyclohexyl)oxy)phenyl)piperidin-1-yl)pentanoate was obtained as pale yellow gum (64 mg, 70% yield). ESI-MS (M+H)+: 416.3. ¹HNMR (400 MHz, CDCl₃) δ: 7.10 (d, J=8.4 Hz, 2H), 6.82 (d, J=8.4 Hz, 2H), 4.45-4.43 (m, 1H), 4.15-4.12 (m, 2H), 3.06-3.03 (m, 2H), 2.45-2.32 (m, 6H), 2.06-1.76 (m, 11H), 1.52-1.49 (m, 4H), 1.29-1.23 (m, 8H), 0.88 (t, J=7.2 Hz, 3H).

Using standard hydrolysis condition, the title compound was obtained as a pale yellow gum (11 mg, 30% yield). ESI-MS (M+H)+: 388.3. ¹HNMR (400 MHz, CDCl₃) δ: 7.11 (d, J=8.4 Hz, 2H), 6.83 (d, J=8.8 Hz, 2H), 4.45-4.43 (m, 1H), 3.59-3.56 (m, 2H), 2.87-2.85 (m, 2H), 2.63-2.61 (m, 2H), 2.37-2.35 (m, 2H), 2.24-2.21 (m, 2H), 1.97-1.94 (m, 4H), 1.86-1.84 (m, 2H), 1.70-1.67 (m, 2H), 1.55-1.49 (m, 4H), 1.39-1.25 (m, 6H), 0.87 (t, J=7.2 Hz, 3H).

Intermediate 51: 8-(4-Bromophenoxyl)spiro[4.5]decane

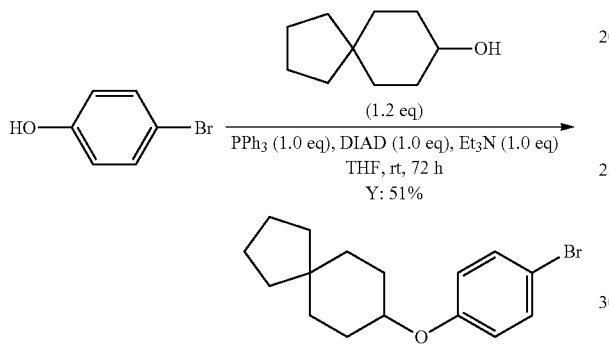

Using the same procedure as for intermediate 43, the title compound was obtained, as yellow oil (2.3 g, 51% yield). ¹H NMR (400 MHz, CDCl₃) δ: 7.34 (dd, J=8.8 Hz, 2H), 6.78 (dd, J=8.8 Hz, 2H), 4.20-4.18 (m, 1H), 1.88-1.85 (m, 2H), 1.6-1.55 (m, 8H), 1.47-1.30 (m, 6H).

Intermediate 52: tert-butyl 4-(4-(Spiro[4.5]decan-8-yloxy)phenyl)-5,6-dihydropyridine-1(2H)-carboxylate

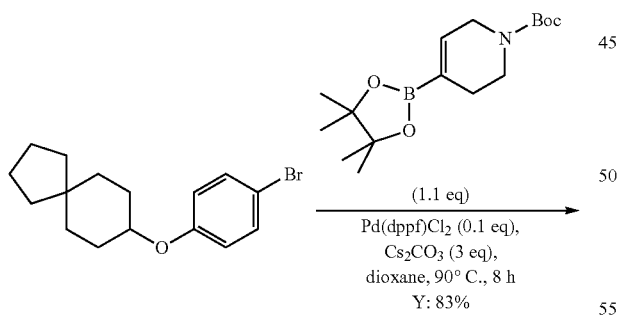

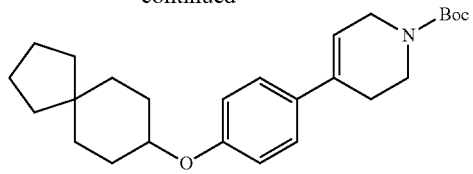

Using the same procedure as for intermediate 44, the title compound was obtained, as a yellow solid (1.77 g, 83% yield). ESI-MS (M+H)+: 412.2. ¹H NMR (400 MHz, CDCl₃) δ: 7.28 (d, J=8.8 Hz, 2H), 6.87 (d, J=8.8 Hz, 2H), 5.94-5.92 (m, 1H), 4.25-4.23 (m, 1H), 4.05-4.03 (m, 2H), 3.63-3.61 (m, 2H), 2.50-2.48 (m, 2H), 1.92-1.88 (m, 2H), 1.65-1.55 (m, 8H), 1.49 (s, 9H), 1.46-1.30 (m, 6H).

Intermediate 53: 4-(4-(spiro[4.5]decan-8-yloxy)phenyl)-1,2,3,6-tetrahydropyridine

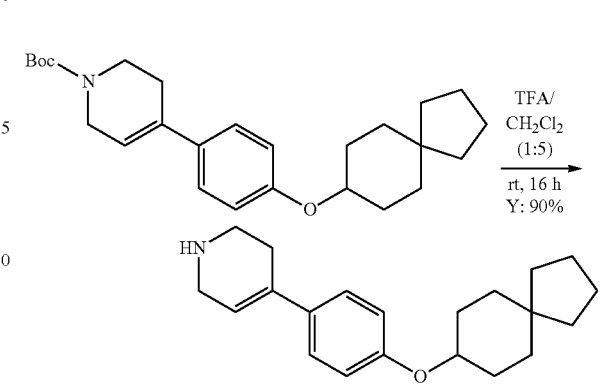

Using the same procedure as for intermediate 45, the title compound was obtained as a yellow solid (1.16 g, 90% yield). ESI-MS (M+H)+: 312.2. ¹H NMR (400 MHz, CDCl₃) δ: 8.81 (br, 1H), 7.27 (d, J=8.0 Hz, 2H), 6.88 (d, J=8.4 Hz, 2H), 5.91-5.90 (m, 1H), 4.27-4.25 (m, 1H), 3.88-3.86 (m, 2H), 3.47-3.46 (m, 2H), 2.78-2.76 (m, 2H), 1.91-1.88 (m, 2H), 1.63-1.59 (m, 8H), 1.48-1.34 (m, 6H).

Example 39

3-(4-(4-(Spiro[4.5]decan-8-yloxy)phenyl)-5,6-dihydropyridin-1(2H)-yl)propanoic acid (Compound 40)

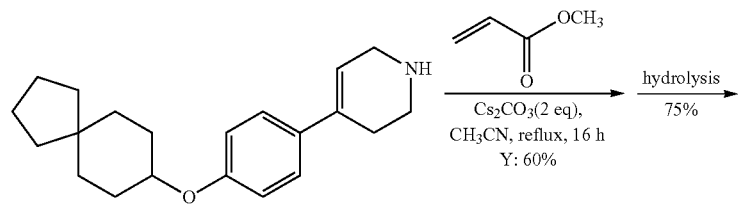

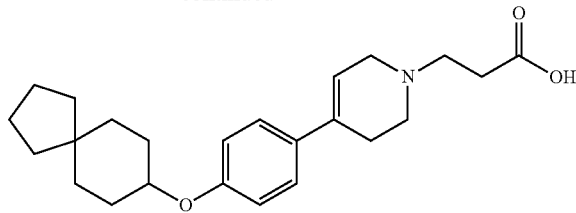

Using the same procedure as for intermediate 5, methyl 3-(4-(4-(spiro[4.5]decan-8-yloxy)phenyl)-5,6-dihydropyridin-1(2H)-yl)propanoate was obtained as a yellow solid (153 mg, 60% yield). ESI-MS (M+H)+: 398.2. $^1$H NMR (400 MHz, CDCl$_3$) δ: 7.28 (d, J=8.8 Hz, 2H), 6.84 (d, J=8.4 Hz, 2H), 5.95-5.94 (m, 1H), 4.25-4.23 (m, 1H), 3.71-3.69 (m, 3H), 3.21-3.19 (m, 2H), 2.86-2.56 (m, 6H), 1.92-1.88 (m, 2H), 1.65-1.57 (m, 10H), 1.48-1.33 (m, 6H).

Using standard hydrolysis condition, the title compound was obtained as a white solid (70 mg, 75% yield). ESI-MS (M+H)+: 384.2. $^1$H NMR (400 MHz, CDCl$_3$) δ: 7.38 (d, J=4.4 Hz, 2H), 6.90 (d, J=4.4 Hz, 2H), 6.03-6.02 (m, 1H), 4.35-4.31 (m, 1H), 3.95-3.93 (m, 2H), 3.57-3.55 (m, 2H), 3.50 (t, J=7.2 Hz, 2H), 2.85 (t, J=6.4 Hz, 4H), 1.92-1.86 (m, 2H), 1.65-1.56 (m, 8H), 1.49-1.34 (m, 6H).

Example 40

3-(4-(4-(Spiro[4.5]decan-8-yloxy)phenyl)piperidin-1-yl)propanoic acid (Compound 32)

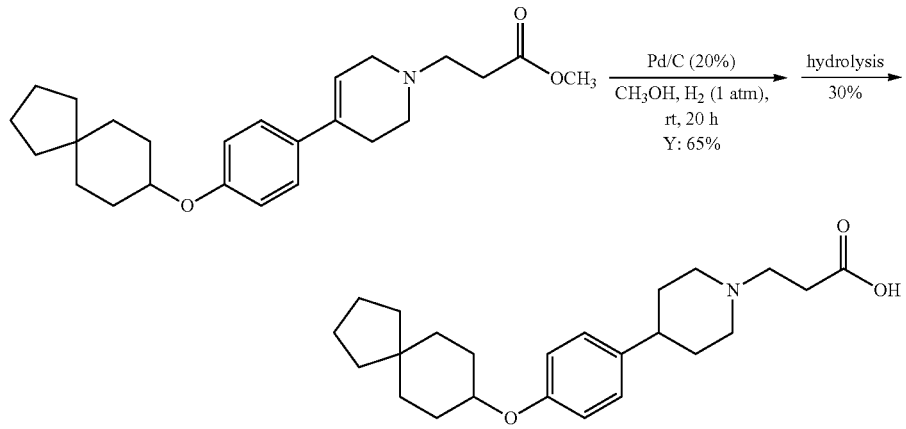

Using the same procedure as for intermediate 47, methyl 3-(4-(4-(spiro[4.5]decan-8-yloxy)phenyl)piperidin-1-yl)propanoate was obtained as yellow gum (90 mg, 65% yield). ESI-MS (M+H)+: 400.2.

Using standard hydrolysis condition, the title compound was obtained, as pale yellow gum (25 mg, 30% yield). ESI-MS (M+H)+: 386.2. $^1$HNMR (400 MHz, CDCl$_3$) δ: 7.09 (d, J=8.8 Hz, 2H), 6.84 (d, J=8.8 Hz, 2H), 4.20-4.18 (m, 1H), 3.35-3.33 (m, 2H), 2.96-2.94 (m, 2H), 2.59-2.52 (m, 5H), 1.95-1.87 (m, 6H), 1.61-1.58 (m, 8H), 1.47-1.25 (m, 6H).

Example 41

4-(4-(4-(Spiro[4.5]decan-8-yloxy)phenyl)-5,6-dihydropyridin-1(2H)-yl)butanoic acid (Compound 47)

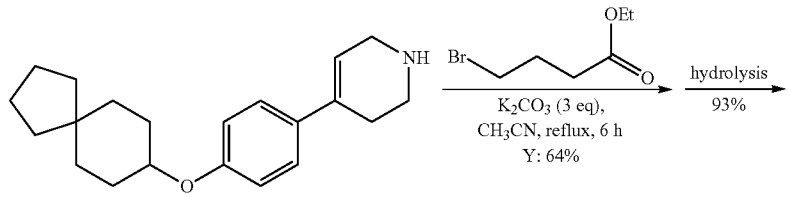

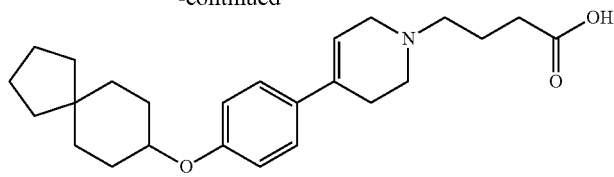

Using the same procedure as for intermediate 6, ethyl 4-(4-(4-(spiro[4.5]decan-8-yloxy)phenyl)-5,6-dihydropyridin-1(2H)-yl)butanoate was obtained as a yellow solid (260 mg, 64% yield). ESI-MS (M+H)$^+$: 426.2. $^1$HNMR (400 MHz, CDCl$_3$) δ: 7.28 (d, J=8.8 Hz, 2H), 6.84 (d, J=8.8 Hz, 2H), 5.96-5.94 (m, 1H), 4.24-4.22 (m, 1H), 4.13 (q, J=7.2 Hz, 2H), 3.15-3.14 (m, 2H), 2.70-2.68 (m, 2H), 2.54-2.47 (m, 4H), 2.37 (t, J=7.2 Hz, 2H), 1.92-1.87 (m, 4H), 1.63-1.26 (m, 14H), 1.25 (t, J=6.8 Hz, 3H).

Using standard hydrolysis condition, the title compound was obtained as a white solid (86 mg, 93% yield). ESI-MS (M+H)$^+$: 398.2. $^1$HNMR (400 MHz, CDCl$_3$) δ: 7.27 (d, J=8.8 Hz, 2H), 6.86 (d, J=8.8 Hz, 2H), 5.91-5.90 (m, 1H), 4.25-4.23 (m, 1H), 3.50-3.48 (m, 2H), 3.07-3.05 (m, 2H), 2.88-2.86 (m, 2H), 2.73-2.71 (m, 2H), 2.66-2.63 (m, 2H), 1.95-1.88 (m, 4H), 1.61-1.58 (m, 8H), 1.47-1.34 (m, 6H).

Example 42

4-(4-(4-(Spiro[4.5]decan-8-yloxy)phenyl)piperidin-1-yl)butanoic acid (Compound 35)

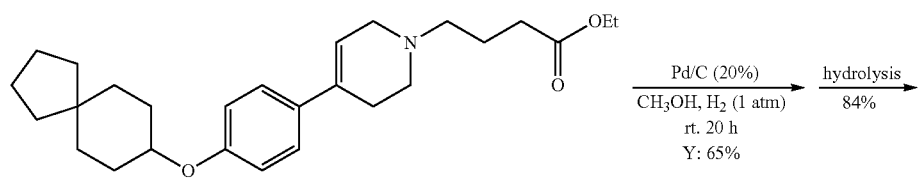

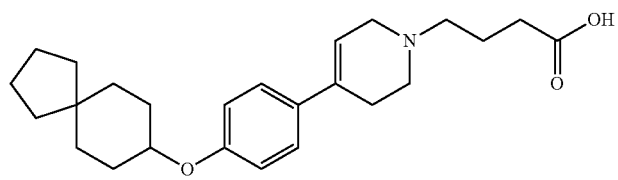

Using the same procedure as for intermediate 47, ethyl 4-(4-(4-(spiro[4.5]decan-8-yloxy)phenyl)piperidin-1-yl)butanoate was obtained as a yellow gum (98 mg, 65% yield). ESI-MS (M+H)$^+$: 428.3. $^1$HNMR (400 MHz, CDCl$_3$) δ: 7.04 (d, J=8.4 Hz, 2H), 6.76 (d, J=8.8 Hz, 2H), 4.13-4.11 (m, 1H), 4.06 (q, J=7.2 Hz, 2H), 3.02-3.00 (m, 2H), 2.40-2.35 (m, 2H), 2.29 (t, J=7.2 Hz, 2H), 2.04-2.02 (m, 2H), 1.84-1.74 (m, 8H), 1.54-1.52 (m, 9H), 1.40-1.24 (m, 6H), 1.19 (t, J=7.2 Hz, 3H).

Using standard hydrolysis condition, the title compound was obtained as a pale yellow solid (80 mg, 84% yield). ESI-MS (M+H)$^+$: 400.2. $^1$HNMR (400 MHz, CDCl$_3$) δ: 7.10 (d, J=9.2 Hz, 2H), 6.83 (d, J=8.8 Hz, 2H), 4.21-4.18 (m, 1H), 3.34-3.31 (m, 2H), 2.79-2.77 (m, 2H), 2.65-2.48 (m, 5H), 2.01-1.88 (m, 8H), 1.47-1.40 (m, 8H), 1.37-1.25 (m, 6H).

Intermediate 54: Ethyl 5-(4-(4-(spiro[4.5]decan-8-yloxy)phenyl)-5,6-dihydropyridin-1(2H)-yl)pentanoate

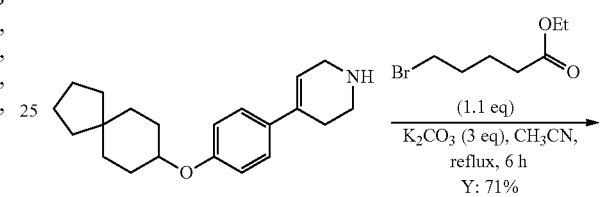

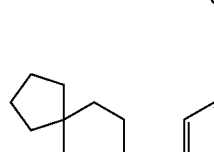

Using the same procedure as for intermediate 6, the title compound was obtained as a yellow solid (260 mg, 71% yield). ESI-MS (M+H)$^+$: 440.3. $^1$HNMR (400 MHz, CDCl$_3$) δ: 7.29 (d, J=8.8 Hz, 2H), 6.84 (d, J=8.8 Hz, 2H), 5.96-5.94 (m, 1H), 4.24-4.22 (m, 1H), 4.14 (q, J=7.2 Hz, 2H), 3.17-3.15 (m, 2H), 2.72-2.70 (m, 2H), 2.56-2.49 (m, 4H), 2.35 (t, J=7.2 Hz, 2H), 1.92-1.88 (m, 2H), 1.71-1.48 (m, 12H), 1.46-1.30 (m, 6H), 1.26 (t, J=7.2 Hz, 3H).

Example 43

5-(4-(4-(Spiro[4.5]decan-8-yloxy)phenyl)-5,6-dihydropyridin-1(2H)-yl)pentanoic acid (Compound 48)

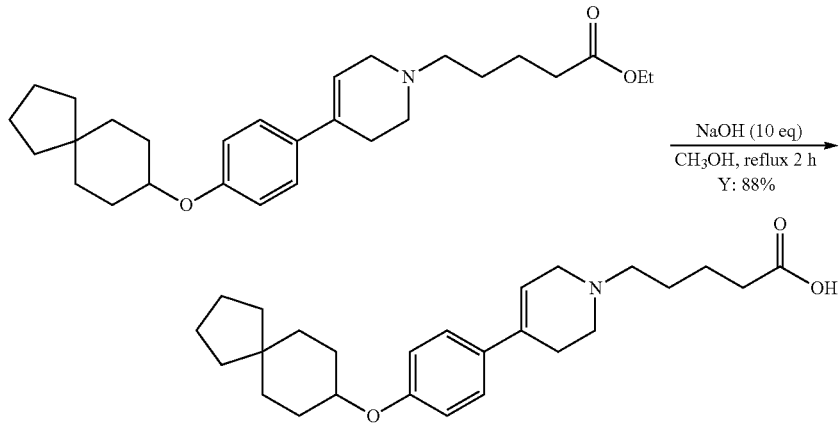

Using standard hydrolysis condition, the title compound was obtained as a white solid (85 mg, 91% yield), ESI-MS (M+H)$^+$: 412.3. $^1$HNMR (400 MHz, CD$_3$OD) δ: 7.40 (d, J=8.8 Hz, 2H), 6.91 (d, J=8.8 Hz, 2H), 6.05-6.03 (m, 1H), 4.35-4.33 (m, 1H), 3.86-3.84 (m, 2H), 3.47 (t, J=6.0 Hz, 2H), 3.18 (t, J=6.8 Hz, 2H), 2.86-2.84 (m, 2H), 2.32 (t, J=6.8 Hz, 2H), 1.89-1.81 (m, 4H), 1.73-1.62 (m, 10H), 1.49-1.39 (m, 6H).

Example 44

5-(4-(4-(Spiro[4.5]decan-8-yloxy)phenyl)piperidin-1-yl)pentanoic acid (Compound 33)

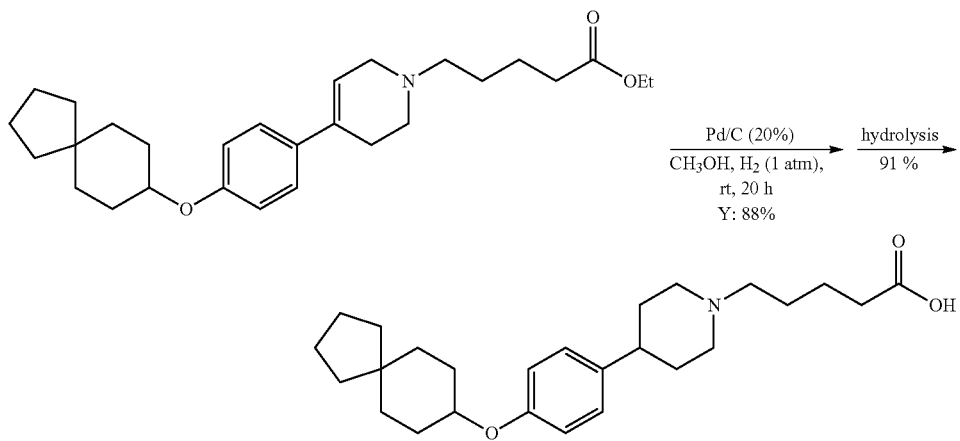

Using the same procedure as for intermediate 47, ethyl 5-(4-(4-(spiro[4.5]decan-8-yloxy)phenyl)piperidin-1-yl)pentanoate was obtained, as yellow gum (98 mg, 75% yield). ESI-MS (M+H)$^+$: 442.3. $^1$HNMR (400 MHz, CDCl$_3$) δ: 7.10 (d, J=8.4 Hz, 2H), 6.82 (d, J=8.8 Hz, 2H), 4.20-4.18 (m, 1H), 4.13 (q, J=7.2 Hz, 2H), 3.09-3.06 (m, 2H), 2.46-2.44 (m, 2H), 2.36-2.34 (m, 2H), 2.10-2.08 (m, 2H), 1.88-1.79 (m, 8H), 1.60-1.58 (m, 11H), 1.45-1.31 (m, 6H), 1.25 (t, J=7.2 Hz, 3H).

Using standard hydrolysis condition, the title compound was obtained as a pale yellow solid (80 mg, 88% yield). ESI-MS (M+H)$^+$: 414.3. $^1$HNMR (400 MHz, CDCl$_3$) δ: 7.11 (d, J=8.8 Hz, 2H), 6.83 (d, J=8.8 Hz, 2H), 4.21-4.19 (m, 1H), 3.60-3.57 (m, 2H), 2.86-2.84 (m, 3H), 2.60-2.58 (m, 2H), 2.36 (t, J=6.4 Hz, 2H), 2.24-2.21 (m, 2H), 2.21-1.84 (m, 6H), 1.69-1.42 (m, 10H), 1.39-1.31 (m, 6H).

Intermediate 55: 1-Bromo-4-((trans-4-(tert-Butyl)cyclohexyl)oxy)benzene

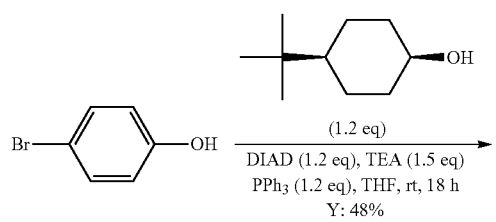

Using the same procedure as for intermediate 43, the title compound was obtained, as a white solid (150 mg, 48% yield). ESI-MS (M+H)$^+$: 311.1 $^1$H NMR (400 MHz, CDCl$_3$) δ: 7.29-7.25 (m, 2H), 6.72-6.68 (m, 2H), 4.00-3.96 (m, 1H), 2.11-2.07 (m, 2H), 1.80-1.77 (m, 2H), 1.35-1.17 (m, 2H), 1.06-0.98 (m, 3H), 0.80 (s, 9H).

Intermediate 56: tert-Butyl 4-(4-((trans-4-(tert-butyl)cyclohexyl)oxy)phenyl)-5,6-dihydropyridine-1(2H)-carboxylate

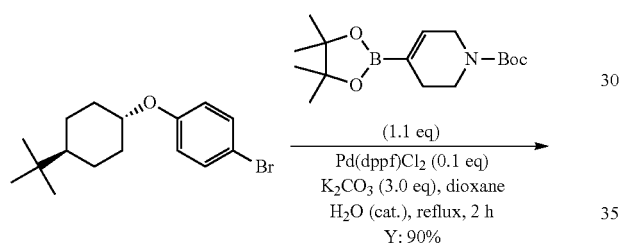

Using the same procedure as for intermediate 44, the title compound was obtained as a yellow solid (60 mg, 90% yield). ESI-MS (M+H)$^+$: 414.3. $^1$H NMR (400 MHz, CDCl$_3$) δ: 7.21 (d, J=8.4 Hz, 2H), 6.79 (d, J=8.8 Hz, 2H), 5.87-5.86 (m, 1H), 4.03-3.98 (m, 3H), 3.55 (t, J=6.0 Hz, 2H), 2.43-2.41 (m, 2H), 2.13-2.10 (m, 2H), 1.80-1.77 (m, 2H), 1.42 (s, 9H), 1.33-1.27 (m, 2H), 1.07-1.01 (m, 3H), 0.80 (s, 9H).

Intermediate 57: 4-(4-((trans-4-(tert-Butyl)cyclohexyl)oxy)phenyl)-1,2,3,6-tetrahydropyridine

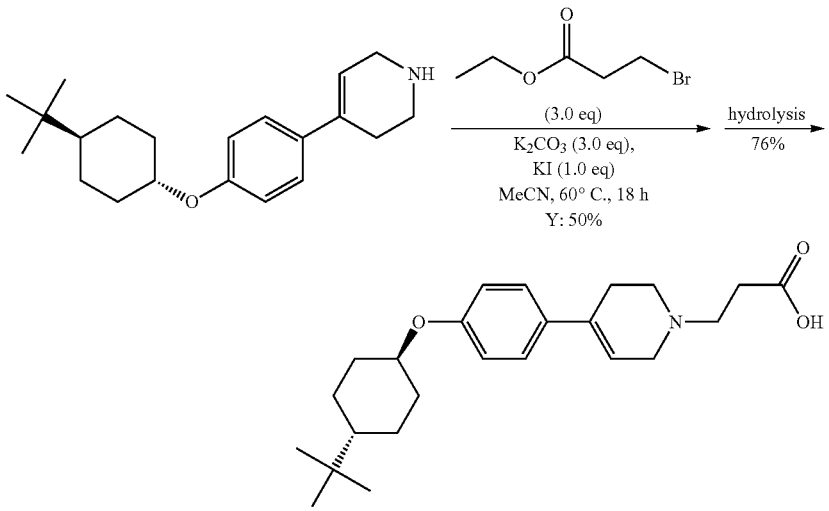

Using the same procedure as for intermediate 45, the title compound was obtained, as a yellow solid (45 mg, 99% yield). ESI-MS (M+H)$^+$: 314.2. $^1$H NMR (400 MHz, CDCl$_3$) δ: 7.28 (d, J=8.8 Hz, 2H), 6.85 (d, J=8.8 Hz, 2H), 6.01-5.99 (m, 1H), 4.13-4.08 (m, 1H), 3.58-3.57 (m, 3H), 3.16 (t, J=6.0 Hz, 2H), 2.50-2.49 (m, 2H), 2.20-2.17 (m, 2H), 1.87-1.84 (m, 2H), 1.43-1.33 (m, 2H), 1.14-1.05 (m, 3H), 0.87 (s, 9H).

Example 45

3-(4-(4-((trans-4-(tert-Butyl)cyclohexyl)oxy)phenyl)-5,6-dihydropyridin-1(2H)-yl)propanoic acid (Compound 38)

Using the same procedure as for intermediate 6, ethyl 3-(4-(4-((trans-4-(tert-butyl)cyclohexyl)oxy)phenyl)-5,6-dihydropyridin-1(2H)-yl)propanoate was obtained as a white solid (200 mg, 56% yield). ESI-MS (M+H)+: 414.3.

Using the standard hydrolysis condition, the title compound was obtained as a yellow solid (120 mg, 76% yield). ESI-MS (M+H)+: 386.3. $^1$H NMR (400 MHz, CD$_3$OD) δ: 7.29 (d, J=8.8 Hz, 2H), 6.80 (d, J=8.8 Hz, 2H), 5.94-5.92 (m, 1H), 4.13-4.06 (m, 1H), 3.86-3.84 (m, 2H), 3.50-3.47 (m, 2H), 3.41 (t, J=7.2 Hz, 2H), 2.78-2.74 (m, 4H), 2.09-2.06 (m, 2H), 1.80-1.76 (m, 2H), 1.27-1.02 (m, 5H), 0.80 (s, 9H).

Example 46

3-(4-(4-((trans-4-(tert-Butyl)cyclohexyl)oxy)phenyl)piperidin-1-yl)propanoic acid (Compound 27)

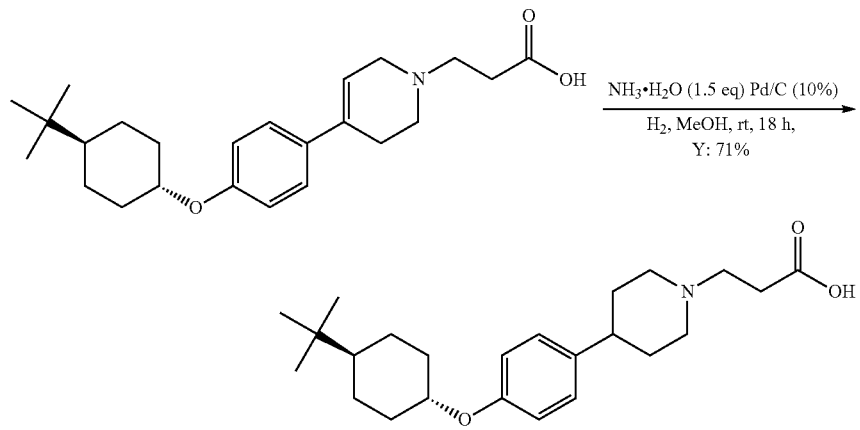

Using the same procedure as for intermediate 47, the title compound was obtained as a yellow solid (40 mg, 71% yield). ESI-MS (M+H)+: 388.3. $^1$H NMR (400 MHz, CD$_3$OD) δ: 7.05 (d, J=8.4 Hz, 2H), 6.76 (d, J=8.8 Hz, 2H), 4.07-4.00 (m, 1H), 3.58-3.55 (m, 2H), 3.34 (t, J=7.2 Hz, 2H), 3.12-3.02 (m, 2H), 2.77-2.70 (m, 3H), 2.05-1.97 (m, 4H), 1.86-1.75 (m, 4H), 1.23-0.95 (m, 5H), 0.79 (s, 9H).

Example 47

4-(4-(4-((trans-4-(tert-Butyl)cyclohexyl)oxy)phenyl)-5,6-dihydropyridin-1(2H)-yl)butanoic acid (Compound 37)

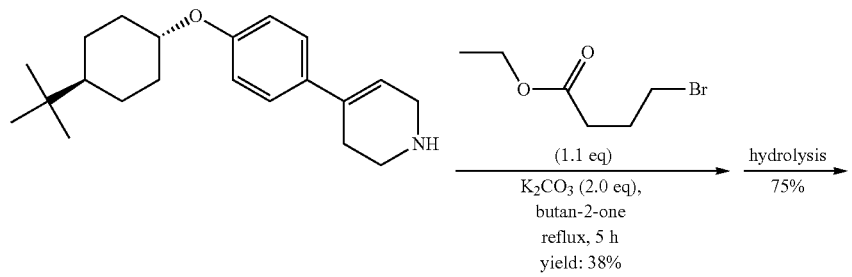

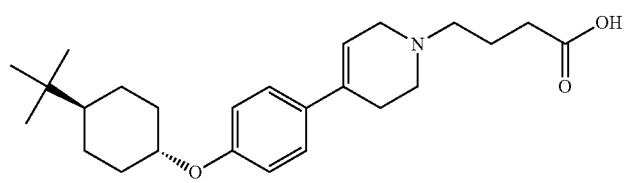

Using the same procedure as for intermediate 6, ethyl 4-(4-(4-((trans-4-(tert-butyl)cyclohexyl)oxy)phenyl)-5,6-dihydropyridin-1(2H)-yl)butanoate was obtained as a white solid (40 mg, 38% yield). ESI-MS (M+H)+: 428.3. $^1$H NMR (400 MHz, CDCl$_3$) δ: 7.29 (d, J=8.8 Hz, 2H), 6.84 (d, J=8.8 Hz, 2H), 5.96-5.94 (m, 1H), 4.13 (q, J=7.2 Hz, 2H), 4.13-4.10 (m, 1H), 3.17-3.15 (m, 2H), 2.70 (t, J=5.6 Hz, 2H), 2.54-2.48 (m, 4H), 2.37 (t, J=7.6 Hz, 2H), 2.20-2.17 (m, 2H), 1.92-1.84 (m, 4H), 1.43-1.33 (m, 2H), 1.25 (t, J=7.2, 3H), 1.11-1.07 (m, 3H), 0.87 (s, 9H).

Using standard hydrolysis condition, the title compound was obtained as a white solid (70 mg, 75% yield). ESI-MS (M+H)+: 400.1. $^1$H NMR (400 MHz, CDCl$_3$) δ: 7.26 (d, J=8.4 Hz, 2H), 6.86 (d, J=8.8 Hz, 2H), 5.87-5.85 (m, 1H), 4.15-4.08 (m, 2H), 3.67-3.58 (m, 2H), 2.71-2.69 (m, 3H), 2.54-2.45 (m, 4H), 2.18-2.09 (m, 4H), 1.87-1.84 (m, 2H), 1.42-1.33 (m, 2H), 1.17-1.02 (m, 3H), 0.87 (s, 9H).

Example 48

4-(4-(4-((trans-4-(tert-Butyl)cyclohexyl)oxy)phenyl)piperidin-1-yl)butanoic acid (Compound 25)

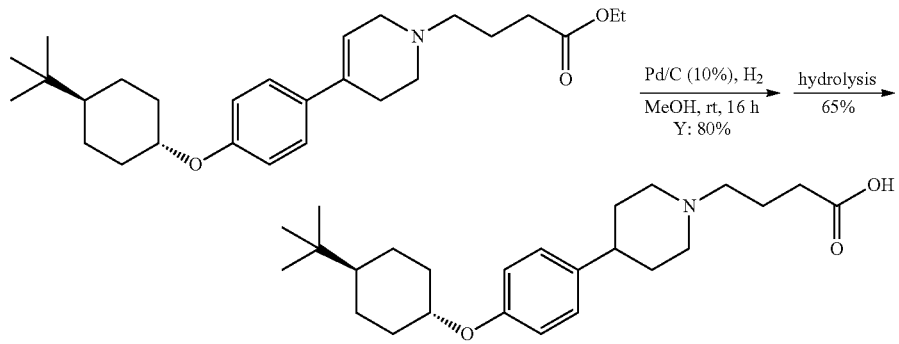

Using the same procedure as for intermediate 47, ethyl 4-(4-(4-((trans-4-(tert-butyl)cyclohexyl)oxy)phenyl)piperidin-1-yl)butanoate was obtained as a yellow oil (100 mg, 80% yield). ESI-MS (M+H)+: 430.3.

Using standard hydrolysis condition, the title compound was obtained as a white solid (60 mg, 65% yield). ESI-MS (M+H)+: 402.3. $^1$H NMR (400 MHz, CD$_3$OD) δ: 7.16 (d, J=8.8 Hz, 2H), 6.87 (d, J=8.8 Hz, 2H), 4.17-4.12 (m, 1H), 3.69 (d, J=12.0 Hz, 2H), 3.31-3.19 (m, 2H), 3.15-3.12 (m, 2H), 2.84-2.82 (m, 1H), 2.49 (t, J=6.8 Hz, 2H), 2.18-1.86 (m, 10H), 1.36-1.34 (m, 2H), 1.24-1.05 (m, 3H), 0.90 (s, 9H).

Example 49

5-(4-(4-((trans-4-(tert-Butyl)cyclohexyl)oxy)phenyl)-5,6-dihydropyridin-1(2H)-yl)pentanoic acid (Compound 46)

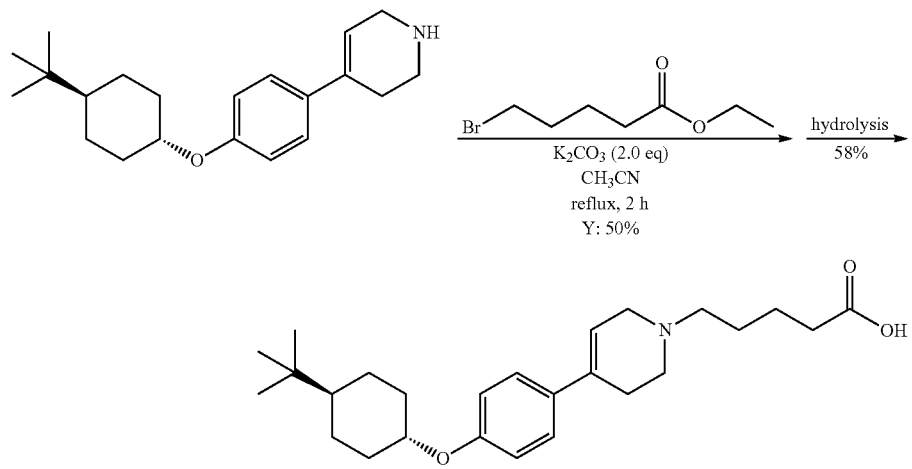

Using the same procedure as for intermediate 6, ethyl 5-(4-(4-((trans-4-(tert-butyl)cyclohexyl)oxy)phenyl)-5,6-dihydropyridin-1(2H)-yl)pentanoate was obtained as a yellow oil (440 mg, 50% yield). ESI-MS (M+H)$^+$: 442.3. $^1$H NMR (400 MHz, CDCl$_3$) δ: 7.28 (dd, J=6.8, 2.0 Hz, 2H), 6.83 (dd, J=7.2, 2.0 Hz, 2H), 5.95-5.94 (m, 1H), 4.13 (q, J=7.2 Hz, 2H), 4.10-4.06 (m, 1H), 3.17 (br, 2H), 2.71-2.69 (m, 2H), 2.57-2.53 (m, 2H), 2.51-2.47 (m, 2H), 2.35 (t, J=7.2 Hz, 2H), 2.20-2.16 (m, 2H), 1.87-1.83 (m, 2H), 1.70-1.60 (m, 4H), 1.42-1.33 (m, 2H), 1.26 (t, J=7.2 Hz, 3H), 1.16-1.02 (m, 3H), 0.87 (s, 9H).

Using standard hydrolysis condition, the title compound was obtained as a white solid (93 mg, 58% yield). ESI-MS (M+H)$^+$: 414.3. $^1$H NMR (400 MHz, CD$_3$OD) δ: 7.40 (d, J=8.8 Hz, 2H), 6.90 (d, J=8.8 Hz, 2H), 6.05-6.03 (m, 1H), 4.22-4.17 (m, 1H), 4.09-4.05 (m, 2H), 3.80-3.76 (m, 2H), 3.28-3.24 (m, 2H), 2.87-2.84 (m, 2H), 2.43 (t, J=7.2 Hz, 2H), 2.20-2.17 (m, 2H), 1.90-1.82 (m, 4H), 1.75-1.69 (m, 2H), 1.41-1.31 (m, 2H), 1.30-1.19 (m, 2H), 1.16-1.06 (m, 1H), 0.91 (s, 9H).

Example 50

5-(4-(4-((trans-4-(tert-Butyl)cyclohexyl)oxy)phenyl)piperidin-1-yl)pentanoic acid (Compound 34)

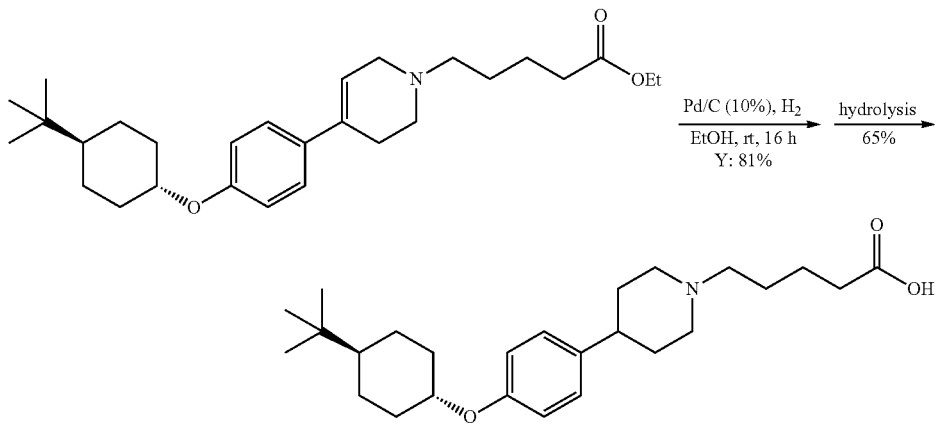

Using the same procedure as for intermediate 47, ethyl 5-(4-(4-((trans-4-(tert-butyl)cyclohexyl)oxy)phenyl)piperidin-1-yl)pentanoate was obtained as a yellow oil (200 mg, 81% yield). ESI-MS (M+H)$^+$: 444.3. $^1$H NMR (400 MHz, CDCl$_3$) δ: 7.11 (d, J=8.4 Hz, 2H), 6.82 (d, J=8.8 Hz, 2H), 4.13 (q, J=7.2 Hz, 2H), 4.08-4.03 (m, 1H), 3.07-3.04 (m, 2H), 2.31-2.24 (m, 1H), 2.43-2.38 (m, 2H), 2.35-2.31 (m, 2H), 2.19-2.16 (m, 2H), 2.04-2.01 (m, 2H), 1.82-1.76 (m, 6H), 1.68-1.58 (m, 4H), 1.41-1.32 (m, 2H), 1.26 (t, J=7.2 Hz, 3H), 1.15-1.05 (m, 3H), 0.87 (s, 9H).

Using standard hydrolysis condition, the title compound was obtained as a white solid (100 mg, 65% yield). ESI-MS (M+H)$^+$: 416.3. $^1$H NMR (400 MHz, CD$_3$OD) δ: 7.15 (d, J=9.2 Hz, 2H), 6.86 (d, J=8.4 Hz, 2H), 4.17-4.10 (m, 1H), 3.65-3.62 (m, 2H), 3.16-3.07 (m, 4H), 2.83-2.79 (m, 1H), 2.37 (t, J=6.8 Hz, 2H), 2.18-2.14 (m, 2H), 2.08-1.94 (m, 4H), 1.88-1.80 (m, 4H), 1.71-1.68 (m, 2H), 1.37-1.29 (m, 2H), 1.13-1.05 (m, 3H), 0.89 (s, 9H).

Example 51

Activity Measurements

S1P Receptor Activity Assays

Agonist percentage activation determinations were obtained by assaying sample compounds and referencing the Emax control for each receptor profiled. Antagonist percentage inhibition determinations were obtained by assaying sample compounds and referencing the control EC80 wells for each receptor profiled. The samples were run using a "Single Addition" assay protocol for the agonist and antagonist assay run. The protocol design was as follows:

Compound Preparation

Master stock solution: Unless specified otherwise, all sample compounds were diluted in 100% anhydrous DMSO including all serial dilutions. All control wells contained identical solvent final concentrations as did the sample compound wells.

Compound plate for assay: The sample compounds were transferred from a master stock solution into a daughter plate that was used in the assay. Each sample compound was diluted into assay buffer (1×HBSS with 20 mM HEPES and 2.5 mM Probenecid) at an appropriate concentration to obtain final concentrations.

Calcium Flux Assay: Agonist Assay Format

Sample compounds were plated in an eight-point, four-fold dilution series in duplicate with a top concentration of 10 μM. The concentrations described here reflect the final concentration of the compounds during the antagonist assay. During the agonist assay the compound concentrations were 1.25 fold higher to allow for the final desired concentration to be achieved with further dilution by EC$_{80}$ of reference agonists during the antagonist assay.

Reference agonists were handled as mentioned above serving as assay control. The reference agonists were handled as described above for Emax.

Assay was read for 180 seconds using the FLIPRTETRA (This assay run added sample compounds and reference agonist to respective wells). At the completion of the first "Single Addition" assay run, assay plate was removed from the FLIPRTETRA and placed at 25° C. for seven (7) minutes.

Calcium Flux Assay: Antagonist Assay Format

Using the EC$_{80}$ values determined during the agonist assay, stimulated all pre-incubated sample compound and reference antagonist (if applicable) wells with $EC_{80}$ of reference agonist. Read for 180 seconds using the FLIP-RTETRA (This assay added reference agonist to respective wells—then fluorescence measurements were collected to calculate percentage inhibition values).

Data Processing

All plates were subjected to appropriate baseline corrections. Once baseline corrections were processed, maximum fluorescence values were exported and data manipulated to calculate percentage activation, percentage inhibition and Z'.

The compounds of examples 37 and 46-48 had an $IC_{50}$ of no greater than 2 µM for $S1P_1$ agonist activity. The compounds of examples 38, 40 and 45 had an $IC_{50}$ between 2 µM and 5 µM for $S1P_1$ agonist activity. The compounds of examples 1, 2, 4-6, 9-36, 39, 41-44, 49 and 50 had an $IC_{50}$ of greater than 5 µM for $S1P_1$.

The compounds of examples 1, 2 and 4-50 had an $IC_{50}$ of greater than 5 µM for $S1P_3$.

The compounds of examples 2, 5-8, 12, 14, 15, 19, 21, 23-25, 29-31, 33, 35, 37, 38, 40 and 44-49 had an $IC_{50}$ of no greater than 2 µM for $S1P_4$ agonist activity. The compounds of examples 13, 17-18, 20, 26, 36, 39 and 41-43 had an $IC_{50}$ between 2 µM and 5 µM for $S1P_4$ agonist activity. The compounds of examples 16 and 50 had an $IC_{50}$ of no greater than 5 uM of $S1P_4$ agonist activity. The compounds of examples 1, 4, 9-11, 22, 27, 28, 32 and 34 had an $IC_{50}$ of greater than 5 µM for $S1P_4$.

The compounds of examples 40, 44, 47 and 48 had an $IC_{50}$ of no greater than 2 µM for $S1P_5$. The compounds of examples 37 and 41 had an $IC_{50}$ between 2 µM and 5 µM for $S1P_5$. The compounds of examples 1, 2, 4-10, 14-24, 26-36, 38, 39, 42, 43, 45, 46, 49 and 50 had an $IC_{50}$ of greater than 5 µM for $S1P_5$.

Autotaxin (ATX) Assay

ATX (Autotaxin) is a 125 KDa glycoprotein with lysophospholipase D (LPLD) activity that generates the bioactive lipid lysophosphatidic acid (LPA) from lysophosphatidylcholine (LPC). The ATX biochemical assay utilizes a FRET (fluorescence resonance energy transfer) technology platform. The fluorescence signal of FRET substrate FS-3 is quenched due to intra-molecular FRET of a fluorophore to a non-fluorescing quencher (Ferguson, C. G., et al., Org Lett. 2006 May 11; 8(10): 2023-2026, which is incorporated by reference in its entirety). ATX catalyzes the hydrolysis of the substrate which separates the dabsyl quencher from the fluorescein reporter, which becomes fluorescent. The reaction is monitored by a SpectraMax M5 (Molecular Devices, Sunnyvale, Calif.) with at excitation wavelength 485 nm and emission wavelength 535 nm.

Reagents

Fatty acid free-BSA (Sigma A8806): 10 mg/mL in $H_2O$, stored at 4° C.

2×ATX assay buffer: 100 mM Tris, 280 mM NaCl, 10 mM KCl, 2 mM $CaCl_2$, 2 mM $MgCl_2$, pH 7.4.

Human ATX protein: expressed and purified in house. Stored at −80° C.

Substrate FS-3 (Echelon, L-2000): 100 µg in 77.74 µL $H_2O$ (1 mM stock), stored at −20° C.

384-well flat bottom plates—Corning #3575.

Assay

Compound dilution—All compounds were provided at 10 mM in 100% DMSO. In the first well, 2 µL of 10 mM compound was added to 78 µL of DMSO (1:40 dilution). In subsequent wells 3-fold dilution (total 10 dilutions) were performed.

1×ATX assay buffer was made up with a final concentration of 1 mg/mL fatty acid free-BSA using 2×ATX assay buffer, 10 mg/ml fatty acid free-BSA and dd$H_2O$.

ATX protein was diluted with 1×ATX assay buffer to a concentration of 1.32 µg/mL (1.32×). 38 µL was added per well to the assay plate. The final concentration of ATX in the reaction as 1.0 µg/mL.

2 µL per well of compounds was transferred to provide the desired concentration. The plate was centrifuged, then incubated at room temperature for 30 minutes on the shaker.

FS-3 was diluted with 1×ATX assay buffer to a concentration of FS-3 of 10 µM (5×). Then, 10 µL was added per well to the assay plate. The final concentration of FS-3 in the reaction was 2 µM. The plate was centrifuged. The plate was kept shaking at room temperature for 2 hours. Because FS-3 substrate is light sensitive, plates were kept covered and protected from light.

Fluorescence was measured using SpectraMax M5 (excitation at 485 nm/emission at 538 nm, top read).

The compounds of examples 16, 19, 32, 37, 40, 41, 47 and 48 had an $IC_{50}$ of no greater than 5 µM. The compounds of examples 3-8, 11, 20, 21, 26, 27, 36, 42, 45 and 46 had an $IC_{50}$ between 5 µM and 10 µM. The compounds of examples 9, 10, 12-15, 17, 18, 28-31, 33-35, 38, 39, 43 and 44 had an $IC_{50}$ greater than 10 µM.

OPC Differentiation Assay

Enriched populations of oligodendrocytes were grown from post-natal day 2 (P2) female Sprague Dawley rats. The forebrain was dissected out and placed in Hank's buffered saline solution (HBSS; Invitrogen, Grand Island, N.Y.). The tissue was cut into 1 mm fragments and incubated at 37° C. for 15 minutes in 0.01% trypsin and 10 µg/mL DNase. Dissociated cells were plated on poly-L-lysine-coated T75 tissue culture flasks and grown at 37° C. for 10 days in Dulbecco's modified Eagle's medium (DMEM) with 20% fetal calf serum (Invitrogen). A2B5+OPCs were collected by shaking the flask overnight at 200 rpm and 37° C., resulting in a 95% pure population.

For the differentiation assay, 2 µM and 20 µM antagonist or the same concentrations of vehicle (DMSO) were applied to OPCs cultured in CNTF/T3 containing media. After a 3-day incubation, after a 3-day incubation, cell were lysed and then subjected to MSD (Meso Scale Discovery-R) analysis. $EC_{50}$ was calculated by Prism using a nonlinear sigmoidal dose-response curvecells. Alternatively, cells were lysed in 80 µL lysis buffer (50 mM HEPES [4-(2-hydroxyethyl)-1-piperazineethanesulfonic acid], pH 7.5, 150 mM NaCl, 1.5 mM MgCl2, 1 mM ethylene glycol tetraacetic acid (EGTA), 1% Triton X-100 and 10% glycerol) for 30 minutes at 4° C. After centrifugation at 14,000 g for 15 minutes, the supernatants were boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used were anti-mouse IgG-HRP (horseradish peroxidase) and anti-rabbit IgG-HRP respectively.

The compounds of examples 14 and 16 were positive in the OPC assay.

OPC Oligodendrocyte Myelination Assay

Embryonic neocortical neurons are dissected from embryonic day 18 (E18) Sprague Dawley rats, and then plated on poly-D-lysine (100 µg/mL)-coated cover slips and grown in neurobasal medium supplemented with B27 (Invitrogen) for one week. A2B5+OPCs are prepared as described above and then added into the cultured neocortical neurons. One day later, different concentrations of an $S1P_4$ receptor antagonist and control reagents are applied into the co-cultures. Fresh media containing the different concentrations of an $S1P_4$ receptor antagonist or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 µm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an $S1P_4$ receptor antagonist or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 µL of 1% Lysolecithin (LPC, Sigma# L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administrated subcutaneously (s.c.) twice a day for additional two days following operation.

Three days following the primary surgery, treatments with an $S1P_4$ receptor antagonist (30 pmol), LPA (30 pmol) or control (0.1% DMSO in saline) are injected at the primary injection region in a volume of 1.5 µL with the same infusion speed as indicated above. Nine days following the primary surgery, the animals are anesthetized and perfused transcardially with heparin (10 iu/mL) in saline followed by 4% PFA in PBS. The spinal cords are removed and post fixed in PFA overnight. Then the cords are cut into 100 µM thickness longitudinally and then 1% loxuol fast blue is stained and histological evaluation for remyelination and repair is assessed under microscope.

For systemic treatment, the animals are administered once daily intraperitoneally with either an $S1P_4$ receptor antagonist (10 mg/kg) or control (15% HPCD (hydroxypropyl-β-cyclodextrin)) 2 days following the primary surgery. Nine days after the primary surgery, animals are sacrificed and the spinal cords were processed as indicated above.

Calcium Mobilization

Compounds that are not specific for a particular S1P receptor can cause undesirable side effects. Accordingly, compounds are tested to identify those that are specific. Accordingly, the test compounds are tested in a calcium mobilization assay. The procedure is essentially as described in Davis et al. (2005) Journal of Biological Chemistry, vol. 280, pp. 9833-9841, which is incorporated by reference in its entirety with the following modifications. Calcium mobilization assays are performed in recombinant CHEM cells expressing human $S1P_1$, $S1P_2$, $S1P_3$, $S1P_4$, or $S1P_5$ purchased from Millipore (Billerica, Mass.). To detect free intracellular calcium, $S1P_1$, $S1P_2$, $S1P_3$, $S1P_4$, or $S1P_5$ cells are loaded with FLIPR Calcium 4 dye from Molecular Devices (Sunnyvale, Calif.). Cells are imaged for calcium mobilization using a FLIPRTETRA equipped with a 96-well dispense head.

In Vivo Screening Assays

Measurement of circulating lymphocytes: Compounds are dissolved in 30% HPCD. Mice (C57bl/6 male, 6-10 week-old) are administered 0.5 and 5 mg/kg of a compound via oral gavage 30% HPCD is included as a negative control.

Blood is collected from the retro-orbital sinus 5 and 24 hours after drug administration under short isoflurane anesthesia. Whole blood samples are subjected to hematology analysis. Peripheral lymphocyte counts are determined using an automated analyzer (HEMAVET™ 3700). Subpopulations of peripheral blood lymphocytes are stained by fluorochrome-conjugated specific antibodies and analyzed using a fluorescent activating cell sorter (FACSCALIBUR™). Three mice are used to assess the lymphocyte depletion activity of each compound screened.

Compounds of formula (I), or pharmaceutically acceptable salts thereof, can induce full lymphopenia at times as short as 4 hours or less to as long as 48 hours or more; for example, 4 to 36 hours, or 5 to 24 hours. In some cases, a compound of formula can induce full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less.

Other embodiments are within the scope of the following claims.

What is claimed is:

1. A compound represented by formula (I):

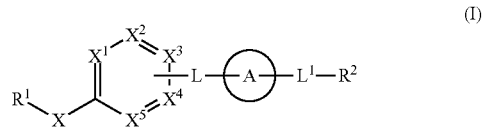

(I)

or a pharmaceutically acceptable salt thereof, wherein:
X is —O—, —S(O)$_r$—, —CH$_2$—, or —NR—, wherein r is 0, 1, or 2;
$X^1$, $X^2$, and $X^5$ are each independently $CR^7$ or N;
$X^3$ is C and is attached by a single bond to -L-, and $X^4$ is $CR^7$ or N, provided that no more than three of $X^1$, $X^2$, $X^3$, $X^4$ or $X^5$ are N;

Ring A is monocyclic $C_{5-6}$cycloalkyl or a 5- to 6-membered monocyclic heterocyclyl comprising from 1 to 5 heteroatoms independently selected from N, S, or O; wherein Ring A is further optionally substituted with from 1 to 3 $R^4$; provided that Ring A is not morpholinyl, thiomorpholinyl or tetrahydro-2H-pyranyl;

L is a bond, —O—, —NR—, —S(O)$_r$—, —CH$_2$—, or —C(O)—, wherein n is 0, 1, or 2;

$L^1$ is an $C_{1-8}$alkylene, $C_{3-8}$cycloalkylene, —CH$_2$-L$^2$-, or a 3- to 8-membered heterocyclylene comprising 1 to 5 heteroatoms selected from N, S, or O; wherein $L^1$ may be optionally substituted with from 1 to 3 independently selected $R^5$;

$L^2$ is a divalent bridged ring system comprising 6-10 ring members, wherein the ring members may be all carbon atoms or may comprise 1 to 5 heteroatoms selected from N, S, or O;

R, for each occurrence, is independently hydrogen or $C_{1-8}$alkyl;

$R^1$ is a monocyclic $C_{3-8}$cycloalkyl; wherein said $C_{3-8}$cycloalkyl is substituted with at least one $R^6$ and may be optionally substituted with from 1 to 5 additional $R^6$ substituents, wherein $R^6$ for each occurrence is independently selected;

$R^2$ is —C(O)OR$^3$, —C(O)N(R$^3$)—S(O)$_2$R$^3$, —S(O)$_2$OR$^3$, —C(O)NHC(O)R$^3$, —Si(O)OH, —B(OH)$_2$, —N(R$^3$)S(O)$_2$R$^3$, —S(O)$_2$N(R$^3$)$_2$, —O—P(O)(OR$^3$)$_2$, or —P(O)(OR$^3$)$_2$, —CN, —S(O)$_2$NHC(O)R$^3$, —C(O)NHS(O)$_2$R$^3$, —C(O)NHOH, —C(O)NHCN, —CH(CF$_3$)OH, —C(CF$_3$)$_2$OH, or a heteroaryl or a heterocyclyl selected from the group consisting of formulae (a)-(i'):

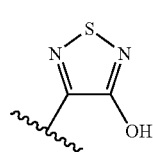
(a)

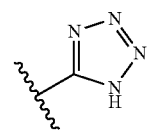
(b)

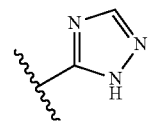
(c)

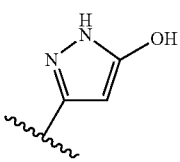
(d)

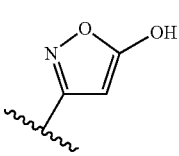
(e)

-continued

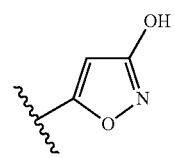
(f)

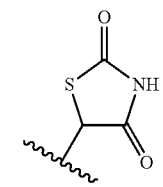
(g)

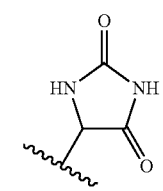
(h)

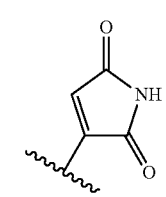
(i)

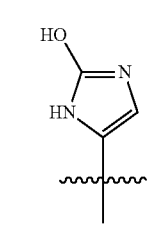
(j)

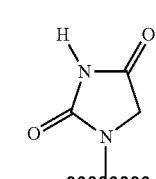
(k)

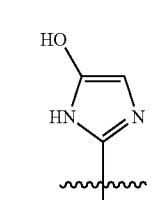
(l)

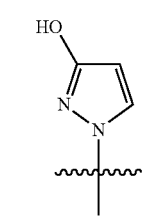
(m)

| | |
|---|---|
| 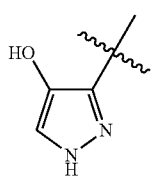 (n) | 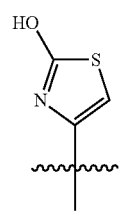 (u) |
| 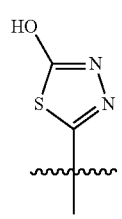 (o) | 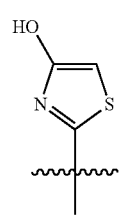 (v) |
| 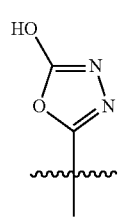 (p) | 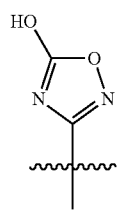 (w) |
| 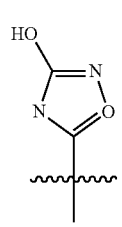 (q) | 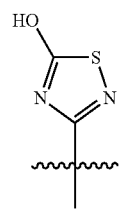 (x) |
| 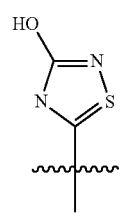 (r) | 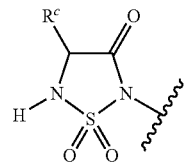 (y) |
| 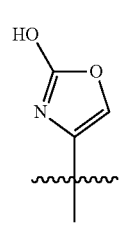 (s) | 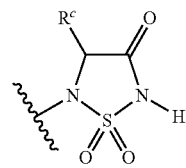 (z) |
| 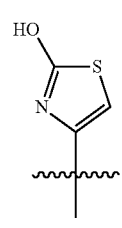 (t) | 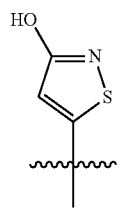 (a') |
| | 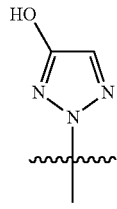 (b') |

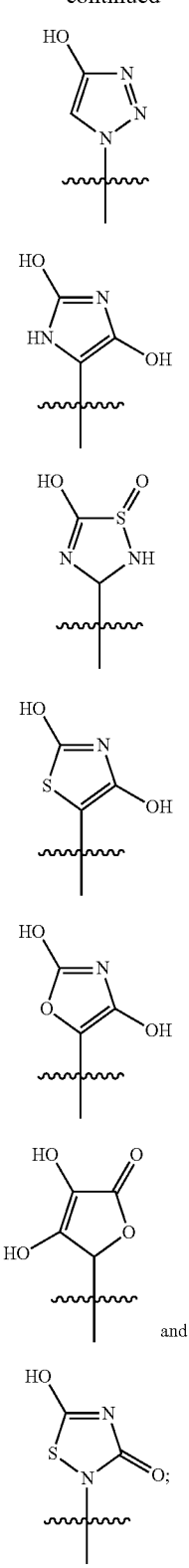

$R^3$ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 12 membered heteroaryl, and a 3 to 12 membered heterocyclyl; wherein the heteroaryl and heterocyclyl independently comprise from 1 to 6 heteroatoms selected from O, N, or S; and wherein $R^3$ may be optionally substituted with from 1 to 3 substituents independently selected from the group consisting of halo, $C_{1-4}$alkoxy, $C_{1-4}$alkyl, cyano, nitro, hydroxyl, amino, N—$C_{1-4}$alkylamino, N,N-di-($C_{1-4}$alkyl) amino, carbamoyl, N—$C_{1-4}$alkylcarbamoyl, N,N-di-($C_{1-4}$alkyl)carbamoyl, $C_{1-4}$alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl;

$R^4$ and $R^5$, for each occurrence, are independently halo, hydroxyl, nitro, cyano, $C_{1-8}$alkyl, $C_{1-8}$haloalkyl, $C_{1-8}$alkoxy, $C_{1-4}$haloalkoxy, $C_{2-8}$alkenyl, $C_{2-8}$alkynyl, $C_{3-8}$cycloalkyl, $C_{3-8}$halocycloalkyl, $C_{3-8}$cycloalkoxy, $C_{3-8}$halocycloalkoxy, —$NR^aR^b$, —$C(O)NR^aR^b$, —$N(R^a)C(O)R^b$, —$C(O)R^a$, —$S(O)_pR^a$, or —$N(R^a)S(O)_2R^b$, wherein p for each occurrence is independently 0, 1, or 2;

$R^6$, for each occurrence, is independently halo, hydroxyl, mercapto, nitro, $C_{1-8}$alkyl, $C_{1-8}$haloalkyl, $C_{1-8}$alkoxy, $C_{1-4}$haloalkoxy, $C_{1-8}$ alkylthio, $C_{2-8}$alkenyl, $C_{2-8}$alkynyl, cyano, —$NR^aR^b$, $C_{3-8}$cycloalkyl, $C_{3-8}$halocycloalkyl, $C_{6-10}$aryl, 3- to 8-membered heterocyclyl, or 5- to 6-membered heteroaryl, wherein the heterocyclyl and heteroaryl comprise 1 to 4 heteroatoms independently selected from O, N, or S; or two $R^6$ on the same carbon atom together with the carbon to which they are attached form a $C_{3-8}$spirocycloalkyl;

$R^7$, for each occurrence, is independently hydrogen, halo, hydroxyl, nitro, cyano, $C_{1-7}$alkyl, $C_{1-7}$haloalkyl, $C_{1-7}$alkoxy, $C_{1-4}$haloalkoxy, $C_{2-7}$alkenyl, $C_{2-7}$alkynyl, $C_{3-8}$cycloalkyl, $C_{3-8}$halocycloalkyl, $C_{3-8}$cycloalkoxy, $C_{3-8}$halocycloalkoxy, —$NR^cR^d$, —$C(O)NR^cR^d$, —$N(R^c)C(O)R^b$, —$C(O)R^a$, —$S(O)_pR^a$, and —$N(R^c)S(O)_2R^b$, wherein p is 0, 1, or 2; and $R^a$ and $R^b$, for each occurrence, are independently hydrogen, $C_{1-8}$alkyl, $C_{2-8}$alkenyl, $C_{2-8}$alkynyl, $C_{3-8}$cycloalkyl, $C_{6-10}$aryl, or $C_{3-8}$halocycloalkyl.

2. The compound of claim 1, or a pharmaceutically acceptable salt thereof, wherein X is —O—.

3. The compound of claim 1, or a pharmaceutically acceptable salt thereof, wherein Ring A is monocyclic $C_{5-6}$cycloalkyl.

4. The compound of claim 1, or a pharmaceutically acceptable salt thereof, wherein Ring A is 5- to 6-membered monocyclic heterocyclyl comprising from 1 to 5 heteroatoms independently selected from N, S, or O.

5. The compound of claim 1, or a pharmaceutically acceptable salt thereof, wherein Ring A is 5- to 6-membered monocyclic heterocyclyl comprising from 1 to 2 heteroatoms independently selected from N.

6. The compound of claim 1, or a pharmaceutically acceptable salt thereof, wherein L is a bond, or —NR—.

7. The compound of claim 1, or a pharmaceutically acceptable salt thereof, wherein L is a bond.

8. The compound of claim 1, or a pharmaceutically acceptable salt thereof, wherein $L^1$ is an $C_{1-8}$alkylene, $C_{3-8}$cycloalkylene, —$CH_2$-$L^2$-, or a 3- to 8-membered heterocyclylene comprising 1 to 5 N.

9. The compound of claim 1, or a pharmaceutically acceptable salt thereof, wherein $L^1$ is $C_{1-8}$alkylene.

10. The compound of claim 1, or a pharmaceutically acceptable salt thereof, wherein $L^2$ is a divalent bridged ring system comprising 6-10 ring members, wherein the ring members are all carbon atoms.

11. The compound of claim 1, or a pharmaceutically acceptable salt thereof, wherein R, for each occurrence, is hydrogen.

12. The compound of claim 1, or a pharmaceutically acceptable salt thereof, wherein $R^1$ is monocyclic $C_{3-8}$cycloalkyl; wherein said $C_{3-8}$cycloalkyl is substituted with at least one $R^6$ and may be optionally substituted with from 1 to 5 additional $R^6$ substituents, wherein $R^6$ for each occurrence is independently selected; and
$R^6$, for each occurrence, is independently $C_{1-8}$alkyl; or two $R^6$ on the same carbon atom together with the carbon to which they are attached form a $C_{3-8}$spirocycloalkyl.

13. The compound of claim 1, or a pharmaceutically acceptable salt thereof, wherein $R^2$ is —C(O)OR$^3$.

14. The compound of claim 1, or a pharmaceutically acceptable salt thereof, wherein $R^2$ is —C(O)OR$^3$, and $R^3$ is hydrogen.

15. The compound of claim 1, or a pharmaceutically acceptable salt thereof, wherein:
X is —O—;
$X^1$, $X^2$, and $X^5$ are each independently CH or N;
$X^3$ is C and is attached by a single bond to -L-, and $X^4$ is CH or N, provided that no more than three of $X^1$, $X^2$, $X^3$, $X^4$ or $X^5$ are N;
Ring A is an unsubstituted monocyclic $C_{5-6}$cycloalkyl or a 5- to 6-membered monocyclic heterocyclyl comprising from 1 to 5 heteroatoms independently selected from N, S, or O; provided that Ring A is not morpholinyl, thiomorpholinyl or tetrahydro-2H-pyranyl;
L is a bond, or —NR—;
$L^1$ is an $C_{1-8}$alkylene, $C_{3-8}$cycloalkylene, —CH$_2$-L$^2$-, or a 3- to 8-membered heterocyclylene comprising 1 to 5 N;
$L^2$ is a divalent bridged ring system comprising 6-10 ring members, wherein the ring members are all carbon atoms;
R, for each occurrence, is hydrogen;
$R^1$ is a monocyclic $C_{3-8}$cycloalkyl; wherein said $C_{3-8}$cycloalkyl is substituted with at least one $R^6$ and may be optionally substituted with from 1 to 5 additional $R^6$ substituents, wherein $R^6$ for each occurrence is independently selected;
$R^2$ is —C(O)OR$^3$, —C(O)N(R$^3$)—S(O)$_2$R$^3$, —S(O)$_2$OR$^3$, —C(O)NHC(O)R$^3$, —Si(O)OH, —B(OH)$_2$, —N(R$^3$)S(O)$_2$R$^3$, —S(O)$_2$N(R$^3$)$_2$, —O—P(O)(R$^3$)$_2$, or —P(O)(OR$^3$)$_2$, —CN, —S(O)$_2$NHC(O)R$^3$, —C(O)NHS(O)$_2$R$^3$, —C(O)NHOH, —C(O)NHCN, —CH(CF$_3$)OH, —C(CF$_3$)$_2$OH, or a heteroaryl or a heterocyclyl selected from the group consisting of formulae (a)-(i'):

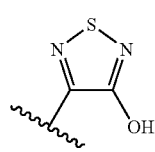

(a)

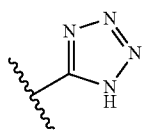

(b)

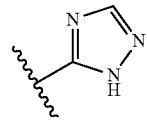

(c)

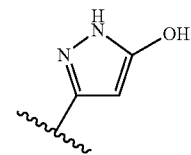

(d)

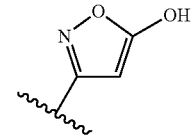

(e)

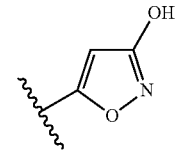

(f)

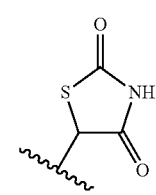

(g)

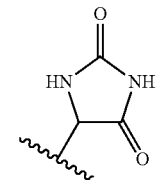

(h)

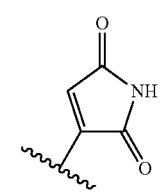

(i)

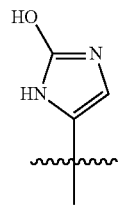

(j)

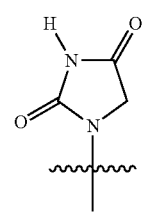

(k)

-continued
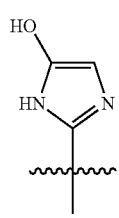 (l)
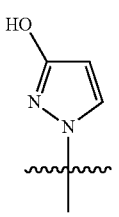 (m)
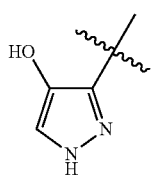 (n)
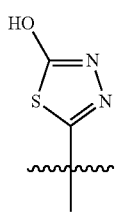 (o)
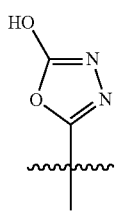 (p)
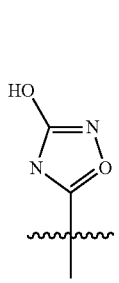 (q)
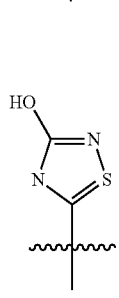 (r)
-continued
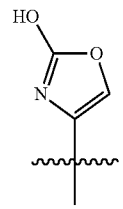 (s)
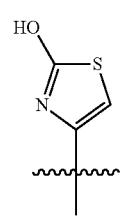 (t)
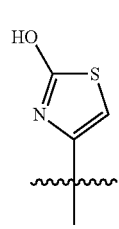 (u)
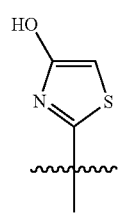 (v)
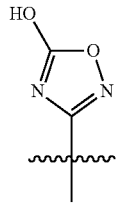 (w)
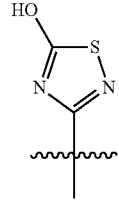 (x)
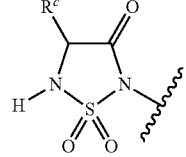 (y)
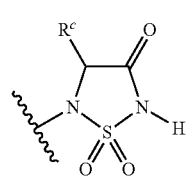 (z)

(a') 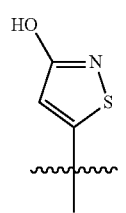

(b') 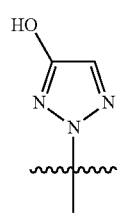

(c') 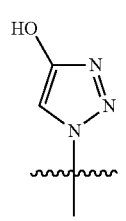

(d') 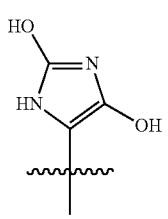

(e') 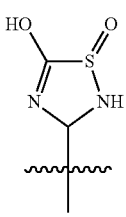

(f') 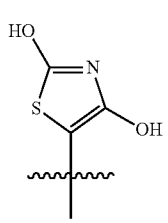

(g') 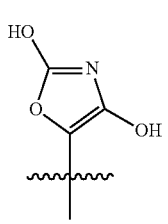

(h') 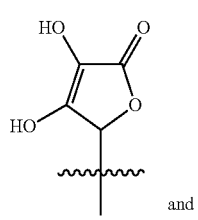

and (i') 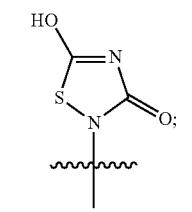

$R^3$ for each occurrence is independently selected from the group consisting of hydrogen, $C_{1-8}$alkyl, $C_{2-8}$alkenyl, $C_{2-8}$alkynyl, $C_{3-8}$cycloalkyl, $C_{3-8}$cycloalkenyl, $C_{6-10}$aryl, a 5 to 12 membered heteroaryl, and a 3 to 12 membered heterocyclyl; wherein the heteroaryl and heterocyclyl independently comprise from 1 to 6 heteroatoms selected from O, N, or S; and wherein $R^3$ may be optionally substituted with from 1 to 3 substituents independently selected from the group consisting of halo, $C_{1-4}$alkoxy, $C_{1-4}$alkyl, cyano, nitro, hydroxyl, amino, N—$C_{1-4}$alkylamino, N,N-di-($C_{1-4}$alkyl)amino, carbamoyl, N—$C_{1-4}$alkylcarbamoyl, N,N-di-($C_{1-4}$alkyl)carbamoyl, $C_{1-4}$ alkylamido, $C_{1-4}$alkylsulfonyl, $C_{1-4}$alkylsulfonamido, sulfamoyl, N—$C_{1-4}$alkylsulfamoyl, and N,N—($C_{1-4}$dialkyl)-sulfamoyl; and $R^6$, for each occurrence, is independently $C_{1-8}$alkyl; or two $R^6$ on the same carbon atom together with the carbon to which they are attached form a $C_{3-8}$spirocycloalkyl.

16. A compound, or pharmaceutically acceptable salt thereof, selected from the group consisting of:

3-(4-(4-((trans-4-(tert-Butyl)cyclohexyl)oxy)phenyl)piperazin-1-yl)propanoic acid;

4-(4-(4-((trans-4-(tert-Butyl)cyclohexyl)oxy)phenyl)piperazin-1-yl)butanoic acid;

3-(3-(4-(trans-4-tert-Butylcyclohexyloxy)phenyl)piperidin-1-yl)propanoic acid;

4-(3-(4-(cis-4-tert-Butylcyclohexyloxy)phenyl)piperidin-1-yl)butanoic acid;

4-((4-(4-((trans-4-(tert-Butyl)cyclohexyl)oxy)phenyl)piperazin-1-yl)methyl)bicyclo[2.2.2]octane-1-carboxylic acid;

1-(3-(4-(trans-4-tert-butylcyclohexyloxy)phenyl)cyclohexyl)piperidine-4-carboxylic acid;

3-(3-(5-(trans-4-tert-butylcyclohexyloxy)pyridin-2-ylamino)piperidin-1-yl)propanoic acid;

3-(3-((4-((trans-4-(tert-Butyl)cyclohexyl)oxy)phenyl)amino)piperidin-1-yl)propanoic acid;

3-(3-(4-((trans-4-(tert-Butyl)cyclohexyl)oxy)phenyl)pyrrolidin-1-yl)propanoic acid;

4-(3-(4-((trans-4-(tert-Butyl)cyclohexyl)oxy)phenyl)pyrrolidin-1-yl)butanoic acid;

3-(3-(3-((trans-4-(tert-Butyl)cyclohexyl)oxy)phenyl)piperidin-1-yl)propanoic acid;

4-(3-(3-((trans-4-(tert-Butyl)cyclohexyl)oxy)phenyl)piperidin-1-yl)butanoic acid;

4-(3-(4-((trans-4-(tert-Butyl)cyclohexyl)oxy)phenyl)piperidin-1-yl)cyclohexanecarboxylic acid;
4-(4-(4-((trans-4-(tert-Butyl)cyclohexyl)oxy)phenyl)piperidin-1-yl)butanoic acid;
3-(4-(4-((cis-4-Ethylcyclohexyl)oxy)phenyl)piperidin-1-yl)propanoic acid;
3-(4-(4-((trans-4-(tert-Butyl)cyclohexyl)oxy)phenyl)piperidin-1-yl)propanoic acid;
5-(4-(4-((trans-4-Ethylcyclohexyl)oxy)phenyl)piperidin-1-yl)pentanoic acid;
4-(4-(4-((trans-4-Ethylcyclohexyl)oxy)phenyl)piperidin-1-yl)butanoic acid;
3-(4-(4-((trans-4-ethylcyclohexyl)oxy)phenyl)piperidin-1-yl)propanoic acid;
5-(4-(4-((cis-4-Ethylcyclohexyl)oxy)phenyl)piperidin-1-yl)pentanoic acid;
3-(4-(4-(Spiro[4.5]decan-8-yloxy)phenyl)piperidin-1-yl)propanoic acid;
5-(4-(4-(Spiro[4.5]decan-8-yloxy)phenyl)piperidin-1-yl)pentanoic acid;
5-(4-(4-((trans-4-(tert-Butyl)cyclohexyl)oxy)phenyl)piperidin-1-yl)pentanoic acid;
4-(4-(4-(Spiro[4.5]decan-8-yloxy)phenyl)piperidin-1-yl)butanoic acid;
4-(4-(4-((cis-4-Ethylcyclohexyl)oxy)phenyl)piperidin-1-yl)butanoic acid;
4-(4-(4-((trans-4-(tert-Butyl)cyclohexyl)oxy)phenyl)-5,6-dihydropyridin-1(2H)-yl)butanoic acid;
3-(4-(4-((trans-4-(tert-Butyl)cyclohexyl)oxy)phenyl)-5,6-dihydropyridin-1(2H)-yl)propanoic acid;
3-(4-(4-((cis-4-Ethylcyclohexyl)oxy)phenyl)-5,6-dihydropyridin-1(2H)-yl)propanoic acid;
3-(4-(4-(Spiro[4.5]decan-8-yloxy)phenyl)-5,6-dihydropyridin-1(2H)-yl)propanoic acid;
4-(4-(4-((cis-4-Ethylcyclohexyl)oxy)phenyl)-5,6-dihydropyridin-1(2H)-yl)butanoic acid;
5-(4-(4-((cis-4-Ethylcyclohexyl)oxy)phenyl)-5,6-dihydropyridin-1(2H)-yl)pentanoic acid;
5-(4-(4-((trans-4-Ethylcyclohexyl)oxy)phenyl)-5,6-dihydropyridin-1(2H)-yl)pentanoic acid;
4-(4-(4-((trans-4-Ethylcyclohexyl)oxy)phenyl)-5,6-dihydropyridin-1(2H)-yl)butanoic acid;
3-(4-(4-((trans-4-Ethylcyclohexyl)oxy)phenyl)-5,6-dihydropyridin-1(2H)-yl)propanoic acid;
5-(4-(4-((trans-4-(tert-Butyl)cyclohexyl)oxy)phenyl)-5,6-dihydropyridin-1(2H)-yl)pentanoic acid;
4-(4-(4-(Spiro[4.5]decan-8-yloxy)phenyl)-5,6-dihydropyridin-1(2H)-yl)butanoic acid; and
5-(4-(4-(Spiro[4.5]decan-8-yloxy)phenyl)-5,6-dihydropyridin-1(2H)-yl)pentanoic acid.

17. A pharmaceutical composition comprising at least one compound of claim 1, or a pharmaceutically acceptable salt thereof, and at least one pharmaceutically acceptable carrier.

18. A method of treating, or reducing symptoms of a condition mediated by S1P activity and/or ATX activity in a mammal comprising administering to said mammal an effective amount of at least one compound of claim 1, or a pharmaceutically acceptable salt thereof.

19. The method of claim 18, wherein the condition is selected from the group consisting of multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, non-insulin dependent diabetes, a fibrosis of the lung, or a malignancy of the lung in a mammal.

20. The method of claim 19, further comprising administering to said mammal an effective amount of one or more drugs selected from the group consisting of: a corticosteroid, a bronchodilator, an antiasthmatic, an antiinflammatory, an antirheumatic, an immunosuppressant, an antimetabolite, an immunomodulating agent, an antipsoriatic, and an antidiabetic.

21. A method of promoting myelination or remyelination in a mammal in need thereof, comprising administering to cells an effective amount of at least one compound of claim 1, or a pharmaceutically acceptable salt thereof.

22. A method of treating, or reducing chronic pain in a mammal comprising administering to said mammal an effective amount of at least one compound of claim 1, or a pharmaceutically acceptable salt thereof.

* * * * *

UNITED STATES PATENT AND TRADEMARK OFFICE
CERTIFICATE OF CORRECTION

PATENT NO. : 9,850,206 B2  
APPLICATION NO. : 14/443912  
DATED : December 26, 2017  
INVENTOR(S) : Hairuo Peng et al.

Page 1 of 1

It is certified that error appears in the above-identified patent and that said Letters Patent is hereby corrected as shown below:

In the Claims

At Column 127, Claim number 1, Line number 7, please replace ", -S(O)$_r$-," with -- , -S(O)$_n$-, --.

Signed and Sealed this  
Twenty-fourth Day of April, 2018

Andrei Iancu  
*Director of the United States Patent and Trademark Office*